United States Patent
Bongartz et al.

(10) Patent No.: US 8,946,228 B2
(45) Date of Patent: Feb. 3, 2015

(54) PIPERIDINE/PIPERAZINE DERIVATIVES

(75) Inventors: Jean-Pierre André Marc Bongartz, Turnhout (BE); Joannes Theodorus Maria Linders, Eindhoven (NL); Lieven Meerpoel, Beerse (BE); Guy Rosalia Eugeen Van Lommen, Berlaar (BE); Erwin Coesemans, Nijlen (BE); Mirielle Braeken, Wechelderzande (BE); Christophe Francis Robert Nestor Buyck, Hamme (BE); Monique Jenny Marie Berwaer, Manhay (BE); Katharina Antonia Germania J. M. De Waepenaert, Vosselaar (BE); Peter Walter Maria Roevens, Malle (BE); Petr Vladimirivich Davidenko, Moscow (RU)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 12/663,011

(22) PCT Filed: Jun. 6, 2008

(86) PCT No.: PCT/EP2008/057008
§ 371 (c)(1),
(2), (4) Date: Dec. 4, 2009

(87) PCT Pub. No.: WO2008/148849
PCT Pub. Date: Dec. 11, 2008

(65) Prior Publication Data
US 2010/0210618 A1 Aug. 19, 2010

(30) Foreign Application Priority Data

Jun. 8, 2007 (EP) .................................... 07109866

(51) Int. Cl.
| | |
|---|---|
| *A61K 31/4965* | (2006.01) |
| *C07D 241/04* | (2006.01) |
| *C07D 295/00* | (2006.01) |
| *A61K 31/451* | (2006.01) |
| *A61K 31/495* | (2006.01) |
| *C07D 207/323* | (2006.01) |
| *C07D 211/26* | (2006.01) |
| *C07D 231/12* | (2006.01) |
| *C07D 233/54* | (2006.01) |
| *C07D 233/64* | (2006.01) |
| *C07D 235/18* | (2006.01) |
| *C07D 249/08* | (2006.01) |
| *C07D 257/04* | (2006.01) |
| *C07D 263/34* | (2006.01) |
| *C07D 277/56* | (2006.01) |
| *C07D 279/02* | (2006.01) |
| *C07D 279/12* | (2006.01) |
| *C07D 295/20* | (2006.01) |
| *C07D 307/54* | (2006.01) |
| *C07D 319/18* | (2006.01) |
| *C07D 401/12* | (2006.01) |

(Continued)

(52) U.S. Cl.
CPC ............. *A61K 31/451* (2013.01); *A61K 31/495* (2013.01); *C07D 207/323* (2013.01); *C07D 211/26* (2013.01); *C07D 231/12* (2013.01); *C07D 233/54* (2013.01); *C07D 233/64* (2013.01); *C07D 235/18* (2013.01); *C07D 249/08* (2013.01); *C07D 257/04* (2013.01); *C07D 263/34* (2013.01); *C07D 277/56* (2013.01); *C07D 279/02* (2013.01); *C07D 279/12* (2013.01); *C07D 295/20* (2013.01); *C07D 307/54* (2013.01); *C07D 319/18* (2013.01); *C07D 401/12* (2013.01); *C07D 417/12* (2013.01); *C07D 417/14* (2013.01)
USPC ...................................... 514/255.03; 544/392

(58) Field of Classification Search
USPC ...................................... 514/255.03; 544/392
See application file for complete search history.

(56) References Cited

U.S. PATENT DOCUMENTS

| | | | |
|---|---|---|---|
| 4,698,352 | A | 10/1987 | Narita et al. |
| 5,429,770 | A | 7/1995 | Closs et al. |

(Continued)

FOREIGN PATENT DOCUMENTS

| | | |
|---|---|---|
| CN | 1749256 A | 3/2006 |
| EP | 030371 A | 6/1981 |

(Continued)

OTHER PUBLICATIONS

Lee, et al., Inhibition of Diacylglycerol Acyltransferase by Alkamides Isolated from the Fruits of *Piper longum* and *Piper nigrum*, J. Agric. Food Chem., 54, 9759-9763 (2006).*
RN 854989-58-5.*
RN 859099-41-5.*
RN 859135-44-7.*
RN 859646-88-1.*
RN 860081-71-6.*

(Continued)

*Primary Examiner* — Erich A Leeser

(57) ABSTRACT

The invention relates to a DGAT inhibitor of formula (I), $$R^2-X-N\underset{A}{\overset{}{\bigcirc}}-\underset{}{\overset{R^7}{\bigcirc}}-Y-R^1,$$ (I)

including any stereochemically isomeric form thereof, a N-oxide thereof, a pharmaceutically acceptable salt thereof or a solvate thereof, and methods for preparing such compounds, pharmaceutical compositions comprising said compounds as well as the use as a medicine, as a DGAT inhibitor, of said compounds.

14 Claims, No Drawings

(51) Int. Cl.
  *C07D 417/12* (2006.01)
  *C07D 417/14* (2006.01)

(56) References Cited

U.S. PATENT DOCUMENTS

| | | | |
|---|---|---|---|
| 5,574,055 | A | 11/1996 | Borgulya et al. |
| 5,789,412 | A | 8/1998 | Halazy et al. |
| 6,492,368 | B1 | 12/2002 | Dorsch et al. |
| 6,884,868 | B1 | 4/2005 | Tojo et al. |
| 7,186,683 | B2 | 3/2007 | Henriksen et al. |
| 2003/0055055 | A1 | 3/2003 | Teuber et al. |
| 2003/0060472 | A1 | 3/2003 | Learmonth et al. |
| 2004/0038858 | A1 | 2/2004 | Dorsch et al. |
| 2004/0162282 | A1 | 8/2004 | Pennell et al. |
| 2004/0220191 | A1 | 11/2004 | Schwink et al. |
| 2005/0059650 | A1 | 3/2005 | Jones et al. |
| 2005/0209241 | A1 | 9/2005 | Jolidon |
| 2006/0030612 | A1 | 2/2006 | Steffan |
| 2007/0021339 | A1 | 1/2007 | Alloza Miravete et al. |
| 2007/0207999 | A1 | 9/2007 | Stadtmueller et al. |
| 2007/0249620 | A1 | 10/2007 | Kutura et al. |

FOREIGN PATENT DOCUMENTS

| | | | |
|---|---|---|---|
| EP | 321131 A | | 6/1989 |
| EP | 378207 A | | 7/1990 |
| EP | 630954 A | | 12/1994 |
| EP | 657440 A | | 6/1995 |
| EP | 1764360 A | | 3/2007 |
| GB | 1383906 A | | 2/1974 |
| JP | 11139969 | | 5/1999 |
| JP | 2005/206492 | | 8/2005 |
| JP | 2005-330266 A | | 12/2005 |
| JP | 2007131584 A | | 5/2007 |
| WO | WO 96/01820 A | | 1/1996 |
| WO | WO 96/01822 A | | 1/1996 |
| WO | 96/21648 A1 | | 7/1996 |
| WO | WO 97/05877 A | | 2/1997 |
| WO | WO 97/05878 A | | 2/1997 |
| WO | 97/30995 A1 | | 3/1997 |
| WO | WO 98/24766 A | | 6/1998 |
| WO | WO 99/16751 A | | 8/1999 |
| WO | 00/05225 A1 | | 2/2000 |
| WO | WO 00/32582 A1 | | 6/2000 |
| WO | WO 00/71107 | | 11/2000 |
| WO | WO 01/58885 A | | 8/2001 |
| WO | 01/95856 A2 | | 12/2001 |
| WO | 01/98251 A1 | | 12/2001 |
| WO | WO 01/97810 A2 | | 12/2001 |
| WO | WO 02/20501 A2 | | 3/2002 |
| WO | WO 02/20501 A3 | | 3/2002 |
| WO | 02/48117 A1 | | 6/2002 |
| WO | 02/055012 A1 | | 7/2002 |
| WO | WO 02/081460 A1 | | 10/2002 |
| WO | WO 03/064386 A | | 8/2003 |
| WO | 03/076421 A1 | | 9/2003 |
| WO | 03/076422 A1 | | 9/2003 |
| WO | 2003/087057 A1 | | 10/2003 |
| WO | WO 03/082864 A | | 10/2003 |
| WO | 2004/018439 A1 | | 3/2004 |
| WO | WO 2004/047755 A2 | | 6/2004 |
| WO | 2004/069792 A2 | | 8/2004 |
| WO | WO 2004/069792 | * | 8/2004 |
| WO | WO 2004/072025 A | | 8/2004 |
| WO | 2006/047277 A1 | | 10/2004 |
| WO | WO 2004/100881 A2 | | 11/2004 |
| WO | WO 2004/110375 A2 | | 12/2004 |
| WO | WO 2005/072740 A3 | | 8/2005 |
| WO | WO 2006/004200 A1 | | 1/2006 |
| WO | WO 2006/034441 A1 | | 3/2006 |
| WO | 2006/038039 A1 | | 4/2006 |
| WO | WO 2006/038039 A | | 4/2006 |
| WO | WO 2006/044775 A | | 4/2006 |
| WO | 2006/064189 A1 | | 6/2006 |
| WO | WO 2006/067071 A1 | | 6/2006 |
| WO | WO 2006/086445 A3 | | 8/2006 |
| WO | WO 2006/094842 A | | 9/2006 |
| WO | 2006/105127 A2 | | 10/2006 |
| WO | WO 2006/106326 A | | 10/2006 |
| WO | WO 2006/113919 A2 | | 10/2006 |
| WO | WO 2006/113919 A3 | | 10/2006 |
| WO | WO 2006/134317 A | | 12/2006 |
| WO | 2007/071023 A1 | | 6/2007 |
| WO | 2007/071966 A1 | | 6/2007 |
| WO | 2007/096351 A1 | | 8/2007 |
| WO | WO 2007/100990 A | | 9/2007 |
| WO | 2008/003766 A2 | | 1/2008 |
| WO | 2008/052638 A1 | | 5/2008 |
| WO | 2008/122787 A1 | | 10/2008 |
| WO | WO 2008/141976 A1 | | 11/2008 |
| WO | WO 2008/148840 A1 | | 12/2008 |
| WO | WO 2008/148849 A2 | | 12/2008 |
| WO | WO 2008/148851 A1 | | 12/2008 |
| WO | WO 2008/148868 A1 | | 12/2008 |
| WO | 2009/147170 A2 | | 12/2009 |

OTHER PUBLICATIONS

RN 860458-98-6.*
RN 861994-10-7.*
RN 884476-57-7.*
RN 892188-37-3.*
RN 892208-87-6.*
RN 892693-34-4.*
RN 897172-00-8.*
RN 897548-47-9.*
RN 898117-91-4.*
Chen, et al., Inhibition of Triglyceride Synthesis as a Treatment Strategy for Obesity: Lessons From DGAT1-Deficient Mice, Arterioscler Thromb Vasc Biol, 25:482-486 (2005).*
International Search Report, International Application No. PCT/EP2008/057008, Date of Mailing of International Search Report, Mar. 4, 2009.
International Preliminary Report on Patentability, relating to International Application No. PCT/EP2008/057008, Date of Completion of IPER, Oct. 5, 2009.
Birch et al., "DGAT1 inhibitors as anti-obesity and anti-diabetic agents.", *Current Opinion in Drug Discovery & Development*, 2010, pp. 489-496, vol. 13(4), Thomas Reuters.
Chen et al., "Enhancing energy and glucose metabolism by disruption triglyceride synthesis; Lessons from mice lacking DGAT1.", *Nutrition & Metabolism*, Jan. 31, 2006; pp. 1-4, vol. 3(10).
Chen et al., "DGAT and Triglyceride Synthesis: A New Target for Obesity Treatment?", *Trends Cardiovasc. Med.*, 2000, pp. 188-192, vol. 10(5).
Chen et al., "Inhibition of Triglyceride Synthesis as a Treatment Strategy for Obesity. Lessons from DGAT1-Deficient Mice.", *Arterioscler. Thromb. Vasc. Biol.*, 2005, pp. 482-486, vol. 25.
Matsuda and Tomoda, "DGAT inhibitors for obesity", *Current Opinion in Investigational Drugs*, 2007, pp. 836-841, vol. 8(10).
Okawa et al., "Role of MGAT2 and DGAT1 in the release of gut peptides after triglyceride ingestion", *Biochemical and Biophysical Research Communications*, 2009, pp. 377-381, vol. 390.
Bose et al., "Glucagon-like Peptide 1 Can Directly Protect the Heart Against Ischemia/Reperfusion Injury.", Diabetes, Jan. 2005, vol. 54, pp. 146-151.
Buhman et al., "DGAT1 Is Not Essential for Intestinal Triacylglycerol Absorption or Chylomicron Synthesis.", J. Biol. Chem. Jul. 12, 2002, vol. 277(28), pp. 25474-25479.
Cases et al., "Cloning of DGAT2, a Second Mammalian Diacylglycerol Acyltransferase, and Related Family Members.", J. Biol. Chem., Oct. 19, 2001, vol. 276(42), pp. 38870-38876.
Cases et al., "Identification of a gene encoding an acyl CoA:diacylglycerol acyltransferase, a key enzyme in triacylglycerol synthesis.", Proc. Natl. Acad. Sci., Oct. 1998, vol. 95, pp. 13018-13023.
Chen et al., "DGAT and Triglyceride Synthesis: A New Target for Obesity Treatment?", Trends Cardiovasc. Med., 2000, vol. 10(5), pp. 188-192.
Chen et al., "Increased insulin and leptin sensitivity in mice lacking acyl CoA:diacylglycerol acyltransferase 1.", J. Clin. Invest., 2002, vol. 109(8), pp. 1049-1055.

(56) References Cited

OTHER PUBLICATIONS

Database Registry, Aug. 3, 2005, XP002501332.
Database Registry, Aug. 5, 2005, XP002501333.
Database Registry, Aug. 8, 2005, XP002501334.
Database Registry, Aug. 8, 2005, XP002501335.
Database Registry, Mar. 22, 2004, XP002459101.
Database Registry, Mar. 22, 2004, XP002459102.
Database Registry, Mar. 22, 2004, XP002459103.
Database Registry, Nov. 3, 2004, XP002459099.
Farese et al., "Triglyceride synthesis: insights from the cloning of diacylglycerol acytransferase.", Curr. Opin. Lipidol. 2000, vol. 11, pp. 229-234.
Glass et al., "4-(4-Guanidinobenzoyl)-2-Imidazolones and Related Compounds: Phosphodiesterase Inhibitors and Novel Cardiotonics With Combined Histamine H2 Receptor Agonist and PDE III Inhibitor Activity.", Archiv. Der Pharmazie, 1995, vol. 328 (10), pp. 709-719, XP009002222.
Griffett et al., "Effects of 6-[p(4-phenylacetylpiperazine-1-yl)phenyl1]-4, 5-dihydro-3(2 H)pyridazinone (CCI 17810) and aspirin on platelet aggregation and adhesiveness.", Database Medline, British J. of Pharmacology, Apr. 1981, vol. 72(4), pp. 697-705, XP002459094.
Jiang et al., "Synthesis and platelet aggregation inhibitory activity of 6-(4-substituted phenyl)-4,5-dihydro-3(2H)-pyridazinones.", Database CA, Chemical Abstracts Service, XP002459098, (1990).
Khalaj et al., "Synthesis and antibacterial activity of 2-(4-substituted phenyl)-3(2H)-isothiazolones.", European Journal of Med. Chem., Aug. 2004, vol. 39(8), pp. 699-705, Paris, France, XP004523234.
Lewis et al., "Disordered fat storage and mobilization in the pathogenesis of insulin resistance and type 2 diabetes.", Endocrine Reviews, 2002, vol. 23(1), pp. 201-229.
Malloy and Kane, Pathogenesis and treatment in cardiomyopathy., Adv. Intern. Med., 2001, vol. 47, pp. 111-136.
Smith et al., "Obesity resistance and multiple mechanisms of triglyceride synthesis in mice lacking Dgat.", Nature Genetics May 2000, vol. 25(1), pp. 87-90.
Wu et al., "Synthesis and platelet aggregation inhibitory activities of 6-[4(4-substituted-piperazine-1-yl)phenyl]-5-methyl-4,5-dihydro-3(2H)-pyridazinone derivatives.", Database CA, Chemical Abstracts Service, XP002459096, (2000).
Zhang et al., "Synthesis and platelet aggregation inhibitory activity of pyridazinones.", Database CA, Chemical Abstracts Service, XP002459097.
Zhao et al., "Synthesis of 6-[4(4-substituted piperazyl)phenyl]-4,5-dihydro-3(2H)-pyridazinone derivatives by phase-transfer catalysis.", Database CA, Chemical Abstracts Service, XP002459095, (2000).
Farese et al., "Lipopenia and Skin Barrier Abnormalities in DGAT2-deficient Mice.", J. Biol. Chem., Mar. 19, 2004, pp. 11767-1176, vol. 279(12).
Watt, M.J., "Storing Up Trouble: Does Accumulation of Intramyocellular Triglyceride Protect Skeletal Muscle from Insulin Resistance?", Clinical and Experimental Pharmacology and Physiology, 2009, pp. 5-11, vol. 36.
Kuwabara et al., "A Nove Novel Selective Peroxisome Proliferator-Activated Receptor Agonist, 2-Methyl-c-5-[4-[5-methyl-2-(4-methylphenyl)-4-oxazolyl]butyl]-1,3-dioxane-r-2-carboxylic acid (NS-220), Potently Decreases Plasma Triglyceride and Glucose Levels and Modifies Lipoprotein Profiles in KK-Ay Mice.", J. Pharmacol. Exp. Ther., 2004, pp. 970-977, vol. 309(3).
Database Registry, Apr. 17, 2007, XP002458843.
Vippagunta et al., "Crystalline Solids.", Advanced Drug Delivery Reviews, 2001, pp. 3-26, vol. 48.
Shandala et al., "Reactions of Acetylenic Esters with Cyclic Ketones and Substituted Acetophenones.", Journal f. prakt. Chemic. Band, 1979, pp. 899-904, vol. 321(6).
Aarmadaka et al., "Synthesis and Evaluation of Urea and Thiourea Derivatives of Oxazolidinones as Antibacterial Agents.", Chem. Pharm. Bull., Feb. 1, 2007, pp. 236-240, vol. 55.
Phillips et al., "Structure-antibacterial activity of arylcarbonyl- and arylsulfonyl-piperazine 5-Triazolylmethyl oxazolidinones.", Eur.J. Med. Chem., Nov. 29, 2006, pp. 214-225, vol. 42.
Chinese J. Med. Chem., 1994, pp. 162-170, vol. 4.
RN 854989-58-5, Jul. 13, 2005.
RN 859099-41-5, Aug. 9, 2005.
RN 859135-44-7, Aug. 9, 2005.
RN 859646-88-1, Aug. 11, 2005.
RN 860081-71-6, Aug. 12, 2005.
RN 860458-98-6, Aug. 16, 2005.
RN 861994-10-7, Aug. 29, 2005.
RN 884476-57-7, May 16, 2006.
RN 892188-37-3, Jul. 12, 2006.
RN 892208-87-6, Jul. 12, 2006.
RN 892693-34-4, Jul. 28, 2006.
RN 897172-00-8, Jul. 28, 2006.
RN 897548-47-9, Jul. 31, 2006.
RN 898117-91-4, Aug. 2, 2006.
Malloy and Kane, Pathogenesis and treatment in cardiomyopathy.', Adv. Intern. Med., 2001, vol. 47, pp. 111-136.
Nikolaidis et al., "Glucagon-Like Peptide-1 Limits Myocardial Stunning following Brief Coronary Occlusion and Reperfusion in Conscious Canines.", Journal of Pharm. and Experimental Therapeutics, 2005, vol. 312(1), pp. 303-308.
Oelkers et al., "Characterizations of Two Human Genes Encoding Acyl Coenzyme A: Cholesterol Acyltransferase-related Enzymes.", J. Biol. Chem., Oct. 8, 1998, vol. 273(41), pp. 26765-26771, U.S.A.
Pearson et al., "Preparation of Functionalized P-Phenylenediamine Derivatives using Arene-Iron Chemistry.", J. of Org. Chem., 1996, vol. 61(4), pp. 1297-1305, Easton, US, XP002938137.
Perry et al., "Evidence of GLP-1-mediated neuroprotection in an animal model of pyridoxine-induced peripheral sensory neuropathy.", Experimental Neurology, 2007, vol. 203(2), pp. 293-301.
Smith et al., "Obesity resistance and multiple mechanisms of triglyceride synthesis in mice lacking Dgat.", Nature Genetics May, 2000, vol. 25(1), pp. 87-90.
Stone et al., "Lipopenia and Skin Barrier Abnormalities in DGAT2-deficient Mice.", J. Biol. Chem., Mar. 19, 2004, vol. 279(12), pp. 11767-11776.
Wu et al., "Synthesis and platelet aggregation inhibitory activities of 6-[4(4-substituted-piperazine-1-yl)phenyl]-5-methyl-4,5-dihydro3(2H)-pyridazinone derivatives.", Database CA, Chemical Abstracts Service, XP002459096 (2000).
Zhang et al., "Synthesis and platelet aggregation inhibitory activity of pyridazinones.", Database CA, Chemical Abstracts Service, XP002459097 (1994).
Zhao et al., "Synthesis of 6-[4(4-substituted piperazyl)phenyl]-4,5-dihydro-3(2H)-pyridazinone derivatives by phase-transfer catalysis.", Database CA, Chemical Abstracts Service, XP002459095 (2002).
Cao et al., "Targeting Acyl-CoA:Diacylglycerol Acyltransferase 1 (DGAT1) With Small Molecule Inhibitors for the Treatment of Metabolic Diseases.", *J. Biol. Chem.*, 2011, pp. 41838-41851, vol. 286.

\* cited by examiner

PIPERIDINE/PIPERAZINE DERIVATIVES

CROSS REFERENCE TO RELATED APPLICATIONS

This application is the U.S. national stage of Application No. PCT/EP2008/057008, filed Jun. 5, 2008, which application claims priority from EP 07109866.9, filed Jun. 8, 2007.

FIELD OF THE INVENTION

The present invention relates to the use of a DGAT inhibitor, in particular a DGAT1 inhibitor, for the manufacture of a medicament for the prevention or the treatment of a disease by elevating the levels of one or more satiety hormones, in particular GLP-1. The present invention also concerns piperidine/piperazine derivatives having DGAT inhibitory activity, in particular DGAT1 inhibitory activity. The invention further relates to methods for their preparation and pharmaceutical compositions comprising them. The invention also relates to the use of said compounds for the manufacture of a medicament for the prevention or the treatment of a disease mediated by DGAT, in particular DGAT 1.

BACKGROUND TO THE INVENTION

Triglycerides represent the major form of energy stored in eukaryotes. Disorders or imbalances in triglyceride metabolism are implicated in the pathogenesis of and increased risk for obesity, insulin resistance syndrome and type II diabetes, nonalcoholic fatty liver disease and coronary heart disease (see, Lewis, et al, *Endocrine Reviews* (2002) 23:201 and Malloy and Kane, *Adv. Intern. Med.* (2001) 47:11 1). Additionally, hypertriglyceridemia is often an adverse consequence of cancer therapy (see, Bast, et al. *Cancer Medicine*, 5th Ed., (2000) B.C. Decker, Hamilton, Ontario, CA).

A key enzyme in the synthesis of triglycerides is acyl CoA:diacylglycerol acyltransferase, or DGAT. DGAT is a microsomal enzyme that is widely expressed in mammalian tissues and that catalyzes the joining of 1,2-diacylglycerol (DAG) and fatty acyl CoA to form triglycerides (TG) at the endoplasmic reticulum (reviewed in Chen and Farese, *Trends Cardiovasc. Med.* (2000) 10: 188 and Farese, et al, *Curr. Opin. Lipidol.* (2000) 11:229). It was originally thought that DGAT uniquely controlled the catalysis of the final step of acylation of diacylglycerol to triglyceride in the two major pathways for triglyceride synthesis, the glycerol phosphate and monoacylglycerol pathways. Because triglycerides are considered essential for survival, and their synthesis was thought to occur through a single mechanism, inhibition of triglyceride synthesis through inhibiting the activity of DGAT has been largely unexplored.

Genes encoding mouse DGAT1 and the related human homologs ARGP1 (human DGAT1) and ARGP2 (human ACAT2) now have been cloned and characterized (Cases, et al, *Pro.c Nat.l Acad. Sci.* (1998) 95:13018; Oelkers, et al, *J. Biol. Chem.* (1998) 273:26765). The gene for mouse DGAT1 has been used to create DGAT knock-out mice to better elucidate the function of the DGAT gene.

Unexpectedly, mice unable to express a functional DGAT1 enzyme (Dgat1−/− mice) are viable and still able to synthesize triglycerides, indicating that multiple catalytic mechanisms contribute to triglyceride synthesis (Smith, et al, *Nature Genetics* (2000) 25:87). Other enzymes that catalyze triglyceride synthesis, for example, DGAT2 and diacylglycerol transacylase, also have been identified (Cases, et al, *J. Biol. Chem.* (2001) 276:38870). Gene knockout studies in mice have revealed that DGAT2 plays a fundamental role in mammalian triglyceride synthesis and is required for survival. DGAT2 deficient mice are lipopenic and die soon after birth, apparently from profound reductions in substrates for energy metabolism and from impaired permeability barrier function in the skin. (Farese, et al., *J. Biol. Chem.* (2004) 279: 11767).

Significantly, Dgat1−/− mice are resistant to diet-induced obesity and remain lean. Even when fed a high fat diet (21% fat) Dgat1−/− mice maintain weights comparable to mice fed a regular diet (4% fat) and have lower total body triglyceride levels. The obesity resistance in Dgat1−/− mice is not due to decreased caloric intake, but the result of increased energy expenditure and decreased resistance to insulin and leptin (Smith, et al, *Nature Genetics* (2000) 25:87; Chen and Farese, *Trends Cardiovasc. Med.* (2000) 10: 188; and Chen, et al, *J. Clin. Invest.* (2002) 109:1049). Additionally, Dgat1−/− mice have reduced rates of triglyceride absorption (Buhman, et al, *J. Biol. Chem.* (2002) 277:25474). In addition to improved triglyceride metabolism, Dgat1−/− mice also have improved glucose metabolism, with lower glucose and insulin levels following a glucose load, in comparison to wild-type mice (Chen and Farese, *Trends Cardiovasc. Med.* (2000) 10: 188).

The finding that multiple enzymes contribute to catalyzing the synthesis of triglyceride from diacylglycerol is significant, because it presents the opportunity to modulate one catalytic mechanism of this biochemical reaction to achieve therapeutic results in an individual with minimal adverse side effects. Compounds that inhibit the conversion of diacylglycerol to triglyceride, for instance by specifically inhibiting the activity of DGAT1, will find use in lowering corporeal concentrations and absorption of triglycerides to therapeutically counteract the pathogenic effects caused by abnormal metabolism of triglycerides in obesity, insulin resistance syndrome and overt type II diabetes, congestive heart failure and atherosclerosis, and as a consequence of cancer therapy.

Because of the ever increasing prevalence of obesity, type II diabetes, heart disease and cancer in societies throughout the world, there is a pressing need in developing new therapies to effectively treat and prevent these diseases. Therefore there is an interest in developing compounds that can potently and specifically inhibit the catalytic activity of DGAT, in particular DGAT1.

We have now unexpectedly found that the compounds of the present invention exhibit DGAT inhibitory activity, in particular DGAT1 inhibitory activity, and can therefore be used to prevent or treat a disease associated with or mediated by DGAT, such as for example obesity, type II diabetes, heart disease and cancer. The compounds of the invention differ from the prior art compounds in structure, in their pharmacological activity, pharmacological potency, and/or pharmacological profile.

We have also unexpectedly found that DGAT inhibitors can be used to elevate the levels of one or more satiety hormones, in particular glucagon-like-peptide-1 (GLP-1) and therefore DGAT inhibitors, in particular DGAT1 inhibitors, can also be used to prevent or treat a disease which can benefit from elevated levels of a satiety hormone, in particular GLP-1. Glucagon-like peptide 1 (GLP-1) is an intestinal hormone which generally stimulates insulin secretion during hyperglycemia, suppresses glucagon secretion, stimulates (pro) insulin biosynthesis and decelerates gastric emptying and acid secretion. GLP-1 is secreted from L cells in the small and large bowel following the ingestion of fat and proteins. GLP-1 has been suggested, among other indications, as a possible therapeutic agent for the management of type 2 non-insulin-dependent diabetes mellitus as well as related metabolic disorders, such as obesity.

Thus, by the present finding, a disease which can benefit from elevated levels of GLP-1 can be treated with small molecules (compared to large molecules such as proteins or protein-like compounds, e.g. GLP-1 analogues).

BACKGROUND PRIOR ART

WO 2006/034441 discloses heterocyclic derivatives and their use as stearoyl CoA desaturase inhibitors (SCD-1 inhibitors).

WO 2006/086445 relates to a combination therapy of a SCD-1 inhibitor and another drug to treat adverse weight gain.

WO 2006/004200 and JP2007131584 relate to urea and amino derivatives having DGAT inhibitory activity.

WO 2004/047755 relates to fused bicyclic nitrogen-containing heterocycles having DGAT inhibitory activity.

WO2005/072740 relates to an anorectic action of a compound having DGAT inhibitory activity.

DESCRIPTION OF THE INVENTION

The present invention relates to the use of a DGAT inhibitor for the manufacture of a medicament for the prevention or the treatment, in particular for the treatment, of a disease which can benefit from elevated levels of one or more satiety hormones, in particular GLP-1.

The present invention further relates to a compound of formula

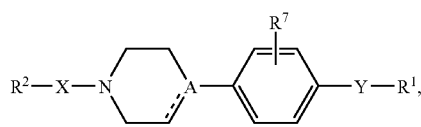

including any stereochemically isomeric form thereof, wherein

A represents CH or N;

the dotted line represents an optional bond in case A represents a carbon atom;

X represents —O—C(=O)—; —C(=O)—C(=O)—; —NR$^x$—C(=O)—; —Z—C(=O)—; —Z—NR$^x$—C(=O)—; —C(=O)—Z—; —NR$^x$—C(=O)—Z—; —C(=S)—; —NR$^x$—C(=S)—; —Z—C(=S)—; —Z—NR$^x$—C(=S)—; —C(=S)—Z—; —NR$^x$—C(=S)—Z—;

Z represents a bivalent radical selected from $C_{1-6}$alkanediyl, $C_{2-6}$alkenediyl or $C_{2-6}$alkynediyl; wherein each of said $C_{1-6}$alkanediyl, $C_{2-6}$alkynediyl or $C_{2-6}$alkynediyl may optionally be substituted with hydroxyl or amino; and wherein two hydrogen atoms attached to the same carbon atom in $C_{1-6}$alkanediyl may optionally be replaced by $C_{1-6}$alkanediyl;

R$^x$ represents hydrogen or $C_{1-4}$alkyl;

Y represents —C(=O)—NR$^x$— or —NR$^x$—C(=O)—;

R$^1$ represents adamantanyl, $C_{3-6}$cycloalkyl; aryl$^1$ or Het$^1$;

R$^2$ represents $C_{3-6}$cycloalkyl, phenyl, naphtalenyl, 2,3-dihydro-1,4-benzodioxinyl, 1,3-benzodioxolyl, 2,3-dihydrobenzofuranyl or a 6-membered aromatic heterocycle containing 1 or 2 N atoms, wherein said $C_{3-6}$cycloalkyl, phenyl, naphtalenyl, 2,3-dihydro-1,4-benzodioxinyl, 1,3-benzodioxolyl or a 6-membered aromatic heterocycle containing 1 or 2 N atoms may optionally be substituted with at least one substituent, in particular one, two, three, four or five substituents, each substituent independently selected from hydroxyl; carboxyl; halo; $C_{1-6}$alkyl optionally substituted with hydroxy; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxycarbonyl wherein $C_{1-6}$alkyl may optionally be substituted with aryl; cyano; $C_{1-6}$alkylcarbonyl; nitro; amino; mono- or di($C_{1-4}$alkyl)amino; $C_{1-4}$alkylcarbonylamino; —S(=O)$_p$—$C_{1-4}$alkyl; R$^4$R$^3$N—C(=O)—; R$^4$R$^3$N—$C_{1-6}$alkyl; $C_{3-6}$cycloalkyl; $C_{3-6}$cycloalkyl$C_{1-4}$alkyl; $C_{3-6}$cycloalkyl-C(=O)—; aryl; aryloxy; arylC$_{1-4}$alkyl; aryl-C(=O)—$C_{1-4}$alkyl; aryl-C(=O)—; Het; HetC$_{1-4}$alkyl; Het-C(=O)—$C_{1-4}$alkyl; Het-C(=O)—; Het-O—;

R$^3$ represents hydrogen; $C_{1-4}$alkyl optionally substituted with hydroxyl or $C_{1-4}$alkyloxy;

R$^6$R$^5$N—$C_{1-4}$alkyl; $C_{1-4}$alkyloxy; Het; Het-$C_{1-4}$alkyl; aryl; R$^6$R$^5$N—C(=O)—$C_{1-4}$alkyl;

R$^4$ represents hydrogen or $C_{1-4}$alkyl;

R$^5$ represents hydrogen; $C_{1-4}$alkyl; $C_{1-4}$alkylcarbonyl;

R$^6$ represents hydrogen or $C_{1-4}$alkyl; or

R$^5$ and R$^6$ may be taken together with the nitrogen to which they are attached to form a saturated monocyclic 5, 6 or 7-membered heterocycle which may further contain one or more heteroatoms each independently selected from O, S, S(=O)$_p$ or N; and which heterocycle may optionally be substituted with $C_{1-4}$alkyl;

R$^7$ represents hydrogen, halo, $C_{1-4}$alkyl, $C_{1-4}$alkyl substituted with hydroxyl;

aryl represents phenyl or phenyl substituted with at least one substituent, in particular one, two, three, four or five substituents, each substituent independently being selected from hydroxyl; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; amino carbonyl; mono- or di($C_{1-4}$alkyl)aminocarbonyl; $C_{1-6}$alkylcarbonyl; nitro; amino; mono- or di($C_{1-4}$alkyl)amino; —S(=O)$_p$—$C_{1-4}$alkyl;

aryl$^1$ represents phenyl, naphthalenyl or fluorenyl; each of said phenyl, naphthalenyl or fluorenyl optionally substituted with at least one substituent, in particular one, two, three, four or five substituents, each substituent independently being selected from hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; nitro; amino; mono- or di($C_{1-6}$alkyl)amino; R$^4$R$^3$N—$C_{1-6}$alkyl; $C_{3-6}$cycloalkyl-NR$^x$—; aryl-NR$^x$—; Het-NR$^x$—; $C_{3-6}$cycloalkylC$_{1-4}$alkyl-NR$^x$—; arylC$_{1-4}$alkyl-NR$^x$—; HetC$_{1-4}$alkyl-NR$^x$—; —S(=O)$_p$—$C_{1-4}$alkyl; $C_{3-6}$cycloalkyl; $C_{3-6}$cycloalkylC$_{1-4}$ alkyl; $C_{3-6}$cycloalkyl-C(=O)—; aryl; aryloxy; arylC$_{1-4}$ alkyl; aryl-C(=O)—$C_{1-4}$alkyl; aryl-C(=O)—; Het; HetC$_{1-4}$alkyl; Het-C(=O)—$C_{1-4}$alkyl; Het-C(=O)—; Het-O—;

Het represents a monocyclic non-aromatic or aromatic heterocycle containing at least one heteroatom each independently selected from O, S, S(=O)$_p$ or N; or a bicyclic or tricyclic non-aromatic or aromatic heterocycle containing at least one heteroatom each independently selected from O, S, S(=O)$_p$ or N; said monocyclic heterocycle or said bi- or tricyclic heterocycle optionally being substituted with at least one substituent, in particular one, two, three, four or five substituents, each substituent independently being selected from hydroxyl; oxo; carboxyl; halo; C$_{1-6}$alkyl optionally substituted with C$_{1-4}$alkyloxy, amino or mono- or di(C$_{1-4}$alkyl)amino; polyhaloC$_{1-6}$alkyl; C$_{1-6}$alkyloxy optionally substituted with C$_{1-4}$alkyloxy; C$_{1-6}$alkylthio; polyhaloC$_{1-6}$alkyloxy; C$_{1-6}$alkyloxycarbonyl; cyano; aminocarbonyl; mono- or di(C$_{1-4}$alkyl)aminocarbonyl; C$_{1-6}$alkylcarbonyl; nitro; amino; mono- or di(C$_{1-4}$alkyl)amino; —S(=O)$_p$—C$_{1-4}$alkyl;

Het$^1$ represents a monocyclic non-aromatic or aromatic heterocycle containing at least one heteroatom each independently selected from O, S, S(=O)$_p$ or N; or a bicyclic or tricyclic non-aromatic or aromatic heterocycle containing at least one heteroatom each independently selected from O, S, S(=O)$_p$ or N; said monocyclic heterocycle or said bi- or tricyclic heterocycle optionally being substituted with at least one substituent, in particular one, two, three, four or five substituents, each substituent independently being selected from hydroxyl; oxo; carboxyl; halo; C$_{1-6}$alkyl optionally substituted with aryl-C(=O)—; hydroxyC$_{1-6}$ alkyl optionally substituted with aryl or aryl-C(=O)—; polyhaloC$_{1-6}$alkyl; C$_{1-6}$alkyloxy optionally substituted with C$_{1-4}$alkyloxy; C$_{1-6}$alkylthio; polyhaloC$_{1-6}$alkyloxy; C$_{1-6}$alkyloxy-carbonyl wherein C$_{1-6}$alkyl may optionally be substituted with aryl; cyano; aminocarbonyl; mono- or di(C$_{1-4}$alkyl)aminocarbonyl; C$_{1-6}$alkylcarbonyl; nitro; amino; mono- or di(C$_{1-6}$alkyl)amino; R$^4$R$^3$N—C$_{1-6}$alkyl C$_{3-6}$cycloalkyl-NR$^x$—; aryl-NR$^x$—; Het-NR$^x$—; C$_{3-6}$cycloalkylC$_{1-4}$alkyl-NR$^x$—; arylC$_{1-4}$alkyl-NR$^x$—; HetC$_{1-4}$alkyl-NR$^x$—; —S(=O)$_p$—C$_{1-4}$alkyl; C$_{3-6}$cycloalkyl; C$_{3-6}$cycloalkylC$_{1-4}$alkyl; C$_{3-6}$cycloalkyl-C(=O)—; aryl; aryloxy; arylC$_{1-4}$alkyl; aryl-C(=O)—C$_{1-4}$alkyl; aryl-C(=O)—; Het; HetC$_{1-4}$alkyl; Het-C(=O)—C$_{1-4}$ alkyl; Het-C(=O)—; Het-O—;

p represents 1 or 2;
provided that the following compounds

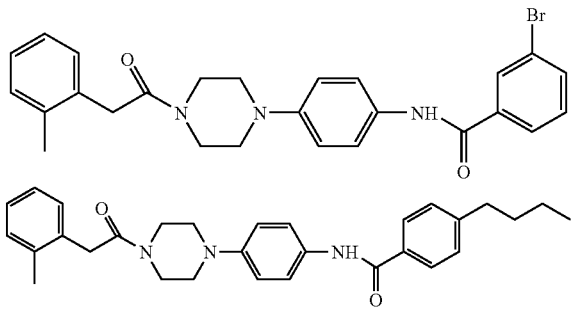

are excluded;
a N-oxide thereof, a pharmaceutically acceptable salt thereof or a solvate thereof.

The present invention further relates to the use of a compound of formula (I''') for the manufacture of a medicament for the prevention or the treatment of a disease mediated by DGAT, in particular the present invention relates to the use of a compound of formula (I''') for the manufacture of a medicament for the prevention or the treatment of a disease which can benefit from inhibition of DGAT, in particular for the treatment of a disease which can benefit from inhibition of DGAT, in particular DGAT1, wherein the compound of formula (I''') is a compound of formula

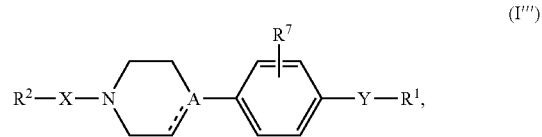

including any stereochemically isomeric form thereof, wherein

A represents CH or N;
the dotted line represents an optional bond in case A represents a carbon atom;
X represents —O—C(=O)—; —C(=O)—C(=O)—; —NR$^x$—C(=O)—; —Z—C(=O)—; —Z—NR$^x$—C(=O)—; —C(=O)—Z—; —NR$^x$—C(=O)—Z—; —C(=S)—; —S(=O)$_p$—; —NR$^x$—C(=S)—; —Z—C(=S)—; —Z—NR$^x$—C(=S)—; —C(=S)—Z—; —NR$^x$—C(=S)—Z—;
Z represents a bivalent radical selected from C$_{1-6}$alkanediyl, C$_{2-6}$alkynediyl or C$_{2-6}$alkynediyl; wherein each of said C$_{1-6}$alkanediyl, C$_{2-6}$alkynediyl or C$_{2-6}$alkynediyl may optionally be substituted with hydroxyl or amino; and wherein two hydrogen atoms attached to the same carbon atom in C$_{1-6}$alkanediyl may optionally be replaced by C$_{1-6}$alkanediyl;
R$^x$ represents hydrogen or C$_{1-4}$alkyl;
Y represents —C(=O)—NR$^x$— or —NR$^x$—C(=O)—;
R$^1$ represents adamantanyl, C$_{3-6}$cycloalkyl; aryl$^1$ or Het$^1$;
R$^2$ represents hydrogen, C$_{1-6}$alkyl, C$_{2-6}$alkenyl, C$_{3-6}$cycloalkyl, phenyl, naphtalenyl, 2,3-dihydro-1,4-benzodioxinyl, 1,3-benzodioxolyl, 2,3-dihydrobenzo furanyl or a 6-membered aromatic heterocycle containing 1 or 2 N atoms, wherein said C$_{3-6}$cycloalkyl, phenyl, naphtalenyl, 2,3-dihydro-1,4-benzodioxinyl, 1,3-benzodioxolyl or 6-membered aromatic heterocycle containing 1 or 2 N atoms may optionally be substituted with at least one substituent, in particular one, two, three, four or five substituents, each substituent independently selected from hydroxyl; carboxyl; halo; C$_{1-6}$alkyl optionally substituted with hydroxy; polyhaloC$_{1-6}$alkyl; C$_{1-6}$alkyloxy optionally substituted with C$_{1-4}$alkyloxy; C$_{1-6}$alkylthio; polyhaloC$_{1-6}$ alkyloxy; C$_{1-6}$alkyloxycarbonyl wherein C$_{1-6}$alkyl may optionally be substituted with aryl; cyano; C$_{1-6}$alkylcarbonyl; nitro; amino; mono- or di(C$_{1-4}$alkyl)amino; C$_{1-4}$alkylcarbonylamino; —S(=O)$_p$—C$_{1-4}$alkyl; R$^4$R$^3$N—C(=O)—; R$^4$R$^3$N—C$_{1-6}$alkyl; C$_{3-6}$cycloalkyl; C$_{3-6}$cycloalkylC$_{1-4}$alkyl; C$_{3-6}$cycloalkyl-C(=O)—; aryl; aryloxy; arylC$_{1-4}$alkyl; aryl-C(=O)—C$_{1-4}$alkyl; aryl-C(=O)—; Het; HetC$_{1-4}$alkyl; Het-C(=O)—C$_{1-4}$alkyl; Het-C(=O)—; Het-O—;
R$^3$ represents hydrogen; C$_{1-4}$alkyl optionally substituted with hydroxyl or C$_{1-4}$alkyloxy; R$^6$R$^5$N—C$_{1-4}$alkyl; C$_{1-4}$alkyloxy; Het; Het-C$_{1-4}$alkyl; aryl; R$^6$R$^5$N—C(=O)—C$_{1-4}$alkyl;
R$^4$ represents hydrogen or C$_{1-4}$alkyl;
R$^5$ represents hydrogen; C$_{1-4}$alkyl; C$_{1-4}$alkylcarbonyl;
R$^6$ represents hydrogen or C$_{1-4}$alkyl; or
R$^5$ and R$^6$ may be taken together with the nitrogen to which they are attached to form a saturated monocyclic 5, 6 or 7-membered heterocycle which may further contain one or more heteroatoms each independently selected from O, S, S(=O)$_p$ or N; and which heterocycle may optionally be substituted with C$_{1-4}$alkyl;

$R^7$ represents hydrogen, halo, $C_{1-4}$alkyl, $C_{1-4}$alkyl substituted with hydroxyl;

aryl represents phenyl or phenyl substituted with at least one substituent, in particular one, two, three, four or five substituents, each substituent independently being selected from hydroxyl; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; amino carbonyl; mono- or di($C_{1-4}$alkyl)aminocarbonyl; $C_{1-6}$alkylcarbonyl; nitro; amino; mono- or di($C_{1-4}$alkyl)amino; —S(=O)$_p$—$C_{1-4}$alkyl;

aryl$^1$ represents phenyl, naphthalenyl or fluorenyl; each of said phenyl, naphthalenyl or fluorenyl optionally substituted with at least one substituent, in particular one, two, three, four or five substituents, each substituent independently being selected from hydroxyl; oxo; carboxyl; halo; $C_{1-6}$alkyl optionally substituted with carboxyl, $C_{1-4}$alkyloxycarbonyl or aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; nitro; amino; mono- or di($C_{1-6}$alkyl)amino; $R^4R^3N$—$C_{1-6}$alkyl; $C_{3-6}$cycloalkyl-NR$^x$—; aryl-NR$^x$—; Het-NR$^x$—; $C_{3-6}$cycloalkyl$C_{1-4}$alkyl-NR$^x$—; aryl$C_{1-4}$alkyl-NR$^x$—; Het$C_{1-4}$ alkyl-NR$^x$—; —S(=O)$_p$—$C_{1-4}$alkyl; $C_{3-6}$cycloalkyl; $C_{3-6}$cycloalkyl$C_{1-4}$ alkyl; $C_{3-6}$cycloalkyl-C(=O)—; aryl; aryloxy; aryl$C_{1-4}$ alkyl; aryl-C(=O)—$C_{1-4}$alkyl; aryl-C(=O)—; Het; Het$C_{1-4}$alkyl; Het-C(=O)—$C_{1-4}$alkyl; Het-C(=O)—; Het-O—;

Het represents a monocyclic non-aromatic or aromatic heterocycle containing at least one heteroatom each independently selected from O, S, S(=O)$_p$ or N; or a bicyclic or tricyclic non-aromatic or aromatic heterocycle containing at least one heteroatom each independently selected from O, S, S(=O)$_p$ or N; said monocyclic heterocycle or said bi- or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; —S(=O)$_p$—$C_{1-4}$alkyl;

Het$^1$ represents a monocyclic non-aromatic or aromatic heterocycle containing at least one heteroatom each independently selected from O, S, S(=O)$_p$ or N; or a bicyclic or tricyclic non-aromatic or aromatic heterocycle containing at least one heteroatom each independently selected from O, S, S(=O)$_p$ or N; said monocyclic heterocycle or said bi- or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; nitro; amino; mono- or di($C_{1-6}$alkyl)amino; $R^4R^3N$—$C_{1-6}$alkyl; $C_{3-6}$cycloalkyl-NR$^x$—; aryl-NR$^x$—; Het-NR$^x$—; $C_{3-6}$cycloalkyl$C_{1-4}$alkyl-NR$^x$—; aryl$C_{1-4}$alkyl-NR$^x$—; Het$C_{1-4}$ alkyl-NR$^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—$C_{1-4}$alkyl; aryl-C(=O)—; Het; Het$C_{1-4}$alkyl; Het-C(=O)—$C_{1-4}$ alkyl; Het-C(=O)—; Het-O—;

p represents 1 or 2;

a N-oxide thereof, a pharmaceutically acceptable salt thereof or a solvate thereof.

The present invention also relates to the use of a compound of formula (I) for the manufacture of a medicament for the prevention or the treatment of a disease mediated by DGAT, in particular the present invention relates to the use of a compound of formula (I) for the manufacture of a medicament for the prevention or the treatment of a disease which can benefit from inhibition of DGAT, in particular for the treatment of a disease which can benefit from inhibition of DGAT, in particular DGAT1.

The present invention also relates to the use of a compound of formula (I) or (I''') for the manufacture of a medicament for the prevention or the treatment of a disease which can benefit from elevated levels of one or more satiety hormones, in particular GLP-1, in particular the present invention relates to the use of a compound of formula (I) or (I''') for the manufacture of a medicament for the treatment of a disease which can benefit from elevated levels of GLP-1.

As used hereinbefore or hereinafter $C_{0-3}$alkyl as a group or part of a group defines straight or branched chain saturated hydrocarbon radicals having from 0 (then it represents a direct bond) to 3 carbon atoms such as methyl, ethyl, propyl, 1-methyl-ethyl; $C_{1-2}$alkyl as a group or part of a group defines straight or branched chain saturated hydrocarbon radicals having 1 or 2 carbon atoms such as methyl, ethyl; $C_{1-4}$alkyl as a group or part of a group defines straight or branched chain saturated hydrocarbon radicals having from 1 to 4 carbon atoms such as methyl, ethyl, propyl, 1-methylethyl, butyl; $C_{1-5}$alkyl as a group or part of a group defines straight or branched chain saturated hydrocarbon radicals having from 1 to 5 carbon atoms such as the group defined for $C_{1-4}$alkyl and pentyl, 2-methylbutyl and the like; $C_{1-6}$alkyl as a group or part of a group defines straight or branched chain saturated hydrocarbon radicals having from 1 to 6 carbon atoms such as the group defined for $C_{1-4}$alkyl and for $C_{1-5}$alkyl and hexyl, 2-methylpentyl and the like; $C_{1-6}$alkanediyl defines straight or branched chain saturated bivalent hydrocarbon radicals having from 1 to 6 carbon atoms such as methylene, 1,2-ethanediyl or 1,2-ethylidene, 1,3-propanediyl or 1,3-propylidene, 1,4-butanediyl or 1,4-butylidene, 1,5-pentanediyl and the like; $C_{2-6}$alkenyl as a group or part of a group defines straight or branched chain hydrocarbon radicals having from 2 to 6 carbon atoms and having a double bond such as ethenyl, propenyl, butenyl, pentenyl, hexenyl, 3-methylbutenyl and the like; $C_{2-6}$alkynediyl defines straight or branched chain bivalent hydrocarbon radicals having from 2 to 6 carbon atoms and having a double bond such as 1,2-ethenediyl, 1,3-propenediyl, 1,4-butenediyl, 1,5-pentenediyl and the like; $C_{2-6}$alkynediyl as a group or part of a group defines straight or branched chain bivalent hydrocarbon radicals having from 2 to 6 carbon atoms and having a triple bond such as 1,2-ethynediyl, 1,3-propynediyl, 1,4-butynediyl, 1,5-pentynediyl and the like; $C_{3-6}$cycloalkyl is generic to cyclopropyl, cyclobutyl, cyclopentyl and cyclohexyl.

The term halo is generic to fluoro, chloro, bromo and iodo. As used hereinbefore or hereinafter, polyhalo$C_{1-6}$alkyl as a group or part of a group is defined as $C_{1-6}$alkyl substituted with one or more, such as for example 2, 3, 4 or 5 halo atoms, for example methyl substituted with one or more fluoro atoms, for example, difluoromethyl or trifluoromethyl, 1,1-difluoro-ethyl, 1,1-difluoro-2,2,2-trifluoro-ethyl and the like. In case more than one halogen atoms are attached to a $C_{1-6}$alkyl group within the definition of polyhalo$C_{1-6}$alkyl, they may be the same or different.

As used herein before, the term (=O) forms a carbonyl moiety when attached to a carbon atom, a sulfoxide moiety when attached to a sulfur atom and a sulfonyl moiety when two of said terms are attached to a sulfur atom. Oxo means =O.

The radical Het or Het$^1$ as defined hereinabove may be an optionally substituted monocyclic non-aromatic or aromatic heterocycle containing at least one heteroatom, in particular 1, 2 or 3 heteroatoms, each independently selected from O, S, S(=O)$_p$ or N; or an optionally substituted bi- or tricyclic non-aromatic or aromatic heterocycle containing at least one heteroatom, in particular 1, 2, 3, 4 or 5 heteroatoms, each independently selected from O, S, S(=O)$_p$ or N. Examples of such unsubstituted monocyclic heterocycles comprise, but are not limited to, non-aromatic (fully saturated or partially saturated) or aromatic 4-, 5-, 6- or 7-membered monocyclic heterocycles such as for example azetidinyl, tetrahydrofuranyl, pyrrolidinyl, dioxolanyl, imidazolidinyl, thiazolidinyl, tetrahydrothienyl, dihydrooxazolyl, isothiazolidinyl, isoxazolidinyl, oxadiazolidinyl, triazolidinyl, thiadiazolidinyl, pyrazolidinyl, piperidinyl, hexahydropyrimidinyl, hexahydropyrazinyl, dioxanyl, morpholinyl, dithianyl, thiomorpholinyl, piperazinyl, trithianyl, hexahydrodiazepinyl, pyrrolinyl, imidazolinyl, pyrazolinyl, pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl and the like. Examples of such unsubstituted bicyclic or tricyclic heterocycles comprise, but are not limited to, non-aromatic (fully saturated or partially saturated) or aromatic 8- to 17-membered bicyclic or tricyclic heterocycles such as for example decahydroquinolinyl, octahydroindolyl, 2,3-dihydrobenzo furanyl, 1,3-benzodioxolyl, 2,3-dihydro-1,4-benzodioxinyl, indolinyl, benzofuryl, isobenzofuryl, benzothienyl, isobenzothienyl, indolizinyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, cinnolinyl, quinolizinyl, phthalazinyl, quinoxalinyl, quinazolinyl, naphthiridinyl, pteridinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, imidazooxazolyl, imidazothiazolyl, imidazoimidazolyl, imidazopyrazolyl; isoxazolotriazinyl, isothiazolotriazinyl, pyrazolotriazinyl, oxazolotriazinyl, thiazolotriazinyl, imidazotriazinyl, oxadiazolotriazinyl, thiadiazolotriazinyl, triazolotriazinyl, carbazolyl, acridinyl, phenazinyl, phenothiazinyl, phenoxazinyl and the like. Optional substituents for Het heterocycles are hydroxyl; oxo; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyl-oxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; —S(=O)$_p$—$C_{1-4}$alkyl. Optional substituents for Het$^1$ substituents are hydroxyl; oxo; carboxyl; halo; $C_{1-6}$alkyl optionally substituted with aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-4}$ alkyl)aminocarbonyl; $C_{1-6}$alkylcarbonyl; nitro; amino; mono- or di($C_{1-6}$alkyl)amino; $R^4R^3N$—$C_{1-6}$alkyl $C_{3-6}$cycloalkyl-$NR^x$—; aryl-$NR^x$—; Het-$NR^x$—; $C_{3-6}$-cycloalkyl$C_{1-4}$alkyl-$NR^x$—; aryl$C_{1-4}$alkyl-$NR^x$—; Het$C_{1-4}$alkyl-$NR^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—$C_{1-4}$alkyl; aryl-C(=O)—; Het; Het$C_{1-4}$alkyl; Het-C(=O)—$C_{1-4}$alkyl; Het-C(=O)—; Het-O—.

Examples of a 6-membered aromatic heterocycle containing 1 or 2 N atoms in the definition of $R^2$ are pyridyl, pyrimidinyl, pyridazinyl, pyrazinyl.

When any variable occurs more than one time in any constituent (e.g. aryl, Het), each definition is independent.

The term Het or Het$^1$ is meant to include all the possible isomeric forms of the heterocycles, for instance, pyrrolyl comprises 1H-pyrrolyl and 2H-pyrrolyl.

The carbocycles or heterocycles covered by for instance the terms aryl, aryl$^1$, Het, Het$^1$ or $R^3$ may be attached to the remainder of the molecule of formula (I) through any ring carbon or heteroatom as appropriate, if not otherwise specified. Thus, for example, when the heterocycle is imidazolyl, it may be 1-imidazolyl, 2-imidazolyl, 4-imidazolyl and the like, or when the carbocycle is naphthalenyl, it may be 1-naphthalenyl, 2-naphthalenyl and the like.

Lines drawn from substituents into ring systems indicate that the bond may be attached to any of the suitable ring atoms.

When X is defined as for instance —$NR^x$—C(=O)—, this means that the nitrogen of $NR^x$ is linked to the $R^2$ substituent and the carbon atom of C(=O) is linked to the nitrogen of the ring

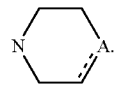

Thus the left part of the bivalent radical in the definition of X is linked to the $R^2$ substituent and the right part of the bivalent radical in the definition of X is linked to the ring moiety

Some of the compounds of formula (I) may also exist in their tautomeric form. Such forms although not explicitly indicated in the above formula are intended to be included within the scope of the present invention.

Whenever used hereinbefore or hereinafter that substituents can be selected each independently out of a list of numerous definitions, such as for example for $R^3$ and $R^4$, all possible combinations are intended which are chemically possible.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable salts as mentioned hereinbefore or hereinafter are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxy-acetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfonic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. The pharmaceutically acceptable salts as mentioned hereinbefore or hereinafter are meant to also comprise the therapeutically active non-toxic metal or amine addition salt forms (base addition salt forms) which the compounds of formula (I) are able to form. Appropriate base addition salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquino line, the benzathine, N-methyl-D-glucamine, 2-amino-2-(hydroxymethyl)-1,3-propanediol, hydrabamine salts, and salts with amino acids such as, for example, arginine, lysine and the like.

Conversely the salt form can be converted by treatment with acid into the free acid form.

The term salt also comprises the quaternary ammonium salts (quaternary amines) which the compounds of formula (I) are able to form by reaction between a basic nitrogen of a compound of formula (I) and an appropriate quaternizing agent, such as, for example, an optionally substituted $C_{1-6}$alkylhalide, arylhalide, $C_{1-6}$alkyl-carbonylhalide, aryl-carbonylhalide, or aryl$C_{1-6}$alkylhalide, e.g. methyliodide or benzyliodide. Other reactants with good leaving groups may also be used, such as for example $C_{1-6}$alkyl trifluoromethanesulfonates, $C_{1-6}$alkyl methanesulfonates, and $C_{1-6}$alkyl p-toluenesulfonates. A quaternary amine has a positively charged nitrogen. Pharmaceutically acceptable counterions include chloro, bromo, iodo, trifluoroacetate, acetate, triflate, sulfate, sulfonate. The counterion of choice can be introduced using ion exchange resins.

The term solvate comprises the hydrates and solvent addition forms which the compounds of formula (I) are able to form, as well as the salts thereof. Examples of such forms are e.g. hydrates, alcoholates and the like.

The N-oxide forms of the present compounds are meant to comprise the compounds of formula (I) wherein one or several tertiary nitrogen atoms are oxidized to the so-called N-oxide.

It will be appreciated that some of the compounds of formula (I) and their N-oxides, salts, and solvates may contain one or more centers of chirality and exist as stereochemically isomeric forms.

The term "stereochemically isomeric forms" as used hereinbefore or hereinafter defines all the possible stereoisomeric forms which the compounds of formula (I), and their N-oxides, salts, or solvates may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their N-oxides, salts or solvates, substantially free, i.e. associated with less than 10%, preferably less than 5%, in particular less than 2% and most preferably less than 1% of the other isomers. Thus, when a compound of formula (I) is for instance specified as (E), this means that the compound is substantially free of the (Z) isomer.

In particular, stereogenic centers may have the R- or S-configuration; substituents on bivalent cyclic (partially) saturated radicals may have either the cis- or trans-configuration. Compounds encompassing double bonds can have an E (entgegen) or Z (zusammen)-stereochemistry at said double bond. The terms cis, trans, R, S, E and Z are well known to a person skilled in the art.

Stereochemically isomeric forms of the compounds of formula (I) are obviously intended to be embraced within the scope of this invention.

Following CAS-nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where the first R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S—[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system relative to the position of the highest priority substituent on the reference atom is denominated "α", if it is on the same side of the mean plane determined by the ring system, or "β", if it is on the other side of the mean plane determined by the ring system.

The compounds of (I) may be synthesized in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

Whenever used hereinafter, the term "compounds of formula (I)" or any subgroup thereof, is meant to also include their N-oxide forms, their salts, their stereochemically isomeric forms and their solvates. Of special interest are those compounds of formula (I) which are stereochemically pure.

A first embodiment of the present invention are those compounds of formula (I) having the following formula

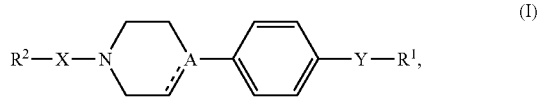

(I)

including any stereochemically isomeric form thereof, wherein

A represents CH or N;
the dotted line represents an optional bond in case A represents a carbon atom;
X represents —NR$^x$—C(=O)—; —Z—C(=O)—; —Z—NR$^x$—C(=O)—; —C(=O)—Z—; —NR$^x$—C(=O)—Z—; —C(=S)—; —NR$^x$—C(=S)—; —Z—C(=S)—; —Z—NR$^x$—C(=S)—; —C(=S)—Z—; —NR$^x$—C(=S)—Z—;
Z represents a bivalent radical selected from $C_{1-6}$alkanediyl, $C_{2-6}$alkynediyl or $C_{2-6}$alkynediyl; wherein each of said $C_{1-6}$alkanediyl, $C_{2-6}$alkynediyl or $C_{2-6}$alkynediyl may optionally be substituted with hydroxyl;
R$^x$ represents hydrogen or $C_{1-4}$alkyl;
Y represents —C(=O)—NR$^x$— or —NR$^x$—C(=O)—;
R$^1$ represents $C_{3-6}$cycloalkyl; aryl$^1$ or Het$^1$;
R$^2$ represents $C_{3-6}$cycloalkyl, phenyl, naphtalenyl, 2,3-dihydro-1,4-benzodioxinyl, 1,3-benzodioxolyl, wherein said $C_{3-6}$cycloalkyl, phenyl, naphtalenyl, 2,3-dihydro-1,4-benzodioxinyl, 1,3-benzodioxolyl may optionally be substituted with at least one substituent, in particular one, two, three, four or five substituents, each substituent independently selected from hydroxyl; carboxyl; halo; $C_{1-6}$alkyl optionally substituted with hydroxy; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxycarbonyl wherein $C_{1-6}$alkyl may optionally be substituted with aryl; cyano; $C_{1-6}$alkylcarbonyl; nitro; amino; mono- or di($C_{1-4}$alkyl)amino; —S(=O)$_p$—$C_{1-4}$alkyl; R$^4$R$^3$N—C(=O)—; R$^4$R$^3$N—$C_{1-6}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; Het; HetC$_{1-4}$alkyl; Het-C(=O)—; Het-O—;
R$^3$ represents hydrogen; $C_{1-4}$alkyl optionally substituted with hydroxyl or $C_{1-4}$alkyloxy; R$^6$R$^5$N—$C_{1-4}$alkyl; $C_{1-4}$alkyloxy; Het; aryl; R$^6$R$^5$N—C(=O)—$C_{1-4}$alkyl;
R$^4$ represents hydrogen or $C_{1-4}$alkyl;
R$^5$ represents hydrogen; $C_{1-4}$alkyl; $C_{1-4}$alkylcarbonyl;
R$^6$ represents hydrogen or $C_{1-4}$alkyl; or
R$^5$ and R$^6$ may be taken together with the nitrogen to which they are attached to form a saturated monocyclic 5, 6 or 7-membered heterocycle which may further contain one or more heteroatoms selected from O, S, S(=O)$_p$ or N; and which heterocycle may optionally be substituted with $C_{1-4}$alkyl;
aryl represents phenyl or phenyl substituted with at least one substituent, in particular one, two, three, four or five substituents, each substituent independently being selected from hydroxyl; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; —S(=O)$_p$—$C_{1-4}$alkyl;
aryl$^1$ represents phenyl, naphthalenyl or fluorenyl; each of said phenyl, naphthalenyl or fluorenyl optionally substituted with at least one substituent, in particular one, two, three, four or five substituents, each substituent independently being selected from hydroxyl; oxo; carboxyl; halo; $C_{1-6}$alkyl optionally substituted with aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; nitro; amino; mono- or di($C_{1-6}$alkyl)amino; $C_{3-6}$cycloalkyl-NR$^x$—; aryl-NR$^x$—; Het-NR$^x$—; $C_{3-6}$cycloalkyl$C_{1-4}$alkyl-NR$^x$—; aryl$C_{1-4}$alkyl-NR$^x$—; HetC$_{1-4}$alkyl-NR$^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; Het; HetC$_{1-4}$alkyl; Het-C(=O)—; Het-O—;
Het represents a monocyclic non-aromatic or aromatic heterocycle containing at least one heteroatom selected from O, S, S(=O)$_p$ or N; or a bicyclic or tricyclic non-aromatic or aromatic heterocycle containing at least one heteroatom selected from O, S, S(=O)$_p$ or N; said monocyclic heterocycle or said bi- or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyl-oxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; —S(=O)$_p$—$C_{1-4}$alkyl;
Het$^1$ represents a monocyclic non-aromatic or aromatic heterocycle containing at least one heteroatom selected from O, S, S(=O)$_p$ or N; or a bicyclic or tricyclic non-aromatic or aromatic heterocycle containing at least one heteroatom selected from O, S, S(=O)$_p$ or N; said monocyclic heterocycle or said bi- or tricyclic heterocycle optionally being substituted with at least one substituent, in particular one, two, three, four or five substituents, each substituent independently being selected from hydroxyl; oxo; carboxyl; halo; $C_{1-6}$alkyl optionally substituted with aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; nitro; amino; mono- or di($C_{1-6}$alkyl)amino; $C_{3-6}$cycloalkyl-NR$^x$—; aryl-NR$^x$—; Het-NR$^x$—; $C_{3-6}$cycloalkyl$C_{1-4}$alkyl-NR$^x$—; aryl$C_{1-4}$alkyl-NR$^x$—; Het$C_{1-4}$alkyl-NR$^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; Het; Het$C_{1-4}$alkyl; Het-C(=O)—; Het-O—;

p represents 1 or 2;
provided that the following compounds

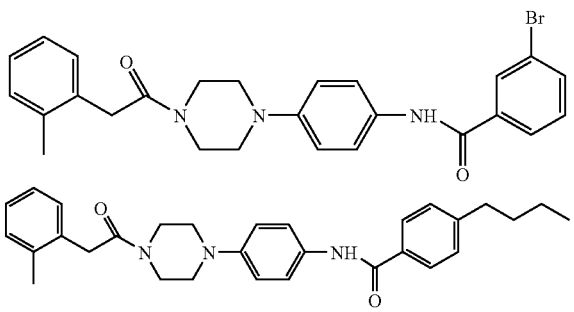

are excluded;
a N-oxide thereof, a pharmaceutically acceptable salt thereof or a solvate thereof.

A second embodiment of the present invention are those compounds of formula (I) or, whenever possible, any subgroup thereof as mentioned hereinbefore as embodiment wherein X represents —O—C(=O)—; —NR$^x$—C(=O)—; —Z—C(=O)—; —Z—NR$^x$—C(=O)—; —C(=O)—Z—; —NR$^x$—C(=O)—Z—; —NR$^x$—C(=S)—; in particular wherein X represents —NR$^x$—C(=O)—; —Z—C(=O)—; —Z—NR$^x$—C(=O)—; —C(=O)—Z—; —NR$^x$—C(=O)—Z—; —NR$^x$—C(=S)—; more in particular wherein X represents —NR$^x$—C(=O)—; —Z—C(=O)—; —Z—NR$^x$—C(=O)—; even more in particular X represents —NR$^x$—C(=O)— or —Z—NR$^x$—C(=O)—; or X represents —NR$^x$—C(=O)— or —Z—C(=O)—. Or X represents —O—C(=O)—; —C(=O)—C(=O)—; —NR$^x$—C(=O)—; —Z—C(=O)—; —Z—NR$^x$—C(=O)—; —C(=S)—; —NR$^x$—C(=S)—; —Z—C(=S)—; —Z—NR$^x$—C(=S)—.

A third embodiment of the present invention are those compounds of formula (I) or, whenever possible, any subgroup thereof as mentioned hereinbefore as embodiment wherein A represents N.

A fourth embodiment of the present invention are those compounds of formula (I) or, whenever possible, any subgroup thereof as mentioned hereinbefore as embodiment wherein A represents CH, in particular wherein A represents CH and the dotted line does not represent a bond.

A fifth embodiment of the present invention are those compounds of formula (I) or, whenever possible, any subgroup thereof as mentioned hereinbefore as embodiment wherein R$^1$ represents aryl$^1$ or Het$^1$; in particular optionally substituted phenyl, optionally substituted fluorenyl or an optionally substituted monocyclic non-aromatic or aromatic heterocycle containing at least one heteroatom each independently selected from O, S, S(=O)$_p$ or N, in particular S or N; more in particular phenyl or fluorenyl, said phenyl or fluorenyl optionally substituted with one or two substituents, said substituents independently selected from oxo, carboxyl, halo, $C_{1-6}$alkyl optionally substituted with carboxyl or $C_{1-4}$alkyloxycarbonyl, $C_{1-6}$alkyloxy, $C_{1-6}$alkyloxycarbonyl, amino, aryl, Het or polyhalo$C_{1-6}$alkyl; or a 4-, 5- or 6-membered non-aromatic or aromatic heterocycle, such as for example azetidinyl, thiazolidinyl, thiazolyl, pyrrolidinyl, piperidinyl, said 5- or 6-membered heterocycle optionally substituted with one or two substituents, said substituents independently selected from hydroxyl, oxo, $C_{1-6}$alkyl, $C_{1-6}$alkyloxycarbonyl, aryl or Het.

A sixth embodiment of the present invention are those compounds of formula (I) or, whenever possible, any subgroup thereof as mentioned hereinbefore as embodiment wherein R$^2$ represents $C_{3-6}$cycloalkyl, phenyl, 2,3-dihydro-1,4-benzodioxinyl or a 6-membered aromatic heterocycle containing 1 or 2 N atoms such as for example pyridyl, wherein said phenyl or heterocycle are optionally substituted with one to four substituents, preferably each substituent independently selected from halo, $C_{1-6}$alkyl, $C_{1-6}$alkyloxy, $C_{1-6}$alkylthio, $C_{1-6}$alkyloxycarbonyl, nitro, amino, mono- or di($C_{1-4}$alkyl)amino, aryloxy, R$^4$R$^3$N—$C_{1-6}$alkyl, Het-C(=O)—$C_{1-4}$ alkyl.

A seventh embodiment of the present invention are those compounds of formula (I) or, whenever possible, any subgroup thereof as mentioned hereinbefore as embodiment wherein the compound of formula (I) is a compound of formula (I')

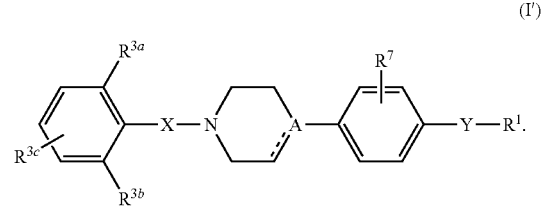

wherein R$^{3a}$ and R$^{3a}$ each independently represent hydrogen; hydroxyl; carboxyl; halo; $C_{1-6}$alkyl; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; —S(=O)$_p$—$C_{1-4}$alkyl; and wherein R$^{3c}$ represents hydrogen; hydroxyl; carboxyl; halo; $C_{1-6}$alkyl; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxycarbonyl wherein $C_{1-6}$alkyl may optionally be substituted with aryl; cyano; $C_{1-6}$alkylcarbonyl; nitro; amino; mono- or di($C_{1-4}$alkyl)amino; —S(=O)$_p$—$C_{1-4}$alkyl; R$^4$R$^3$N—C(=O)—; R$^4$R$^3$N—$C_{1-6}$alkyl; $C_{3-6}$cycloalkyl; aryl; aryloxy; aryl$C_{1-4}$alkyl; aryl-C(=O)—$C_{1-4}$alkyl; aryl-C(=O)—; Het; Het$C_{1-4}$alkyl; Het-C(=O)—$C_{1-4}$alkyl; Het-C(=O)—; Het-O—.

An eighth embodiment of the present invention are those compounds of formula (I) or, whenever possible, any subgroup thereof as mentioned hereinbefore as embodiment wherein the compound of formula (I) is a compound of formula (I")

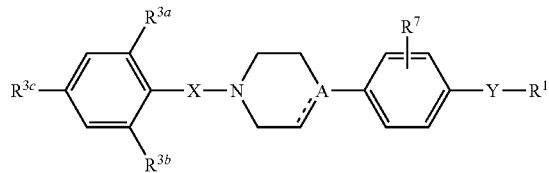
(I'')

wherein $R^{3a}$ and $R^{3a}$ each independently represent hydrogen; hydroxyl; carboxyl; halo; $C_{1-6}$alkyl; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; —S(=O)$_p$—$C_{1-4}$alkyl; and wherein $R^{3c}$ represents hydrogen; hydroxyl; carboxyl; halo; $C_{1-6}$alkyl; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxycarbonyl wherein $C_{1-6}$alkyl may optionally be substituted with aryl; cyano; $C_{1-6}$alkylcarbonyl; nitro; amino; mono- or di($C_{1-4}$alkyl)amino; —S(=O)$_p$—$C_{1-4}$alkyl; $R^4R^3N$—C(=O)—; $R^4R^3N$—$C_{1-6}$alkyl; $C_{3-6}$cycloalkyl; aryl; aryloxy; aryl$C_{1-4}$alkyl; aryl-C(=O)—$C_{1-4}$alkyl; aryl-C(=O)—; Het; Het$C_{1-4}$alkyl; Het-C(=O)—$C_{1-4}$alkyl; Het-C(=O)—; Het-O—.

A ninth embodiment of the present invention are those compounds of formula (I) or any subgroup thereof as mentioned hereinbefore as embodiment wherein the compound of formula (I) is a compound of formula (I') or (I'') and wherein $R^{3a}$ and $R^{3b}$ each independently represent halo, $C_{1-6}$alkyl or $C_{1-6}$alkyloxy; in particular halo or $C_{1-6}$alkyl; more in particular both $R^{3a}$ and $R^{3b}$ represent halo, more in particular both $R^{3a}$ and $R^{3b}$ represent chloro.

A tenth embodiment of the present invention are those compounds of formula (I) or, whenever possible, any subgroup thereof as mentioned hereinbefore as embodiment wherein the compound of formula (I) is a compound of formula (I') or (I'') and wherein $R^{3c}$ represents amino; mono- or di($C_{1-4}$alkyl)amino; $R^4R^3N$—C(=O)—; $R^4R^3N$—$C_{1-6}$alkyl; Het-C(=O)— or Het$C_{1-4}$alkyl; or $R^{3c}$ represents hydrogen.

An eleventh embodiment of the present invention are those compounds of formula (I) or, whenever possible, any subgroup thereof as mentioned hereinbefore as embodiment wherein p represents 2.

A twelfth embodiment of the present invention are those compounds of formula (I) or, whenever possible, any subgroup thereof as mentioned hereinbefore as embodiment wherein Z represents $C_{1-6}$alkanediyl or $C_{2-6}$alkenediyl, in particular $C_{1-6}$alkanediyl, more in particular —CH$_2$—.

A thirteenth embodiment of the present invention are those compounds of formula (I) or, whenever possible, any subgroup thereof as mentioned hereinbefore as embodiment wherein $R^x$ represents hydrogen.

A fourteenth embodiment of the present invention are those compounds of formula (I) or, whenever possible, any subgroup thereof as mentioned hereinbefore as embodiment wherein Y represents —NR$^x$—C(=O)—.

A fifteenth embodiment of the present invention are those compounds of formula (I) or, whenever possible, any subgroup thereof as mentioned hereinbefore as embodiment wherein Y represents —C(=O)—NR$^x$—.

A sixteenth embodiment of the present invention are those compounds of formula (I) or, whenever possible, any subgroup thereof as mentioned hereinbefore as embodiment wherein $R^7$ represents hydrogen.

A seventeenth embodiment of the present invention are those compounds of formula (I) or, whenever possible, any subgroup thereof as mentioned hereinbefore as embodiment wherein $R^7$ represents halo, $C_{1-4}$alkyl or $C_{1-4}$alkyl substituted with hydroxyl; in particular halo.

An eighteenth embodiment of the present invention are those compounds of formula (I) or, whenever possible, any subgroup thereof as mentioned hereinbefore as embodiment wherein aryl represents phenyl or phenyl substituted with halo, $C_{1-6}$alkyl, polyhalo$C_{1-6}$alkyl or $C_{1-6}$alkyloxycarbonyl.

A nineteenth embodiment of the present invention are those compounds of formula (I) or, whenever possible, any subgroup thereof as mentioned hereinbefore as embodiment wherein Het represents a monocyclic non-aromatic or aromatic heterocycle containing at least one heteroatom each independently selected from O, S, S(=O)$_p$ or N; or a bicyclic non-aromatic or aromatic heterocycle containing at least one heteroatom each independently selected from O, S, S(=O)$_p$ or N, in particular N; said monocyclic heterocycle or said bicyclic heterocycle optionally being substituted with one or two substituents, each substituent independently being selected from oxo; or $C_{1-6}$alkyl.

A twenty embodiment of the present invention are those compounds of formula (I) or, whenever possible, any subgroup thereof as mentioned hereinbefore as embodiment wherein one or more, preferably all, of the following restrictions apply:
a) X represents —NR$^x$—C(=O)—; —Z—NR$^x$—C(=O)—; or —NR$^x$—C(=S)—;
b) $R^1$ represents aryl$^1$ or Het$^1$;
c) $R^2$ represents $C_{3-6}$cycloalkyl, phenyl or 2,3-dihydro-1,4-benzodioxinyl, wherein said phenyl is optionally substituted with one to four substituents, each substituent independently selected from halo, $C_{1-6}$alkyl, $C_{1-6}$alkyloxy, $C_{1-6}$alkylthio, $C_{1-6}$alkyloxycarbonyl, nitro, amino, mono- or di($C_{1-4}$alkyl)amino, aryloxy;
d) A represents N;
e) A represents CH;
f) Z represents $C_{1-6}$alkanediyl or $C_{2-6}$alkenediyl;
g) $R^x$ represents hydrogen.
h) aryl$^1$ represents phenyl or fluorenyl, said phenyl or fluorenyl optionally substituted with halo, $C_{1-6}$alkyl or polyhalo$C_{1-6}$ alkyl;
i) Het$^1$ represents a 4-, 5- or 6-membered non-aromatic or aromatic heterocycle, such as for example azetidinyl, thiazolidinyl, thiazolyl, pyrrolidinyl, piperidinyl, said 5- or 6-membered heterocycle optionally substituted with hydroxyl, oxo, $C_{1-6}$alkyl, $C_{1-6}$alkyloxycarbonyl, aryl or Het;
j) Y represents —NR$^x$—C(=O)—;
k) $R^7$ represents hydrogen.

A twenty first embodiment of the present invention are those compounds of formula (I) or, whenever possible, any subgroup thereof as mentioned hereinbefore as embodiment wherein one or more, preferably all, of the following restrictions apply:
a) A represents CH;
b) A represents N;
c) the dotted line represents a bond in case A represents a carbon atom;
d) the dotted line doesn't represents a bond in case A represents a carbon atom;
e) X represents —O—C(=O)—; —NR$^x$—C(=O)—; —Z—C(=O)—; —Z—NR$^x$—C(=O)—; —NR$^x$—C(=S)—;
f) Z represents $C_{1-6}$alkanediyl;

g) $R^x$ represents hydrogen;
h) Y represents —C(=O)—$NR^x$— or —$NR^x$—C(=O)—;
i) $R^1$ represents $aryl^1$ or $Het^1$;
j) $R^2$ represents $C_{3-6}$cycloalkyl, phenyl, 2,3-dihydro-1,4-benzodioxinyl, or a 6-membered aromatic heterocycle containing 1 or 2 N atoms, wherein said $C_{3-6}$cycloalkyl, phenyl, 2,3-dihydro-1,4-benzodioxinyl, or 6-membered aromatic heterocycle containing 1 or 2 N atoms may optionally be substituted with at least one substituent, in particular one to four substituents, each substituent independently selected from halo; $C_{1-6}$alkyl; $C_{1-6}$alkyloxy; $C_{1-6}$alkylthio; $C_{1-6}$alkyloxycarbonyl; nitro; mono- or di($C_{1-4}$alkyl)amino; $R^4R^3N$—$C_{1-6}$alkyl; aryloxy; Het-C(=O)—$C_{1-4}$alkyl;
k) $R^3$ represents $C_{1-4}$alkyl;
l) $R^4$ represents $C_{1-4}$alkyl;
m) $R^7$ represents hydrogen or halo;
n) aryl represents phenyl or phenyl substituted with halo; $C_{1-6}$alkyl; polyhalo$C_{1-6}$alkyl; $C_{1-6}$alkyloxycarbonyl;
o) $aryl^1$ represents phenyl or fluorenyl; each of said phenyl or fluorenyl optionally substituted with one or two substituents, each substituent independently being selected from oxo; carboxyl; halo; $C_{1-6}$alkyl optionally substituted with carboxyl or $C_{1-4}$alkyloxycarbonyl; $C_{1-6}$alkyloxy; $C_{1-6}$alkyloxy-carbonyl; amino; aryl; Het;

p) Het represents a monocyclic non-aromatic or aromatic heterocycle containing at least one heteroatom each independently selected from O, S, S(=O)$_p$ or N; or a bicyclic non-aromatic or aromatic heterocycle containing at least one heteroatom each independently selected from N; said monocyclic heterocycle or said bicyclic heterocycle optionally being substituted with one or two substituents, each substituent independently being selected from oxo or $C_{1-6}$alkyl;

q) $Het^1$ represents a monocyclic non-aromatic or aromatic heterocycle containing at least one heteroatom each independently selected from S or N; said monocyclic heterocycle optionally being substituted with at least one substituent, in particular one or two substituents, each substituent independently being selected from hydroxyl; oxo; $C_{1-6}$alkyl; $C_{1-6}$alkyloxy-carbonyl; aryl; Het;

r) p represents 2.

Preferred compounds of formula (I) are selected from

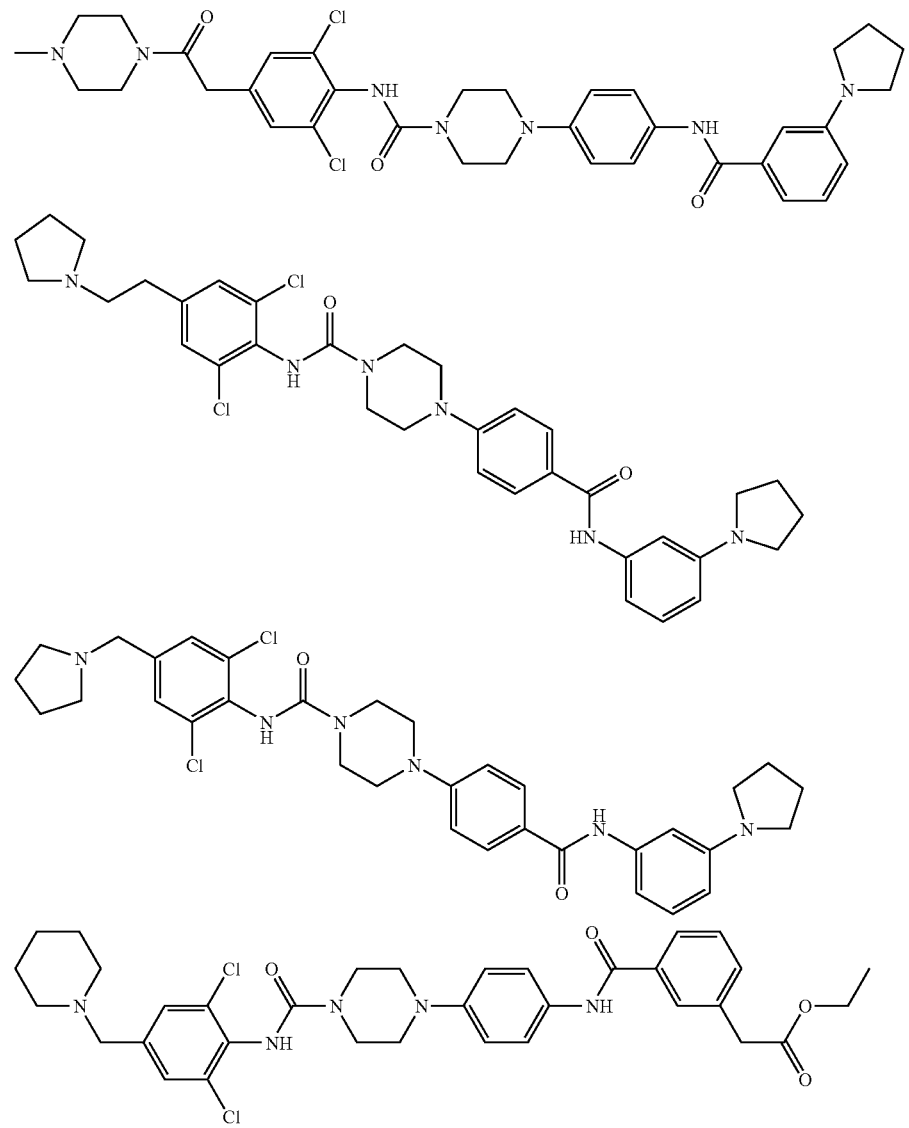

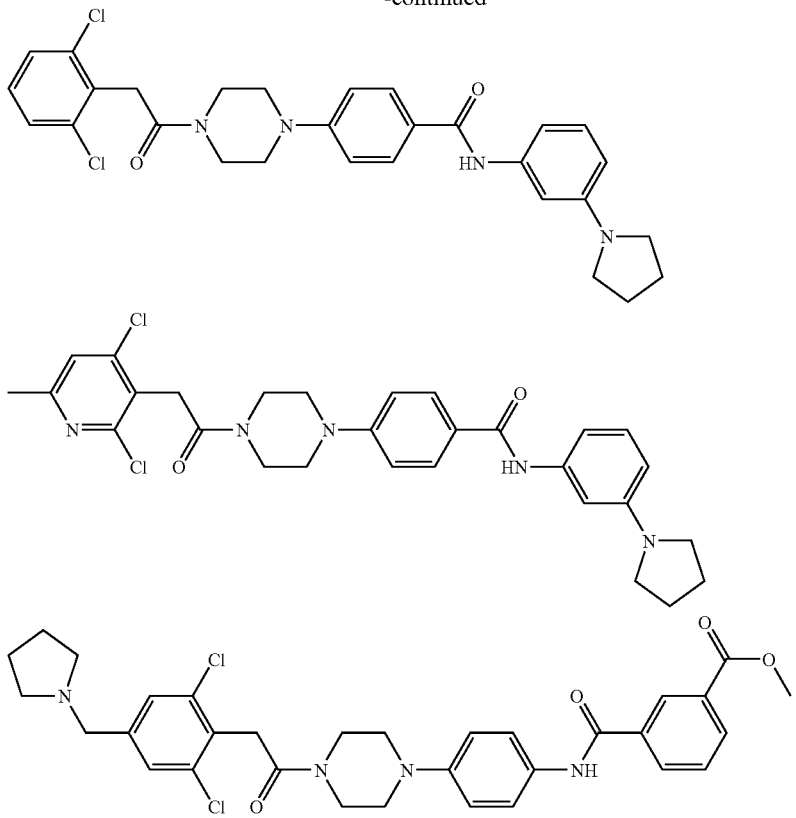

a N-oxide thereof, a pharmaceutically acceptable salt thereof or a solvate thereof.

Another embodiment of the present invention is the use of a compound of formula (I''') as indicated hereinabove, wherein the compound of formula (I''') is a compound wherein $R^2$ represents hydrogen, $C_{1-6}$alkyl or $C_{2-6}$alkenyl.

The embodiments set out above for the compounds of formula (I) are also applicable, whenever possible, to the compound of formula (I''').

In general, compounds of formula (I) wherein Y represents —$NR^x$—C(=O)—, said compounds being represented by formula (I-a), can be prepared by reacting an intermediate of formula (II) with an intermediate of formula (III) in the presence of a suitable dehydrating (coupling) agent, such as for example N'-(ethylcarbonimidoyl)-N,N-dimethyl-1,3-propanediamine monohydrochloride (EDCI), dicyclohexylcarbodiimide (DCC), carbonyl diimidazole (CDI), 1-[bis(di-methylamino)methylene]-1H-benzotriazoliumhexafluorophosphate(1-)3-oxide (HBTU), 1-[bis(dimethyl-amino)methylene]-5-chloro-1H-benzotriazoliumhexafluorophosphate(1-)3-oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole, in the presence of a suitable solvent, such as for example N,N-dimethylformamide, tetrahydrofuran or dichloromethane, and optionally in the presence of a suitable base, such as for example N,N-diisopropyl-ethanamine or N,N-diethyl-ethanamine.

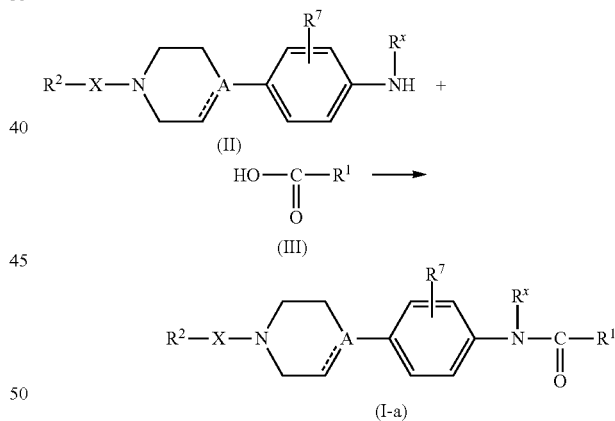

The above reaction can be performed as a fast synthesis reaction thereby using appropriate reagents well-known for fast synthesis, such as for example dicyclohexylcarbodiimide (DCC) linked to an appropriate carrier, e.g. polystyrene. Also for the purification of the reaction mixture, appropriate fast-synthesis reagents can be used, such as for example 1-ethenyl-4-(isocyanatomethyl)-benzene polymer with ethenylbenzene.

Compounds of formula (I-a) can also be prepared by reacting an intermediate of formula (II) with an intermediate of formula (III') wherein $W_1$ represents a suitable leaving group, such as for example halo, e.g. chloro and the like, in the presence of a suitable base, such as for example sodium hydride, sodium bicarbonate, N,N-diisopropyl-ethanamine or N,N-diethyl-ethanamine, and a suitable solvent, such as for example N,N-dimethylformamide, dichloromethane, acetonitrile or tetrahydrofuran

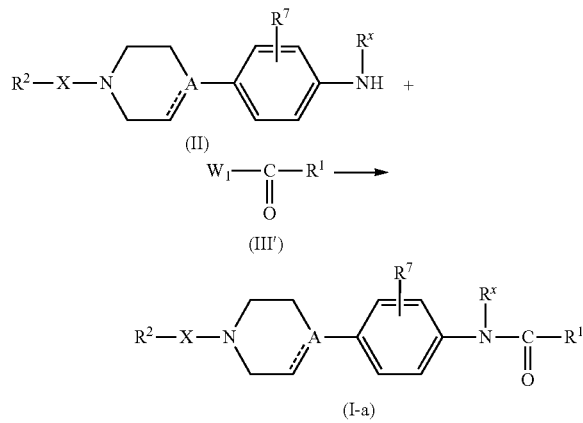

Compounds of formula (I) wherein X represents $X_1$—NH—C(=O)— with $X_1$ representing a direct bond or Z, said compounds being represented by formula (I-b), can be prepared by reacting an intermediate of formula (IV) with an intermediate of formula (V) in the presence of a suitable solvent, such as for example acetonitrile, N,N-dimethylformamide or dichloromethane or an alcohol, e.g. methanol, optionally in the presence of a suitable base, such as for example N,N-diethyl-ethanamine. Intermediates of formula (IV) are commercially available or can be prepared by reacting $R^2$—$X_1$—$NH_2$ with phosgene in the presence of a suitable solvent, such as for example toluene.

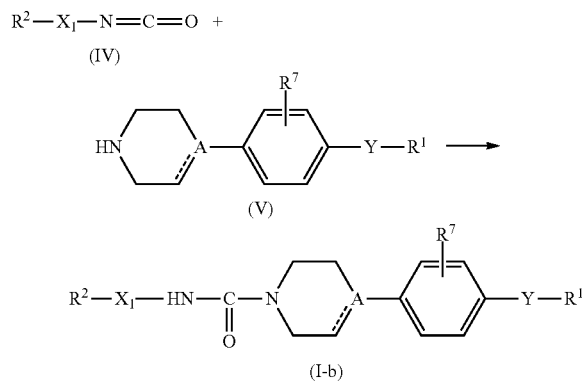

The above reaction can also be performed as a fast synthesis reaction thereby using appropriate reagents well-known for fast synthesis, such as for example for the purification of the reaction mixture 1-ethenyl-4-(isocyanatomethyl)-benzene polymer with ethenylbenzene and tris-2-aminoethylamine linked to polystyrene can be used.

Compounds of formula (I-b) wherein $X_1$ represents a direct bond, said compounds being represented by formula (I-b-1), can be prepared by reacting an intermediate of formula (IV') with $Cl_3COC(=O)$—Cl or $C(=O)Cl_2$, optionally in the presence of HCl in diethylether, and in the presence of a suitable solvent, such as for example toluene or acetonitrile, followed by reaction with an intermediate of formula (V) in the presence of a suitable solvent, such as for example acetonitrile, N,N-dimethylformamide or dichloromethane, optionally in the presence of a suitable base, such as for example N,N-diethyl-ethanamine or N,N-diisopropyl-ethanamine.

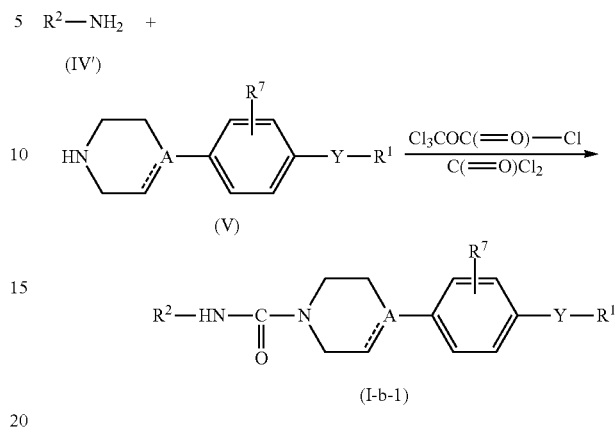

Compounds of formula (I) wherein X represents $X_1$—NH—C(=S)— with $X_1$ representing a direct bond or Z, said compounds being represented by formula (I-c), can be prepared by reacting an intermediate of formula (VI) with an intermediate of formula (V) in the presence of a suitable base, such as for example N,N-diethyl-ethanamine, and a suitable solvent, such as for example dichloromethane or tetrahydrofuran.

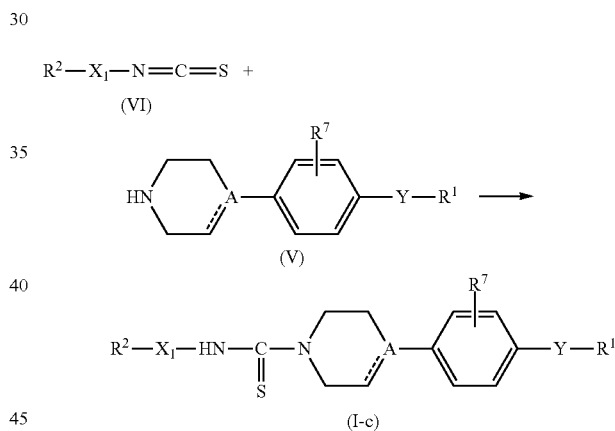

Compounds of formula (I) wherein X represents —$X_1$—C(=O)— with $X_1$ representing a direct bond or Z, said compounds being represented by formula (I-d), can be prepared by reacting an intermediate of formula (VII) with an intermediate of formula (V) in the presence of a suitable dehydrating (coupling) agent, such as for example N'-(ethylcarbonimidoyl)-N,N-dimethyl-1,3-propanediamine monohydrochloride (EDCI), dicyclohexylcarbodiimide (DCC), carbonyl diimidazole (CDI), 1-[bis(di-methylamino)methylene]-1H-benzotriazoliumhexafluorophosphate(1-)3-oxide (HBTU), 1-[bis(dimethyl-amino)methylene]-5-chloro-1H-benzotriazolium-hexafluorophosphate(1-)3-oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole, in the presence of a suitable solvent, such as for example N,N-dimethylformamide, dichloromethane, acetonitrile or tetrahydrofuran, and optionally in the presence of a suitable base, such as for example N,N-diisopropyl-ethanamine or N,N-diethyl-ethanamine. This reaction of an intermediate of formula (VII) with an intermediate of formula (V) can also be performed in the presence of a suitable activating agent, such as for example Cl—C(=O)—C(=O)—Cl, a suitable base, such as for example N,N-diethyl-ethanamine, and a suitable solvent, such as for example N,N-dimethylformamide.

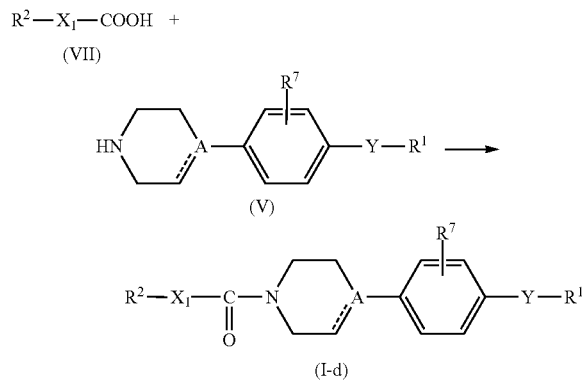

Compounds of formula (I-d) wherein $X_1$ represents a direct bond, said compounds being represented by formula (I-d-1), can be prepared by reacting an intermediate of formula (VII') wherein $W_1$ represents a suitable leaving group, such as for example halo, e.g. chloro and the like, with an intermediate of formula (V) in the presence of a suitable base, such as for example N-methyl morpholine, and a suitable solvent, such as for example N,N-dimethylformamide.

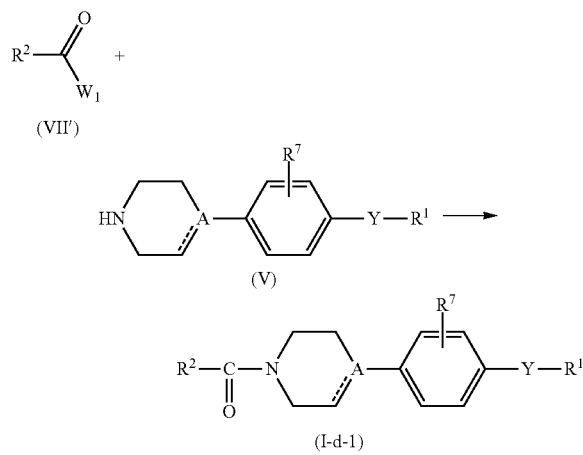

Compounds of formula (I''') wherein X represents —S(=O)$_p$—, said compounds being represented by formula (I'''-e), can be prepared by reacting an intermediate of formula (XVII) wherein $W_3$ represents a suitable leaving group, such as for example halo, e.g. chloro and the like, with an intermediate of formula (V) in the presence of a suitable base, such as for example N,N-diisopropyl-ethanamine or N,N-diethyl-ethanamine, and a suitable solvent, such as for example dichloromethane.

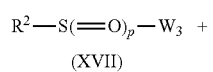

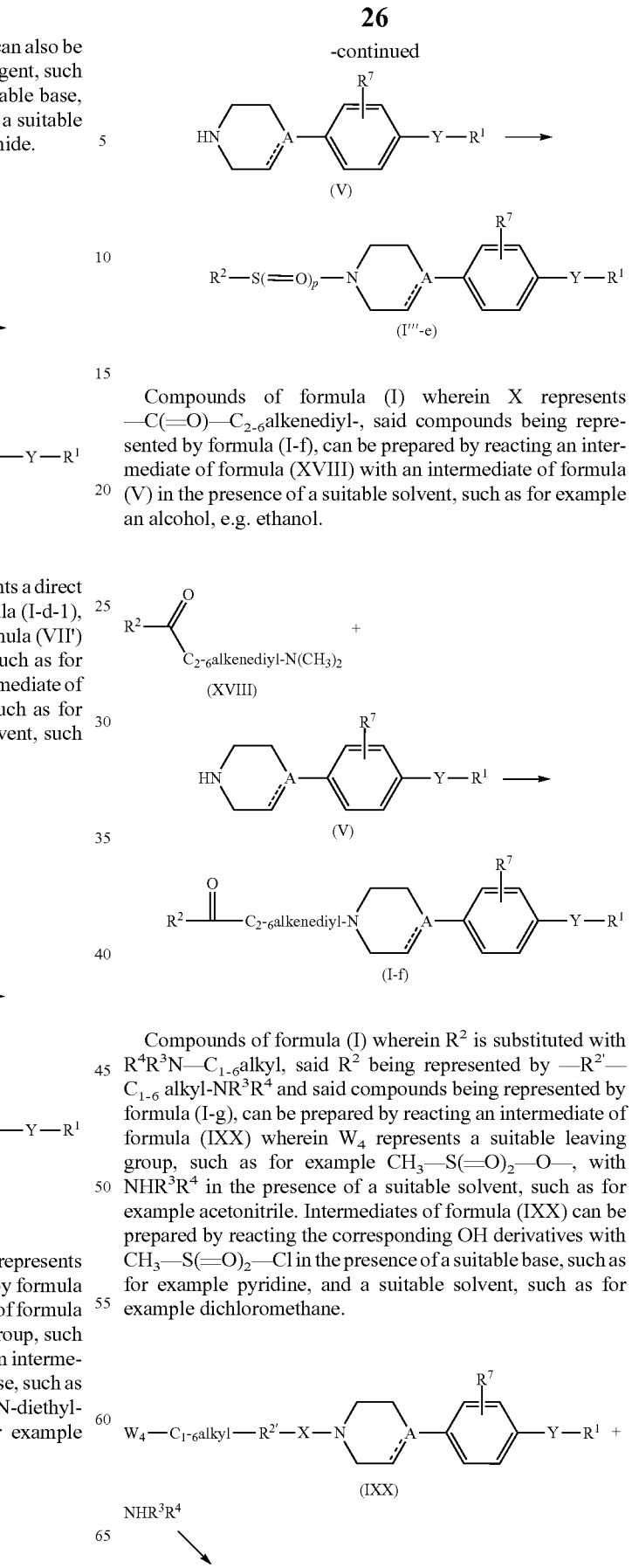

Compounds of formula (I) wherein X represents —C(=O)—C$_{2-6}$alkenediyl-, said compounds being represented by formula (I-f), can be prepared by reacting an intermediate of formula (XVIII) with an intermediate of formula (V) in the presence of a suitable solvent, such as for example an alcohol, e.g. ethanol.

Compounds of formula (I) wherein $R^2$ is substituted with $R^4R^3N$—C$_{1-6}$alkyl, said $R^2$ being represented by —R$^{2'}$—C$_{1-6}$ alkyl-NR$^3R^4$ and said compounds being represented by formula (I-g), can be prepared by reacting an intermediate of formula (IXX) wherein $W_4$ represents a suitable leaving group, such as for example CH$_3$—S(=O)$_2$—O—, with NHR$^3R^4$ in the presence of a suitable solvent, such as for example acetonitrile. Intermediates of formula (IXX) can be prepared by reacting the corresponding OH derivatives with CH$_3$—S(=O)$_2$—Cl in the presence of a suitable base, such as for example pyridine, and a suitable solvent, such as for example dichloromethane.

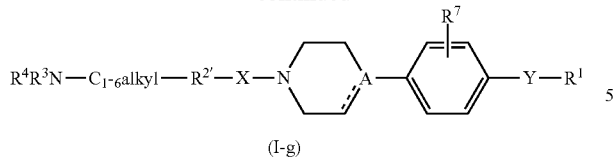

(I-g)

Compounds of formula (I) wherein the $R^1$ substituent is substituted with amino can be prepared from the corresponding compound wherein the amino function is protected by a suitable protecting group, such as for example a tertiair butyloxycarbonyl group, in the presence of a suitable acid, such as for example trifluoroacetic acid, and a suitable solvent, such as for example dichloromethane. Said protected compounds can be prepared according to the synthesis protocol described hereinabove for the compounds of formula (I) starting from an intermediate of formula (II).

Compounds of formula (I) wherein Y represents —C(=O)—$NR^x$—, said compounds being represented by formula (I-h), can be prepared by reacting an intermediate of formula (XXV) with an intermediate of formula (XXVI) in the presence of DECP, a suitable base, such as for example N,N-diethyl-ethanamine or N,N-diisopropyl-ethanamine, and a suitable solvent, such as for example dichloromethane or acetonitrile.

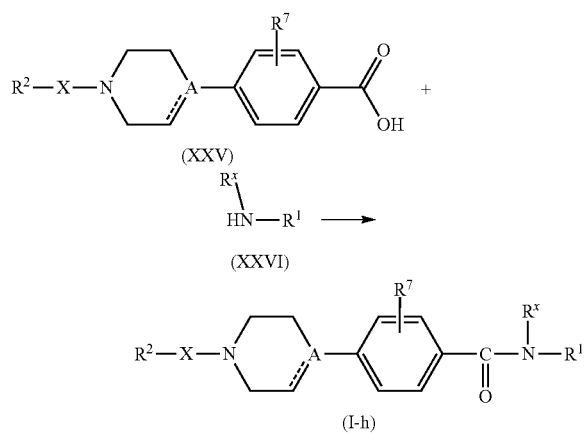

Compounds of formula (I) wherein $R^7$ represents $C_{1-4}$alkyl substituted with hydroxyl, said compounds being represented by formula (I-i), can be prepared by reacting an intermediate of formula (XLIII) with an appropriate acid, such as for example HCl and the like, in the presence of a suitable solvent, such as for example an alcohol, e.g. 2-propanol.

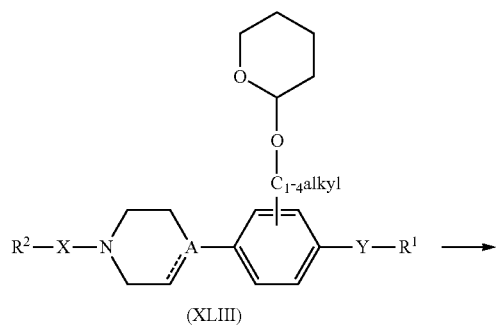

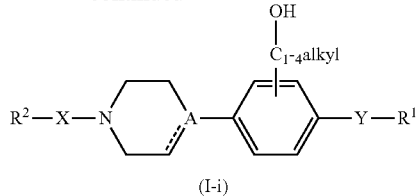

(I-i)

Compounds of formula (I) wherein X contains $Z^1$, said $Z^1$ being Z substituted with amino, said X being represented by $Z^1(NH_2)$—$X_2$, wherein $X_2$ represents the remainder of the linker X, and said compounds being represented by formula (I-j), can be prepared by deprotecting an intermediate of formula (XLIV) wherein P represents a suitable leaving group, such as for example tert butoxycarbonyl, with a suitable acid, such as for example trifluoroacetic acid, in the presence of a suitable solvent, such as for example dichloromethane.

The compounds of formula (I) may further be prepared by converting compounds of formula (I) into each other according to art-known group transformation reactions.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (I) wherein $R^1$ or $R^2$ is unsubstituted, can be converted into a compound wherein $R^1$ or $R^2$ contain a $C_{1-4}$alkyl-S(=O)$_p$— substituent, by reaction with $C_{1-4}$alkyl-S(=O)$_p$—$W_5$ wherein $W_5$ represents a suitable leaving group, such as for example halo, e.g. chloro and the like, in the presence of a suitable base, such as for example N,N-diethyl-ethanamine, and in the presence of a suitable solvent, such as for example acetonitrile.

Compounds of formula (I) wherein $R^1$ or $R^2$ contains a $C_{1-6}$alkyloxycarbonyl substituent, can be converted into a compound of formula (I) wherein $R^1$ or $R^2$ contain a carboxyl substituent, by reaction with a suitable base, such as for example sodium hydroxide, in the presence of a suitable solvent, such as for example dioxane.

Compounds of formula (I) wherein $R^1$ or $R^2$ contain a $C_{1-6}$alkyloxycarbonyl substituent, can also be converted into a compound of formula (I) wherein $R^1$ or $R^2$ contain a $CH_2$—OH substituent, by reaction with a suitable reducing agent, such as for example LiBH, in the presence of a suitable solvent, such as for example tetrahydrofuran or dioxane.

Compounds of formula (I) wherein $R^1$ or $R^2$ contain a $C_{1-6}$alkyloxycarbonyl substituent, can also be converted into a compound of formula (I) wherein $R^1$ or $R^2$ are unsubstituted by reaction with a suitable acid, such as for example hydrochloric acid and the like.

Compounds of formula (I) wherein $R^1$ or $R^2$ contain a $C_{1-5}$alkyl-carbonyl substituent, can be converted into a compound of formula (I) wherein $R^1$ or $R^2$ contain a $C_{1-5}$alkyl-CH(OH)— substituent, by reaction with a suitable reducing agent, such as for example $NaBH_4$, in the presence of a suitable solvent, such as for example an alcohol, e.g. methanol.

Compounds of formula (I) wherein $R^1$ or $R^2$ contain a $C_{1-6}$alkyloxy substituent, can be converted into a compound of formula (I) wherein $R^1$ or $R^2$ contain a OH substituent, by reaction with a suitable reducing agent, such as for example $BBr_3$, in the presence of a suitable solvent, such as for example dichloromethane or dichloroethane.

Compounds of formula (I) wherein $R^1$ or $R^2$ contain a carboxyl substituent, can be converted into a compound of formula (I) wherein $R^1$ or $R^2$ contain a Het-C(=O)-substituent wherein Het represents an optionally substituted monocyclic saturated heterocycle containing at least one N atom, said heterocycle being linked via the N atom to the C(=O) group, by reaction with said heterocycle in the presence a suitable dehydrating (coupling) agent, such as for example N'-(ethylcarbonimidoyl)-N,N-dimethyl-1,3-propanediamine monohydrochloride (EDCI), dicyclohexylcarbodiimide (DCC), carbonyl diimidazole (CDI), 1-[bis(di-methylamino)methylene]-1H-benzotriazoliumhexafluorophosphate(1-)3-oxide (HBTU) or 1-[bis(dimethyl-amino)methylene]-5-chloro-1H-benzotriazolium-hexafluorophosphate(1-)3-oxide (HCTU), optionally combined with hydroxy benzotriazole or chloro hydroxybenzotriazole, in the presence of a suitable solvent, such as for example N,N-dimethylformamide, dichloromethane, acetonitrile or tetrahydrofuran, and optionally in the presence of a suitable base, such as for example N,N-diisopropyl-ethanamine or N,N-diethylethanamine. This reaction can also be performed as a fast synthesis reaction thereby using appropriate reagents well-known for fast synthesis, such as for example dicyclohexyl-carbodiimide (DCC) or carbonyl diimidazole (CDI), linked to an appropriate carrier, e.g. polystyrene. Also for the purification of the reaction mixture, appropriate fast-synthesis reagents can be used, such as for example 1-ethenyl-4-(iso-cyanatomethyl)-benzene polymer with ethenylbenzene.

The compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, chiral liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography or SCF (Super Critical Fluid) chromatography, in particular using a chiral stationary phase.

Some of the intermediates and starting materials are known compounds and may be commercially available or may be prepared according to art-known procedures.

Intermediates of formula (II) wherein X represents $X_1$—NH—C(=O)— with $X_1$ representing a direct bond or Z, said intermediates being represented by formula (II-a), can be prepared by reacting an intermediate of formula (IV) with an intermediate of formula (VIII) wherein P represents a suitable protecting group, such as for example tertiair butyloxycarbonyl, in the presence of a suitable solvent, such as for example dichloromethane, followed by deprotecting the resulting intermediate of formula (IX) in the presence of a suitable acid, such as for example trifluoroacetic acid, and in the presence of a suitable solvent, such as for example dichloromethane. Before performing the deprotection reaction, the intermediate of formula (IX) can optionally be converted into an intermediate of formula (IX') by reaction with $C_{1-4}$alkyl halide, e.g. $CH_3I$, in the presence of a suitable base, such as for example NaH, and a suitable solvent, such as for example N,N-dimethylformamide.

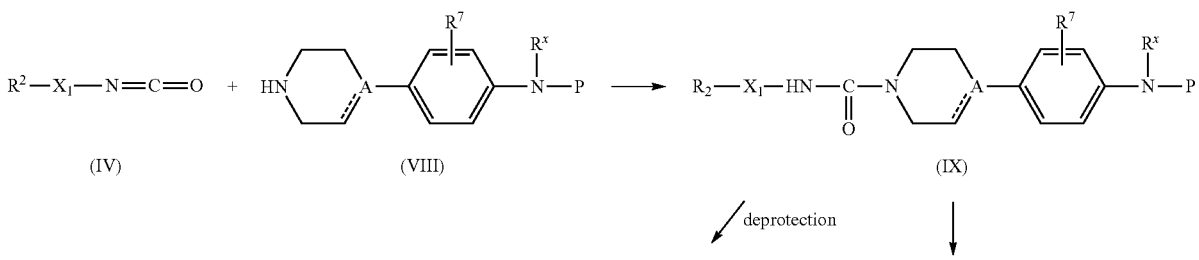

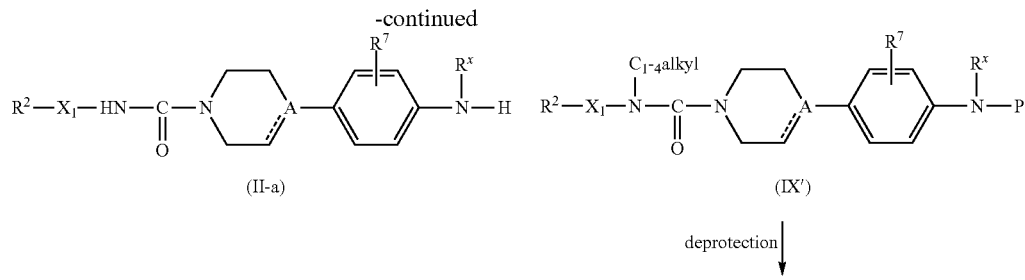

(II-a)          (IX')

deprotection ↓

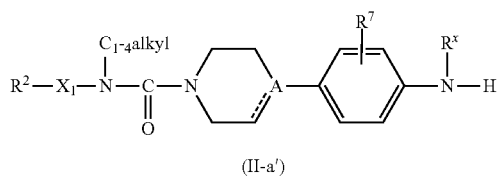

(II-a')

Intermediates of formula (II-a) wherein $R^x$ represents hydrogen, said intermediates being represented by formula (II-a-1), can be prepared by reacting an intermediate of formula (IV) with an intermediate of formula (X) in the presence of a suitable solvent, such as for example dichloromethane, followed by hydrogenating ($H_2$ or $N_2H_4 \cdot H_2O$) the resulting intermediate of formula (XI) in the presence of a suitable catalyst, such as for example platinum on charcoal or raney nickel, optionally a suitable catalyst poison, such as for example a thiophene solution, and a suitable solvent, such as for example tetrahydrofuran or an alcohol, e.g. methanol. Before performing the hydrogenation reaction, the intermediate of formula (XI) can optionally be converted into an intermediate of formula (XI') by reaction with $C_{1-4}$alkyl halide, e.g. $CH_3I$, in the presence of a suitable base, such as for example NaH, and a suitable solvent, such as for example N,N-dimethylformamide.

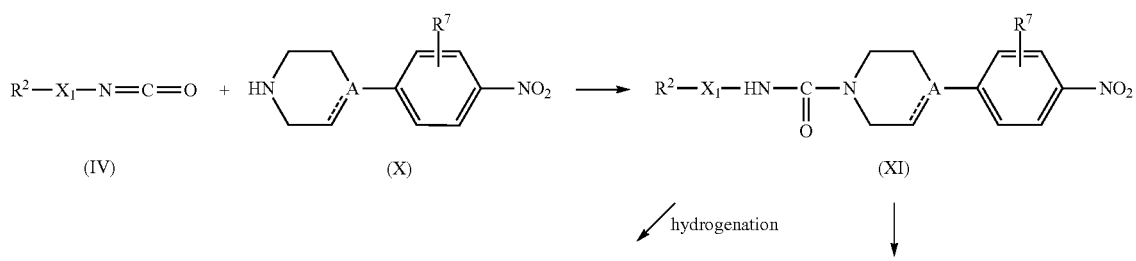

(IV)     (X)          (XI)

hydrogenation ↙      ↓

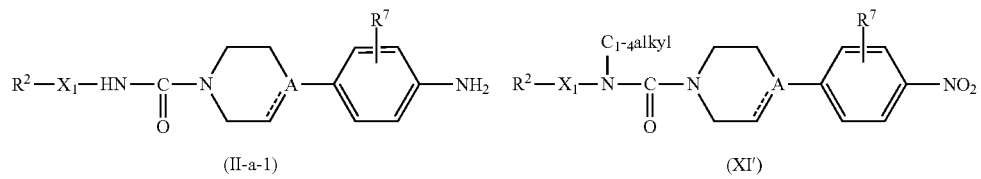

(II-a-1)           (XI')

hydrogenation ↓

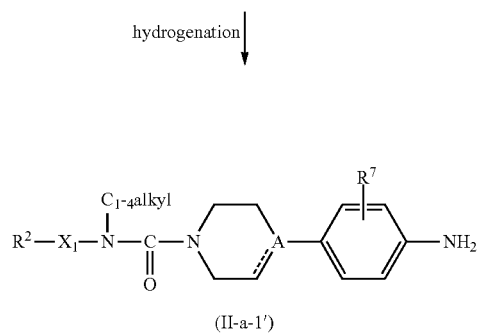

(II-a-1')

Intermediates of formula (II-a) wherein $R^x$ represents hydrogen and wherein $X_1$ represents a direct bond, said intermediates being represented by formula (II-a-2), can be prepared by reacting an intermediate of formula (IV') with $Cl_3COC(=O)$—Cl followed by reaction with an intermediate of formula (X) in the presence of a suitable base, such as for example N,N-diethyl-ethanamine, and a suitable solvent, such as for example toluene, followed by hydrogenating ($H_2$ or $N_2H_4.H_2O$) the resulting intermediate of formula (XX) in the presence of a suitable catalyst, such as for example platinum on charcoal or raney nickel, optionally a suitable catalyst poison, such as for example a thiophene solution, and a suitable solvent, such as for example tetrahydrofuran or an alcohol, e.g. methanol. Before performing the hydrogenation reaction, the intermediate of formula (XX) can optionally be converted into an intermediate of formula (XX') by reaction with $C_{1-4}$alkyl halide, e.g. $CH_3I$, in the presence of a suitable base, such as for example NaH, and a suitable solvent, such as for example N,N-dimethylformamide.

Intermediates of formula (II) wherein X represents —O—C(=O)—, said intermediates being represented by formula (II-b), can be prepared by reacting an intermediate of formula (XXVII) with an intermediate of formula (XXVIII) wherein $W_3$ represents a suitable leaving group, such as for example halo, e.g. chloro, in the presence of NaH, and a suitable solvent, such as for example tetrahydrofuran, followed by hydrogenating the resulting product of formula (XXIX) in a next step in the presence of $H_2$, a suitable catalyst, such as for example platina on charcoal, a suitable catalyst poison, such as for example thiophene, and a suitable solvent, such as for example acetic acid.

Intermediates of formula (III) can be prepared by hydrolizing an intermediate of formula (XII) with a suitable base, such as for example potassium hydroxide or sodium hydroxide, in the presence of a suitable solvent, such as for example water, tetrahydrofuran, dioxane or an alcohol, e.g. methanol. Intermediates of formula (XII) wherein $R^1$ represents $Het^1$ wherein said $Het^1$ is a heterocycle substituted with optionally substituted phenyl or an optionally substituted heterocycle, can be prepared by reacting the protected heterocycle with optionally substituted phenyl in the presence of a suitable catalyst, such as for example palladium acetate, in the presence of a suitable catalyst ligand, such as for example 1,1'-(1,5-pentanediyl)bis[1,1'-diphenylphosphine], a suitable base, such as for example potassium acetate, and a suitable solvent, such as for example N-methyl-pyrrolidin-2-one or by reacting the optionally substituted heterocyle with optionally substituted phenyl carrying a suitable leaving group, such as for example halo, e.g. bromo, iodo and the like, or an optionally substituted heterocycle carrying a suitable leaving group, such as for example halo, e.g. bromo, iodo and the like, in the presence of a suitable catalyst, such as for example palladium acetate, in the presence of a suitable catalyst ligand, such as for example 1,3-propanediylbis[diphenylphosphine], a suitable base, such as for example potassium acetate or cesium carbonate, and a suitable solvent, such as for example N-methyl-pyrrolidin-2-one.

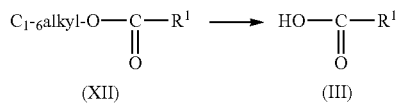

Intermediates of formula (V) wherein Y represents —NR$^x$—C(═O)—, said intermediates being represented by formula (V-a), can be prepared by reacting an intermediate of formula (XIII) wherein P represents a suitable protecting group, such as for example benzyl, with an intermediate of formula (XIV) wherein W$_2$ represents a suitable leaving group, such as for example halo, e.g. chloro and the like, in the presence of a suitable base, such as for example N,N-diethylethanamine, and a suitable solvent, such as for example dichloromethane, followed by deprotecting the resulting intermediate of formula (XV) with H$_2$ in the presence of a suitable catalyst, such as for example palladium on charcoal, and a suitable solvent, such as for example tetrahydrofuran and/or a suitable alcohol, e.g. methanol.

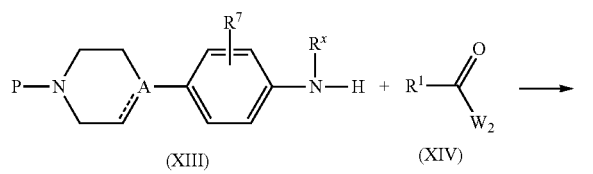

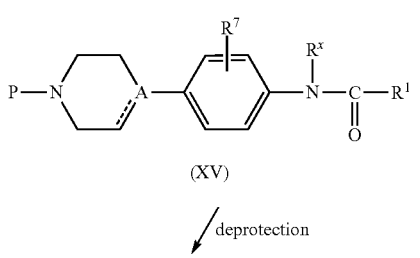

Intermediates of formula (V-a) can also be prepared by reacting an intermediate of formula (XIII) with an intermediate of formula (III) in the presence of a suitable activating agent, such as for example oxalyl chloride, in the presence of a suitable base, such as for example N,N-diethyl-ethanamine, and a suitable solvent, such as for example dichloromethane or N,N-dimethylformamide, followed by deprotecting the resulting intermediate of formula (XV) with H$_2$ in the presence of a suitable catalyst, such as for example palladium on charcoal, and a suitable solvent, such as for example tetrahydrofuran and/or a suitable alcohol, e.g. methanol. Deprotection can also be performed in the presence of 1-chloroethyl carbonochloridic acid ester as deprotecting agent in the presence of a suitable solvent such as for example dichloroethane and an alcohol, e.g. methanol.

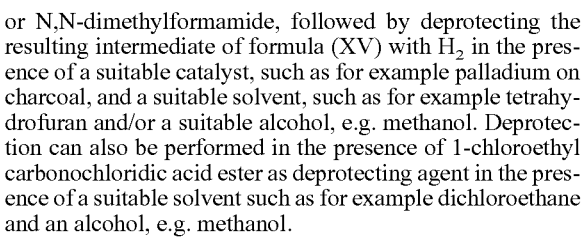

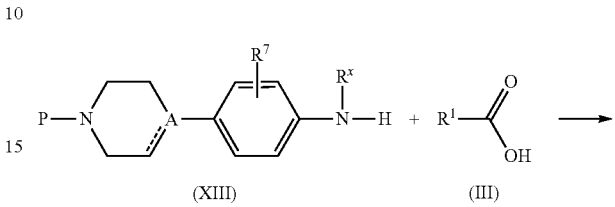

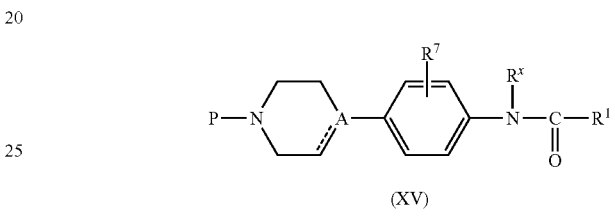

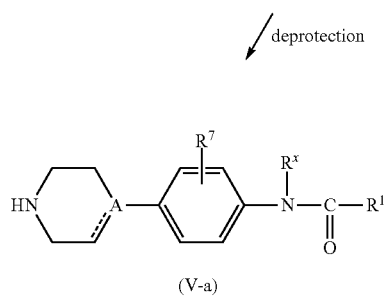

Intermediates of formula (V-a), can also be prepared according to the following reaction scheme wherein an intermediate of formula (XXI) wherein P represents a suitable protecting group, such as for example benzyloxycarbonyl or tertiair butyloxy or benzyl, and wherein W$_6$ represents a suitable leaving group, such as for example halo, e.g. chloro and the like, with an intermediate of formula (X) in the presence of a suitable base, such as for example NaHCO$_3$, and a suitable solvent, such as for example dichloromethane, resulting in an intermediate of formula (XXII), followed in a next step by hydrogenating (H$_2$) said intermediate of formula (XXII) in the presence of a suitable catalyst, such as for example platinum on charcoal, and a suitable solvent, such as for example tetrahydrofuran, and an alcohol, e.g. methanol, resulting in an intermediate of formula (XXIII). In a next step, said intermediate of formula (XXIII) is reacted with an intermediate of formula (XIV) in the presence of a suitable base, such as for example NaHCO$_3$, and a suitable solvent, such as for example acetonitrile, resulting in an intermediate of formula (XXIV), which is deprotected in a next step in the presence of H$_2$, a suitable catalyst, such as for example palladium on charcoal, and a suitable solvent, such as for example an alcohol, e.g. methanol; or in the presence of a suitable acid, such as for example trifluoroacteic acid or HCl, and a suitable solvent, such as for example dichloromethane or dioxane; or in the presence of ammonium formate, a suitable catalyst, such as for example palladium on charcoal, and a suitable solvent, such as for example an alcohol, e.g. methanol.

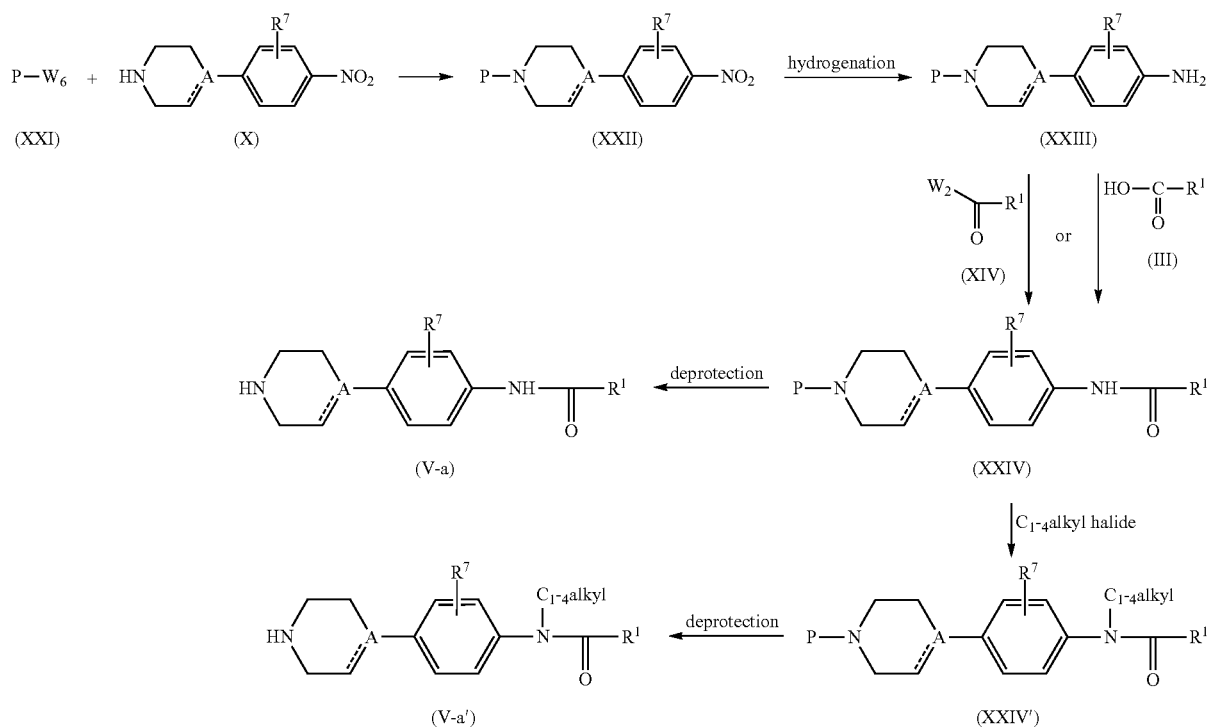

In the above reaction scheme, the intermediate of formula (XXIII) can also react with an intermediate of formula (III) in the presence of a suitable activating agent, such as for example SOCl$_2$ or Cl—C(=O)—C(=O)—Cl, a suitable base, such as for example N,N-diethyl-ethanamine or N,N-diisopropyl-ethanamine, and a suitable solvent, such as for example dichloromethane or N,N-dimethylformamide. Or an intermediate of formula (III) can react with an intermediate of formula (XXIII) in the presence of a suitable dehydrating (coupling) agent, such as for example N'-(ethylcarbonimidoyl)-N,N-dimethyl-1,3-propanediamine monohydrochloride (EDCI), dicyclohexylcarbodiimide (DCC), carbonyl diimidazole (CDI), 1-[bis(di-methylamino)methylene]-1H-benzotriazoliumhexafluorophosphate(1-)3-oxide (HBTU), 1-[bis(dimethyl-amino)methylene]-5-chloro-1H-benzotriazolium-hexafluorophosphate(1-)3-oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole, in the presence of a suitable solvent, such as for example N,N-dimethylformamide, dichloromethane, acetonitrile or tetrahydrofuran, and optionally in the presence of a suitable base, such as for example N,N-diisopropyl-ethanamine or N,N-diethyl-ethanamine.

The intermediate of formula (XXIV) can also react with an C$_{1-4}$alkyl halide, e.g. CH$_3$I, in the presence of a suitable base, such as for example NaH, and a suitable solvent, such as for example N,N-dimethylformamide, to form an intermediate of formula (XXIV') which can be deprotected according to the above described protocol to result in an intermediate of formula (V-a').

Intermediates of formula (V) wherein Y represents —C(=O)—NR$^x$—, said intermediates being represented by formula (V-b), can be prepared by reacting an intermediate of formula (XXX) wherein P represents a suitable protecting group, such as for example benzyl or tertiair butyloxycarbonyl, with an intermediate of formula (XXVI) in the presence of a suitable dehydrating (coupling) agent, such as for example N'-(ethylcarbonimidoyl)-N,N-dimethyl-1,3-propanediamine monohydrochloride (EDCI), dicyclohexylcarbodiimide (DCC), carbonyl diimidazole (CDI), 1-[bis(di-methylamino)methylene]-1H-benzotriazoliumhexafluorophosphate(1-)3-oxide (HBTU), 1-[bis(dimethyl-amino)methylene]-5-chloro-1H-benzotriazolium-hexafluorophosphate(1-)3-oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole, in the presence of a suitable solvent, such as for example N,N-dimethylformamide, dichloromethane, acetonitrile or tetrahydrofuran, and optionally in the presence of a suitable base, such as for example N,N-diisopropyl-ethanamine or N,N-diethyl-ethanamine, followed by deprotecting the resulting intermediate of formula (XXXI) with H$_2$, in the presence of a suitable catalyst, such as for example palladium on charcoal, and a suitable solvent, such as for example an alcohol, e.g. methanol, or by deprotection with a suitable acid, such as for example HCl, trifluoroacetic acid and the like, in the presence of a suitable solvent, such as for example an alcohol, e.g. isopropanol, or dichloromethane.

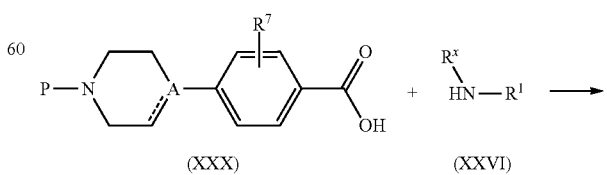

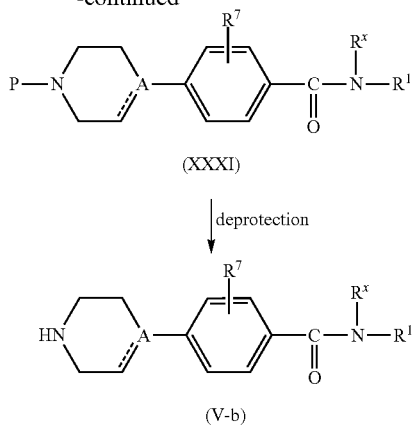

(XXXI)

↓ deprotection (V-b)

Intermediates of formula (IV) wherein $X_1$ represents a direct bond and $R^2$ contains a Het-$C_{1-4}$alkyl substituent, wherein Het represents a monocyclic, saturated N containing heterocycle represented by formula (XXXII), said intermediate of formula (IV) being represented by formula (IV-a), can be prepared by reacting an intermediate of formula (XXXII) with an intermediate of formula (XXXIII) in the represence of a suitable dehydrating (coupling) agent, such as for example N'-(ethylcarbonimidoyl)-N,N-dimethyl-1,3-propanediamine monohydrochloride (EDCI), dicyclohexyl-carbodiimide (DCC), carbonyl diimidazole (CDI), 1-[bis(dimethylamino)methylene]-1H-benzotriazoliumhexafluorophosphate(1-)3-oxide (HBTU), 1-[bis(dimethyl-amino)methylene]-5-chloro-1H-benzotriazolium-hexafluorophosphate(1-)3-oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole, in the presence of a suitable solvent, such as for example N,N-dimethylformamide, dichloromethane, acetonitrile or tetrahydrofuran, and optionally in the presence of a suitable base, such as for example N,N-diisopropyl-ethanamine or N,N-diethyl-ethanamine. The resulting intermediate of formula (XXXIV) can then be reduced in a next step in the presence of a suitable reducing agent, such as for example borane, in the presence of a suitable solvent, such as for example tetrahydrofuran, to an intermediate of formula (XXXV), which can then be converted into an intermediate of formula (IV-a) with phosgene in the presence of HCl in diethylether and a suitable solvent, such as for example toluene or acetonitrile.

Intermediates of formula (XXXIV) can also be converted into an intermediate of formula (IV-b) with phosgene in the presence of HCl in diethylether and a suitable solvent, such as for example toluene or acetonitrile or dichloromethane.

Intermediates of formula (IV-a) can also be prepared by reacting an intermediate of formula (XXXII) with an intermediate of formula (XXXVI) wherein $W_4$ represents a suitable leaving group, such as for example halo, e.g. chloro and the like, in the presence of a suitable solvent, such as for example acetonitrile, resulting in an intermediate of formula (XXXV') with can be converted into an intermediate of formula (IV-a) as described hereinabove for intermediate (XXXV).

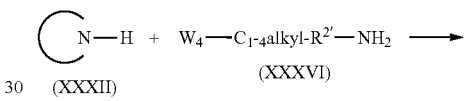

(XXXII)     (XXXVI)

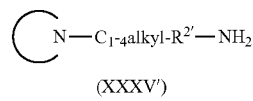

(XXXV')

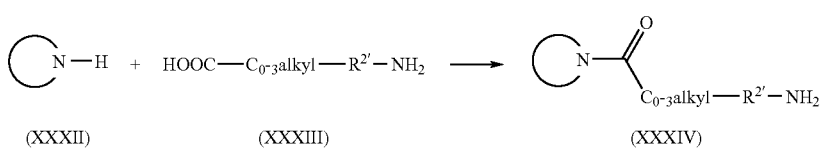

(XXXII)     (XXXIII)     (XXXIV)

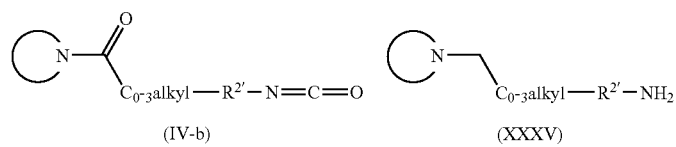

(IV-b)     (XXXV)

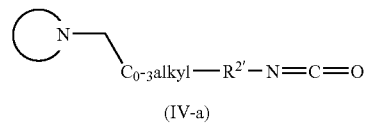

(IV-a)

Intermediates of formula (VII) can be prepared by hydrolysis of an intermediate of formula (XL) in the presence of LiOH, an acid, such as for example HCl, and a suitable solvent, such as for example an alcohol, e.g. methanol. Intermediates of formula (XL) wherein $R^2$ contains Het-$C_{1-4}$alkyl as substituent, said intermediates being represented by formula (XL-a) can be prepared by reacting an intermediate of formula (XLI) wherein $W_5$ represents a suitable leaving group, such as for example halo, e.g. bromo and the like, with an intermediate of formula (XXXII). Intermediates of formula (XLI-a) as depicted below, can be prepared by reacting an intermediate of formula (XLII) with N-bromosuccinimide in the presence of 2,2'-(1,2-diazenediyl)bis[2-methylpropanenitrile] and a suitable solvent, such as for example $CCl_4$. Intermediates of formula (XLII) wherein $X_1$ represents $CH_2$, said intermediates being represented by formula (XLII-a), can be prepared by reacting an intermediate of formula (XLV) with sodium metal, in the presence of a suitable $C_{1-4}$alkyl-OH, followed by adding a suitable acid, such as for example sulfuric acid. Intermediates of formula (XLV) can be prepared by reacting an intermediate of formula (IV'-a) with 1,1-dimethylethyl-nitrous acid ester, $CuCl_2$, 1,1-dichloroethene in a suitable solvent, such as for example acetonitrile.

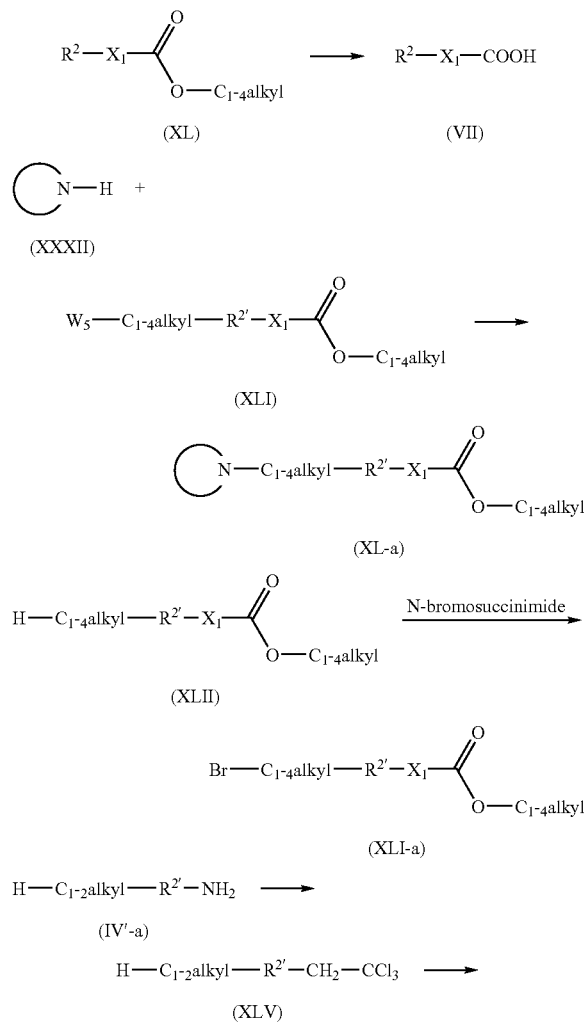

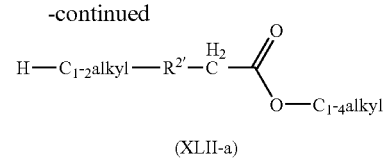

Intermediates of formula (XXV) wherein X represents $-X_1-HN-C(=O)-$, said intermediates being represented by formula (XXV-a), can be prepared by hydrolysis of an intermediate of formula (XXXVII) in the presence of a suitable base, such as for example sodium hydroxide, in the presence of a suitable solvent, such as for example dioxane. Intermediates of formula (XXXVII) can be prepared by reacting an intermediate of formula (IV) with an intermediate of formula (XXXVIII) in the presence of a suitable base, such as for example N,N-diethyl-ethanamine, and a suitable solvent, such as for example dichloromethane.

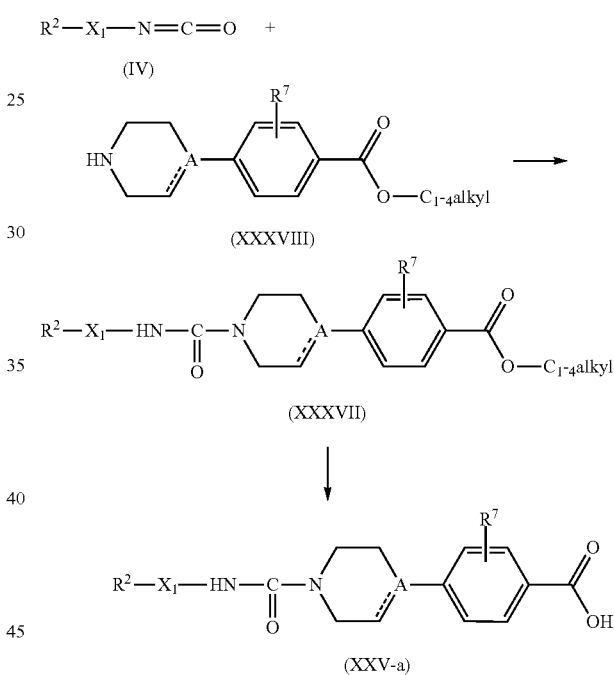

Intermediates of formula (XXV) wherein X represents $-X_1-C(=O)-$, said intermediates being represented by formula (XXV-b), can be prepared by hydrolysis of an intermediate of formula (XXXVII-a) in the presence of a suitable base, such as for example sodium hydroxide, in the presence of a suitable solvent, such as for example dioxane and optionally an alcohol, e.g. methanol. Intermediates of formula (XXXVII-a) can be prepared by reacting an intermediate of formula (IX) with an intermediate of formula (XXXVIII) in the presence of a suitable dehydrating (coupling) agent, such as for example N'-(ethylcarbonimidoyl)-N,N-dimethyl-1,3-propanediamine monohydrochloride (EDCI), dicyclohexylcarbodiimide (DCC), carbonyl diimidazole (CDI), 1-[bis(dimethylamino)methylene]-1H-benzotriazoliumhexafluorophosphate(1-) 3-oxide (HBTU), 1-[bis(dimethyl-amino)methylene]-5-chloro-1H-benzotriazolium-hexafluorophosphate(1-)-5-oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole, in the presence of a suitable solvent, such as for example N,N-dimethylformamide, dichloromethane, acetonitrile or tetrahydrofuran, and optionally in the presence of a suitable base, such as for example N,N-diisopropyl-ethanamine or N,N-diethyl-ethanamine.

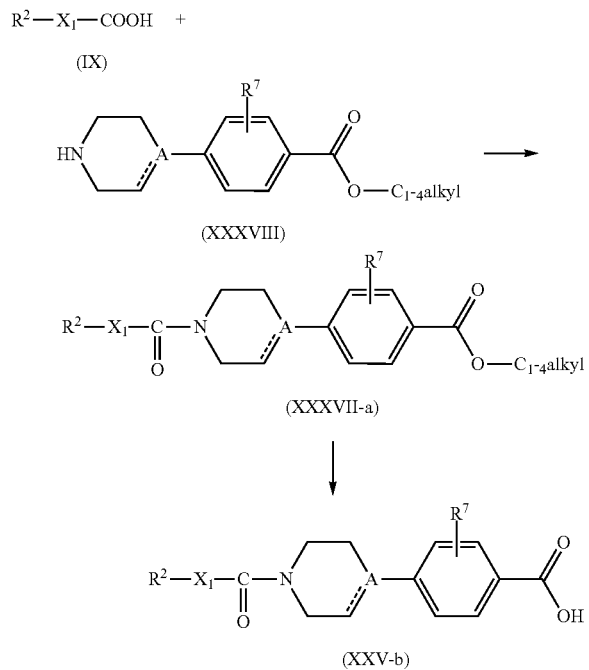

Intermediates of formula (XLIII-a) can be prepared according to the following reaction scheme. In a first step, an intermediate of formula (XLVI) wherein $W_{12}$ represents a suitable leaving group, such as for example fluoro, is reacted with 3,4-dihydro-2H-pyran in the presence of 4-methyl-benzenesulfonic acid and a suitable solvent, such as for example dichloromethane, resulting in an intermediate of formula (XLVII). Said intermediate is in a next step reacted with an intermediate of formula (XLVIII) wherein P represents a suitable leaving group, such as for example benzyl, in the presence of $Na_2CO_3$ and a suitable solvent, such as for example N,N-dimethylformamide resulting in an intermediate of formula (XLIX). In a next step, said intermediate is hydrogenated with $H_2$ in the presence of a suitable catalyst, such as for example platinum on charcoal, a catalyst poison, such as for example thiophene, and a suitable solvent, such as for example tetrahydrofuran, resulting in an intermediate of formula (L). This intermediate is then reacted with an intermediate of formula (III) in the presence of a suitable dehydrating (coupling) agent, such as for example N'-(ethylcarbonimidoyl)-N,N-dimethyl-1,3-propanediamine monohydrochloride (EDCI), dicyclohexylcarbodiimide (DCC), carbonyl diimidazole (CDI), 1-[bis(di-methylamino)methylene]-1H-benzotriazoliumhexafluorophosphate(1-)3-oxide (HBTU), 1-[bis(dimethyl-amino)methylene]-5-chloro-1H-benzotriazolium-hexafluorophosphate(1-)3-oxide (HCTU), O-benzotriazolyl tetramethylisouronium tetrafluoroborate (TBTU) or diethyl cyanophosphonate (DECP), optionally combined with hydroxy benzotriazole or chloro hydroxybenzotriazole, in the presence of a suitable solvent, such as for example N,N-dimethylformamide, dichloromethane, acetonitrile or tetrahydrofuran, and optionally in the presence of a suitable base, such as for example N,N-diisopropyl-ethanamine or N,N-diethyl-ethanamine. This reaction of an intermediate of formula (L) with an intermediate of formula (III) can also be performed in the presence of a suitable activating agent, such as for example Cl—C(=O)—C(=O)—Cl, a suitable base, such as for example N,N-diethyl-ethanamine, and a suitable solvent, such as for example N,N-dimethylformamide. This reaction can be performed as a fast synthesis reaction thereby using appropriate reagents well-known for fast synthesis, such as for example dicyclohexylcarbodiimide (DCC) linked to an appropriate carrier, e.g. polystyrene. Also for the purification of the reaction mixture, appropriate fast-synthesis reagents can be used, such as for example 1-ethenyl-4-(isocyanatomethyl)-benzene polymer with ethenylbenzene. In a next step, the intermediate of formula (LI) is deprotected with $H_2$, in the presence of a suitable catalyst, such as for example palladium on charcoal, a suitable base, such as for example N,N-diethyl-ethanamine, and a suitable solvent, such as for example tetrahydrofuran resulting in an intermediate of formula (LII) which can in a next step be reacted with an intermediate of formula (IV) in the presence of a suitable solvent, such as for example dichloromethane, to obtain an intermediate of formula (XLIII-a).

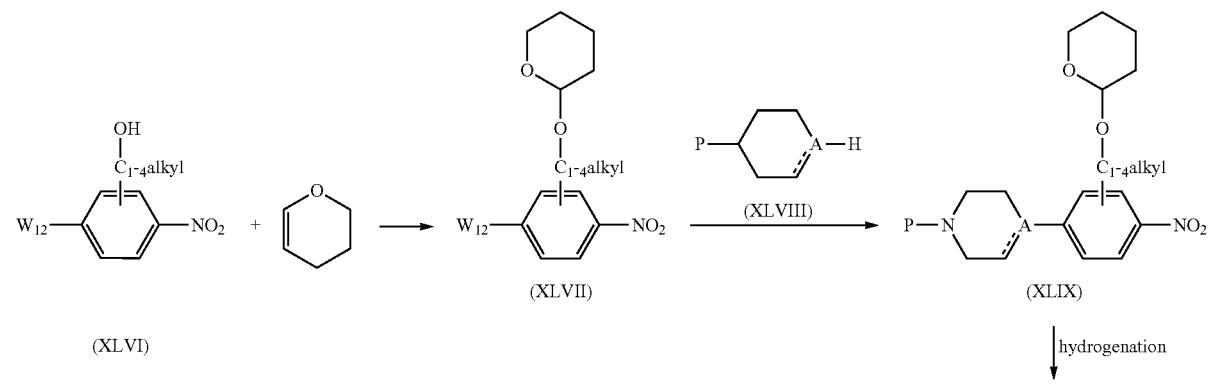

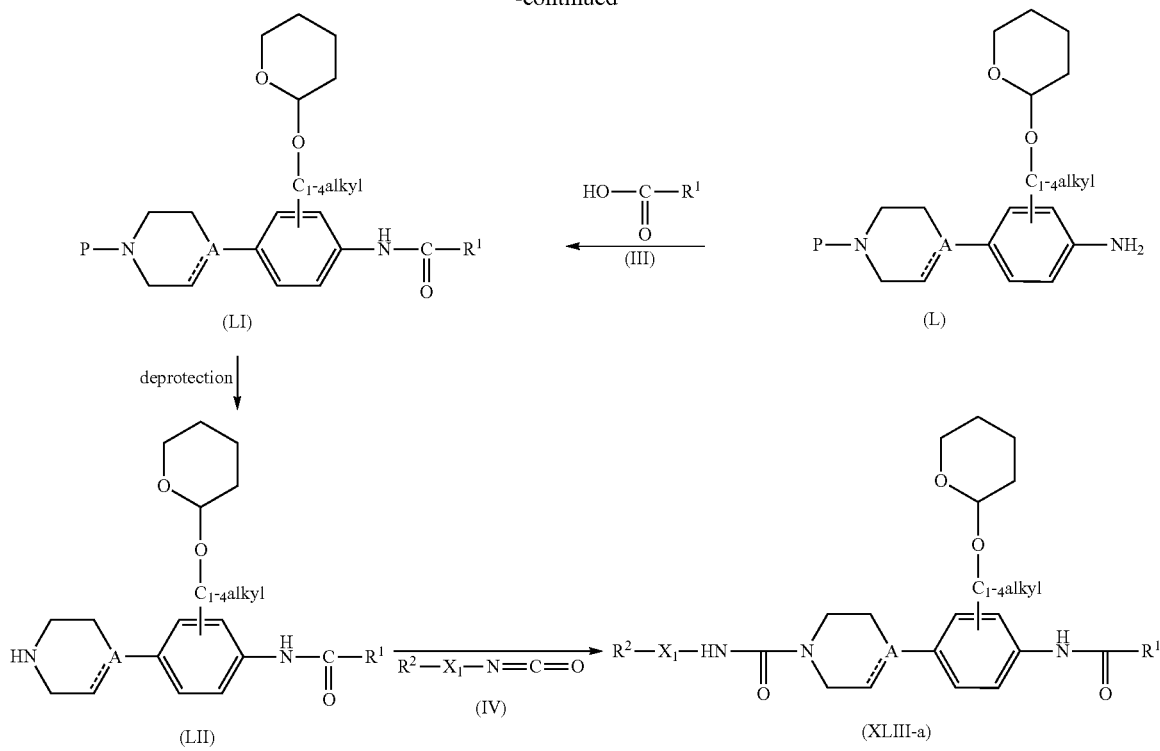

Intermediates of formula (XLIV-a) can be prepared by reacting an intermediate of formula (VII) wherein $X_1$ is substituted with a protected (P, such as for example tertair butyloxycarbonyl)amino group, said intermediate being represented by formula (VII-a), with an intermediate of formula (V) in the presence of a suitable dehydrating (coupling) agent, such as for example N'-(ethylcarbonimidoyl)-N,N-dimethyl-1,3-propanediamine monohydrochloride (EDCI), dicyclohexylcarbodiimide (DCC), carbonyl diimidazole (CDI), 1-[bis(di-methylamino)methylene]-1H-benzotriazolium-hexafluorophosphate(1-)3-oxide (HBTU), 1-[bis(dimethylamino)methylene]-5-chloro-1H-benzotriazolium-hexafluorophosphate(1-)3-oxide (HCTU), O-benzotriazolyl tetramethylisouronium tetrafluoroborate (TBTU) or diethyl cyanophosphonate (DECP), optionally combined with hydroxybenzotriazole or chloro hydroxybenzotriazole, in the presence of a suitable solvent, such as for example N,N-dimethylformamide, dichloromethane, acetonitrile or tetrahydrofuran, and optionally in the presence of a suitable base, such as for example N,N-diisopropyl-ethanamine or N,N-diethyl-ethanamine.

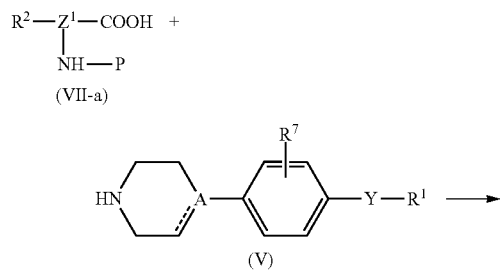

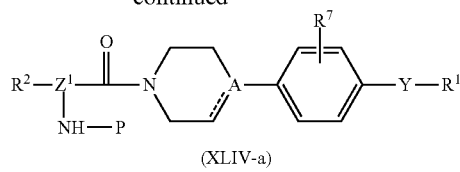

Intermediates of formula (VII) wherein $X_1$ represents CHOH, said intermediates being represented by formula (VII-b) can be prepared by reducing an intermediate of formula (LIII) in the presence of $ZnBr_2$, $Si(CH_3)_3$—CN and an acid, such as for example HCl, in the presence of a suitable solvent, such as for example dichloromethane. Intermediates of formula (LIII) can be prepared by reacting an intermediate of formula (LIV) wherein $W_{13}$ represents a suitable leaving group, such as for example halo, e.g. bromo and the like, with N,N-dimethylformamide in the presence of BuLi and a suitable solvent, such as for example tetrahydrofuran.

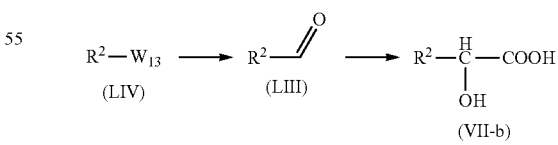

Pharmacological Part

As already indicated above, the present invention relates to the use of a DGAT inhibitor, in particular a DGAT1 inhibitor, to elevate levels of one or more satiety hormones, in particular GLP-1 levels. The present invention also relates to the use of a DGAT inhibitor, in particular a DGAT1 inhibitor, for the manufacture of a medicament for the prevention or the treatment, in particular for the treatment, of a disease which can benefit from an elevated level of one or more satiety hormones, in particular a disease which can benefit from an elevated GLP-1 level. In particular, GLP-1 levels are elevated in plasma or in portal blood, more in particular in plasma. By elevated GLP-1 levels, e.g. elevated GLP-1 plasma level or an elevated GLP-1 level in portal blood, it is meant that the GLP-1 level of a subject having taken a DGAT1 inhibitor is elevated or increased compared to the subject under the same conditions but not having taken the DGAT1 inhibitor. In particular GLP-1 levels are elevated in fasting conditions or postprandial, more in particular postprandial.

Therapeutic uses for a compound which elevates GLP-1 level include, but are not limited to, improving learning, enhancing neuro-protection, and/or alleviating a symptom of a disease or disorder of the central nervous system, e.g., through modulation of neurogenesis, and e.g., Parkinson's Disease, Alzheimer's Disease, Huntington's Disease, ALS, stroke, hemorrhage, cerebrovascular accident, ADD, and neuropsychiatric syndromes; converting liver stem/progenitor cells into functional pancreatic cells; preventing beta-cell deterioration and stimulation of beta-cell proliferation; treating pancreatitis; treating obesity; suppressing appetite and inducing satiety; treating irritable bowel syndrome or inflammatory bowel disease such as Crohn's disease and ulcerative colitis; reducing the morbidity and/or mortality associated with myocardial infarction and stroke; treating acute coronary syndrome characterized by an absence of Q-wave myocardial infarction; attenuating post-surgical catabolic changes; treating hibernating myocardium or diabetic cardiomyopathy; suppressing plasma blood levels of norepinepherine; increasing urinary sodium excretion, decreasing urinary potassium concentration; treating conditions or disorders associated with toxic hypervolemia, e.g., renal failure, congestive heart failure, nephrotic syndrome, cirrhosis, pulmonary edema, and hypertension; inducing an inotropic response and increasing cardiac contractility; treating polycystic ovary syndrome; treating respiratory distress; improving nutrition via a non-alimentary route, i.e., via intravenous, subcutaneous, intramuscular, peritoneal, or other injection or infusion; treating nephropathy; treating left ventricular systolic dysfunction, e.g., with abnormal left ventricular ejection fraction; inhibiting antro-duodenal motility, e.g., for the treatment or prevention of gastrointestinal disorders such as diarrhea, postoperative dumping syndrome and irritable bowel syndrome, and as premedication in endoscopic procedures; treating critical illness polyneuropathy (CIPN) and systemic inflammatory response syndrome (SIRS); modulating triglyceride levels and treating dyslipidemia; treating organ tissue injury (e.g. brain tissue injury) caused by reperfusion of blood flow following ischemia; improving the function of ischemic and reperfused brain tissue; treating coronary heart disease risk factor (CHDRF) syndrome. Further diseases which can benefit from an elevated GLP-1 level, include, but are not limited to, ischemic myocardial stunning; ishemic/reperfusion injury; acute myocardial infarction; left ventricular dysfunction; vascular disease; neuropathy, including periphere sensoric neuropathy associated with type II diabetes; bone-related disorders, including osteoporosis, obesity, diabetes. Because of the effect on GLP-1, the DGAT inhibitors can also be used to provide cardioprotection.

References supporting the above indications include Experimental Neurology, Vol. 203(2), pp 293-301 (2007); U.S. Pat. No. 7,186,683; J. Pharm. Exp. Ther. vol. 312, No. 1, pp 303-308 (2005); Diabetes, vol. 54, pp 146-151 (2005); US2007/0021339, which are incorporated herein by reference.

In view of the DGAT inhibitory activity, in particular the DGAT1 inhibitory activity, the present compounds of formula (I), their N-oxide forms, their pharmaceutically acceptable salts or their solvates, can be used as a medicine. In particular, the present invention relates to a compound of formula (I), a N-oxide form thereof, a pharmaceutically acceptable salt thereof or a solvate thereof for use as a medicine, in particular for use as a medicine for the prevention or the treatment of a disease which can benefit from an elevated GLP-1 level. In particular, the present invention also relates to the use of a compound of formula (I) for the manufacture of a medicament for the prevention or the treatment of a disease which can benefit from an elevated GLP-1 level, such as the diseases and disorders mentioned above.

In view of the above-described utility for a DGAT inhibitor, in particular a DGAT1 inhibitor, there is provided a method of treating a warm-blooded mammal, including a human, suffering from or a method of preventing a warm-blooded mammal, including a human, to suffer from a disease which can benefit from an elevated level of GLP-1, in particular a method of treating a warm-blooded mammal, including a human, suffering from a disease which can benefit from an elevated level of GLP-1. Said methods comprise the administration of an effective amount of a DGAT inhibitor, in particular a DGAT1 inhibitor, to a warm-blooded mammal, including a human.

In view of the DGAT inhibitory activity of the compounds of formula (I), there is provided a method of treating a warm-blooded mammal, including a human, suffering from or a method of preventing a warm-blooded mammal, including a human, to suffer from a disease which can benefit from an elevated level of GLP-1, in particular a method of treating a warm-blooded mammal, including a human, suffering from a disease which can benefit from an elevated level of GLP-1. Said methods comprise the administration of an effective amount of a compound of formula (I), a N-oxide form thereof, a pharmaceutically acceptable salt thereof or a solvate thereof, to a warm-blooded mammal, including a human.

In view of the DGAT inhibitory activity, in particular the DGAT1 inhibitory activity, the present invention also relates to a compound of formula (I), a N-oxide form thereof, a pharmaceutically acceptable salt thereof or a solvate thereof for use as a medicine, in particular for use as a medicine for the prevention or the treatment of a diseases which can benefit from inhibition of DGAT, in particular DGAT1. The invention also relates to the use of a compound of formula (I), a N-oxide form thereof, a pharmaceutically acceptable salt thereof or a solvate thereof, for the manufacture of a medicament for the prevention or the treatment of a disease or disorder which can benefit from inhibition of DGAT, in particular DGAT1. Diseases or disorders which can benefit from inhibition of DGAT, in particular DGAT1 include, but are not limited to metabolic disorders, such as obesity and obesity related disorders (including peripheral vascular disease, cardiac failure, myocardial ischaemia, cerebral ischaemia, cardiac myopathies), diabetes, in particular type II diabetes mellitus, and complications arising therefrom (such as retinopathy, neuropathy, nephropathy), syndrome X, insulin resistance, impaired glucose tolerance, conditions of impaired fasting glucose, hypoglycemia, hyperglycemia, hyperuricemia, hyperinsulinemia, pancreatitis, hypercholesterolemia, hyperlipidemia, dyslipidemia, mixed dyslipidemia, hypertriglyceridemia and nonalcoholic fatty liver disease, fatty liver, increased mesenteric fat, non-alcoholic steatohepatitis, liver fibrosis, metabolic acidosis, ketosis, dysmetabolic syndrome; dermatological conditions such as acne, psoriasis; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis and vascular stenosis; neoplastic diseases, such as solid tumors, skin cancer, melanoma, lymphoma and endothelial cancers, e.g., breast cancer, lung cancer, colorectal cancer, stomach cancer, other cancers of the gastrointestinal tract (e.g., esophageal cancer and pancreatic cancer), prostate cancer, kidney cancer, liver cancer, bladder cancer, cervical cancer, uterine cancer, testicular cancer and ovarian cancer; and other diseases and conditions that are sensitive or responsive to modulation, in particular inhibition, of DGAT function, in particular DGAT1 function.

Particular diseases or disorders which can benefit from inhibition of DGAT, in particular DGAT1, are selected from obesity, hypercholesterolemia, hyperlipidemia, dyslipidemia, mixed dyslipidemia, hypertriglyceridemia, fatty liver, nonalcoholic fatty liver disease, liver fibrosis, non-alcoholic steatohepatitis and diabetes, in particular type II diabetes.

In view of the DGAT inhibitory activity of the compounds of formula (I), there is provided a method of treating a warm-blooded mammal, including a human, suffering from or a method of preventing a warm-blooded mammal, including a human, to suffer from a disease which can benefit from inhibition of DGAT, in particular a method of treating a warm-blooded mammal, including a human, suffering from a disease which can benefit from inhibition of DGAT. Said methods comprise the administration of an effective amount of a compound of formula (I), a N-oxide form thereof, a pharmaceutically acceptable salt thereof or a solvate thereof, to a warm-blooded mammal, including a human.

The present invention also provides compositions for preventing or treating a disease which can benefit from an elevated GLP-1 level or which can benefit from inhibition of DGAT, in particular DGAT1, in particular for treating a disease which can benefit from elevated GLP-1 levels or which can benefit from inhibition of DGAT, in particular DGAT1. Said compositions comprise a therapeutically effective amount of a compound of formula (I), a N-oxide form thereof, a pharmaceutically acceptable salt thereof or a solvate thereof, and a pharmaceutically acceptable carrier.

The compounds of the present invention may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations, which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

The compounds of the present invention may also be topically administered in the form of drops, in particular eye drops. Said eye drops may be in the form of a solution or a suspension. Any system developed for the delivery of solutions or suspensions as eye drops are suitable for the administration of the present compounds.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will preferably comprise from 0.05 to 99% by weight, more preferably from 0.1 to 70% by weight, even more preferably from 0.1 to 50% by weight of the compound of formula (I), and, from 1 to 99.95% by weight, more preferably from 30 to 99.9% by weight, even more preferably from 50 to 99.9% by weight of a pharmaceutically acceptable carrier, all percentages being based on the total weight of the composition.

In view of the above described effects of DGAT inhibitors and/or the effect on GLP-1 levels by DGAT inhibitors, the present invention also relates to a) a combination of a DGAT inhibitor, in particular a DGAT1 inhibitor, more in particular a compound of formula (I), a N-oxide form thereof, a pharmaceutically acceptable salt thereof or a solvate thereof, and a dipeptidyl peptidase-4 inhibitor (DPP-4 inhibitor).

DPP-4 is a membrane-spanning cell surface aminopeptidase widely expressed in many tissues, such as liver, lung, kidney, intestinal brush-border membranes, lymphocytes, endothelial cells. DPP-4 cleaves peptides with a proline or alanine residue in the second aminoterminal position. Many gastro-intestinal hormones are substrates for DPP-4, among them GLP-1. A DPP-4 inhibitor thus inhibits cleavage of GLP-1 and hence provides for an increase in the level of GLP-1. Therefore, a combination as indicated above can be used to combine the activity of the DGAT inhibitor and the DPP4 inhibitor in order to elevate GLP-1 levels. By administering a DGAT inhibitor, in particular a DGAT1 inhibitor, more in particular a compound of formula (I), a N-oxide thereof, a pharmaceutically acceptable salt thereof or a solvate thereof, with a DPP4 inhibitor, different mechanisms may be targeted in order to achieve elevated levels of GLP-1. In this way, the use of such a combination may reduce the dosage of the DGAT inhibitor and the DPP4 inhibitor required for a desired elevation in GLP-1 level as compared to when the DGAT inhibitor or the DPP4 inhibitor is administered as a monotherapy. Therefore, these combinations may reduce or eliminate side effects of monotherapy while not interfering with the GLP-1 level increasing activity. Also, the combination of a DGAT inhibitor, in particular a DGAT1 inhibitor, more in particular a compound of formula (I), a N-oxide form thereof, a pharmaceutically acceptable salt thereof or a solvate thereof, and a DPP4 inhibitor can be used as a medicine. The present invention also relates to a product comprising (a) a DGAT inhibitor, in particular a DGAT1 inhibitor, more in particular a compound of formula (I), a N-oxide form thereof, a pharmaceutically acceptable salt thereof or a solvate thereof, and (b) a DPP4 inhibitor, as a combined preparation for simultaneous, separate or sequential use in the treatment of a disease which can benefit from an elevated level of GLP-1. The different drugs of such a combination or product may be combined in a single preparation together with pharmaceutically acceptable carriers or they may each be present in a separate preparation together with pharmaceutically acceptable carriers. Said DPP4 inhibitor which may be combined with a DGAT inhibitor according to the present invention, in particular a DGAT1 inhibitor, may be a known DPP4 inhibitor such as for example sitagliptin, vildagliptin, and saxagliptin.

b) a combination of a DGAT inhibitor, in particular a DGAT1 inhibitor, more in particular a compound of formula (I), a N-oxide form thereof, a pharmaceutically acceptable salt thereof or a solvate thereof, and a GLP-1 analogue. Said GLP-1 analogue can be considered as an agonist at the GLP-1 receptor.

Also, the combination of a DGAT inhibitor, in particular a DGAT1 inhibitor, more in particular a compound of formula (I), a N-oxide form thereof, a pharmaceutically acceptable salt thereof or a solvate thereof, and a GLP-1 analogue can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) a GLP-1 analogue, as a combined preparation for simultaneous, separate or sequential use in the treatment of a disease which can benefit from an elevated level of GLP-1. The different drugs of such a combination or product may be combined in a single preparation together with pharmaceutically acceptable carriers or they may each be present in a separate preparation together with pharmaceutically acceptable carriers.

Said GLP-1 analogue which may be combined with a DGAT inhibitor according to the present invention may be a known GLP-1 analogue such as for example exenatide, exenatide LAR or liraglutide.

c) a combination of a DGAT inhibitor, in particular a DGAT1 inhibitor, more in particular a compound of formula (I), a N-oxide form thereof, a pharmaceutically acceptable salt thereof or a solvate thereof, and an anti-diabeticum.

Also, the combination of a DGAT inhibitor, in particular a DGAT1 inhibitor, more in particular a compound of formula (I), a N-oxide form thereof, a pharmaceutically acceptable salt thereof or a solvate thereof, and an anti-diabeticum can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) an anti-diabeticum, as a combined preparation for simultaneous, separate or sequential use in the treatment of a disease which can benefit from an elevated level of GLP-1 or DGAT inhibition, such as for example diabetes, in particular type II diabetes. The different drugs of such a combination or product may be combined in a single preparation together with pharmaceutically acceptable carriers or they may each be present in a separate preparation together with pharmaceutically acceptable carriers. Said anti-diabeticum which may be combined with a DGAT inhibitor according to the present invention may be a known anti-diabeticum such as for example metformin, glibenclamide, rosiglitazon, pioglitazon, repaglinide, glimepiride, acarbose, glicazide, glipizide, nateglinide, tolbutamide, a protein tyrosine phosphatase 1 inhibitor, or a 11-beta-hydroxysteroid dehydrogenase inhibitor.

d) a combination of a DGAT inhibitor, in particular a DGAT1 inhibitor, more in particular a compound of formula (I), a N-oxide form thereof, a pharmaceutically acceptable salt thereof or a solvate thereof, and a phosphodiesterase (PDE) inhibitor, in particular a PDE10A or PDE11A inhibitor. Phosphodiesterase (PDE) inhibitors, in particular PDE10A or PDE11A inhibitors, are known to be insulin secretagogues, and to enhance the signalling of GLP-1 by inhibition of the hydrolysis of cAMP. Also, the combination of a DGAT inhibitor, in particular a DGAT1 inhibitor, more in particular a compound of formula (I), a N-oxide form thereof, a pharmaceutically acceptable salt thereof or a solvate thereof, and a phosphodiesterase (PDE) inhibitor, in particular a PDE10A or PDE11A inhibitor, can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) a phosphodiesterase (PDE) inhibitor, in particular a PDE10A or PDE11A inhibitor, as a combined preparation for simultaneous, separate or sequential use in the treatment of a disease which can benefit from an elevated level of GLP-1 or DGAT inhibition, such as for example diabetes, in particular type II diabetes, or obesity. The different drugs of such a combination or product may be combined in a single preparation together with pharmaceutically acceptable carriers or they may each be present in a separate preparation together with pharmaceutically acceptable carriers. Said phosphodiesterase (PDE) inhibitor, in particular a PDE10A or PDE11A inhibitor, which may be combined with a DGAT inhibitor according to the present invention may be a known PDE inhibitor such as for example papaverine, PQ-10, dipyridamole, ibudilast or tadalafil.

e) a combination of a DGAT inhibitor, in particular a DGAT1 inhibitor, more in particular a compound of formula (I), a N-oxide form thereof, a pharmaceutically acceptable salt thereof or a solvate thereof, and an appetite suppressant.

Also, the combination of a DGAT inhibitor, in particular a DGAT1 inhibitor, more in particular a compound of formula (I), a N-oxide form thereof, a pharmaceutically acceptable salt thereof or a solvate thereof, and an appetite suppressant can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) an appetite suppressant, as a combined preparation for simultaneous, separate or sequential use in the treatment of a disease which can benefit from an elevated level of GLP-1 or DGAT inhibition, such as for example diabetes, in particular type II diabetes, or obesity. The different drugs of such a combination or product may be combined in a single preparation together with pharmaceutically acceptable carriers or they may each be present in a separate preparation together with pharmaceutically acceptable carriers. Said appetite suppressants, which may be combined with a DGAT inhibitor according to the present invention may be a known appetite suppressant such as for example sibutramine and phentermine.

f) a combination of a DGAT inhibitor, in particular a DGAT1 inhibitor, more in particular a compound of formula (I), a N-oxide form thereof, a pharmaceutically acceptable salt thereof or a solvate thereof, and an anti-obesity drug with a CNS (central nervous system) mode of action such as for example a CB1 antagonist or inverse agonists.

Also, the combination of a DGAT inhibitor, in particular a DGAT1 inhibitor, more in particular a compound of formula (I), a N-oxide form thereof, a pharmaceutically acceptable salt thereof or a solvate thereof, and an anti-obesity drug with a CNS (central nervous system) mode of action can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) an anti-obesity drug with a CNS (central nervous system) mode of action, as a combined preparation for simultaneous, separate or sequential use in the treatment of a disease which can benefit from an elevated level of GLP-1 or DGAT inhibition, such as for example diabetes, in particular type II diabetes, or obesity. The different drugs of such a combination or product may be combined in a single preparation together with pharmaceutically acceptable carriers or they may each be present in a separate preparation together with pharmaceutically acceptable carriers. Said anti-obesity drugs with a CNS (central nervous system) mode of action, which may be combined with a DGAT inhibitor according to the present invention may be a known a anti-obesity drug such as for example Rimonabant, orlistat, SLV-319, or MK-0364.

g) a combination of a DGAT inhibitor, in particular a DGAT1 inhibitor, more in particular a compound of formula (I), a N-oxide form thereof, a pharmaceutically acceptable salt thereof or a solvate thereof, and an hypolipidemic drug such as for example 3-hydroxy-3-methyl-glutaryl coenzyme A (HMG-CoA) reductase inhibitors, squalene synthase inhibitors, FXR (farnesoid X receptor) and LXR (liver X receptor) ligands, cholestyramine, fibrates, nicotinic acid and aspirin.

Also, the combination of a DGAT inhibitor, in particular a DGAT1 inhibitor, more in particular a compound of formula (I), a N-oxide form thereof, a pharmaceutically acceptable salt thereof or a solvate thereof, and an hypolipidemic drug can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) an hypolipidemic drug, as a combined preparation for simultaneous, separate or sequential use in the treatment of a disease which can benefit from an elevated level of GLP-1 or DGAT inhibition, such as for example diabetes, in particular type II diabetes, or obesity. The different drugs of such a combination or product may be combined in a single preparation together with pharmaceutically acceptable carriers or they may each be present in a separate preparation together with pharmaceutically acceptable carriers. Said hypolipidemic drug which may be combined with a DGAT inhibitor according to the present invention may be a known hypolipidemic drug such as for example lovastatin, pravastatin, simvastatin, pravastatin, cerivastatin, mevastatin, velostatin, fluvastatin, dalvastatin, atorvastatin, rosuvastatin and rivastatin.

h) a combination of a DGAT inhibitor, in particular a DGAT1 inhibitor, more in particular a compound of formula (I), a N-oxide form thereof, a pharmaceutically acceptable salt thereof or a solvate thereof, and an agonist of peroxisome proliferator-activator receptor such as for example fenofibrate.

Also, the combination of a DGAT inhibitor, in particular a DGAT1 inhibitor, more in particular a compound of formula (I), a N-oxide form thereof, a pharmaceutically acceptable salt thereof or a solvate thereof, and an agonist of peroxisome proliferator-activator receptor such as for example fenofibrate, can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) an agonist of peroxisome proliferator-activator receptor such as for example fenofibrate, as a combined preparation for simultaneous, separate or sequential use in the treatment of a disease which can benefit from an elevated level of GLP-1 or DGAT inhibition, such as for example diabetes, in particular type II diabetes, or obesity. The different drugs of such a combination or product may be combined in a single preparation together with pharmaceutically acceptable carriers or they may each be present in a separate preparation together with pharmaceutically acceptable carriers.

i) a combination of a DGAT inhibitor, in particular a DGAT1 inhibitor, more in particular a compound of formula (I), a N-oxide form thereof, a pharmaceutically acceptable salt thereof or a solvate thereof, and an antihypertensive agent.

Also, the combination of a DGAT inhibitor, in particular a DGAT1 inhibitor, more in particular a compound of formula (I), a N-oxide form thereof, a pharmaceutically acceptable salt thereof or a solvate thereof, and an antihypertensive agent, can be used as a medicine. The present invention also relates to a product containing (a) a DGAT inhibitor, in particular a DGAT1 inhibitor, more in particular a compound of formula (I), a N-oxide form thereof, a pharmaceutically acceptable salt thereof or a solvate thereof, and (b) an antihypertensive agent, as a combined preparation for simultaneous, separate or sequential use in the treatment of a disease which can benefit from an elevated level of GLP-1 or DGAT inhibition, such as for example diabetes, in particular type II diabetes, or obesity. The different drugs of such a combination or product may be combined in a single preparation together with pharmaceutically acceptable carriers or they may each be present in a separate preparation together with pharmaceutically acceptable carriers. Said anti-hypertensive agent which may be combined with a DGAT inhibitor according to the present invention may be a known anti-hypertensive agent, e g loop diuretics such as ethacrynic acid, furosemide and torsemide, angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.

The following examples are intended to illustrate the present invention.

EXPERIMENTAL PART

Hereinafter, the term "m.p." means melting point, 'THF' means tetrahydrofuran, 'EtOAc' means ethyl acetate, 'MeOH' means methanol, 'DIPE' means diisopropyl ether, 'DMF' means N,N-dimethylformamide, 'Et$_3$N' means triethylamine, 'DPPENT' means 1,1'-(1,5-pentanediyl)bis[1,1'-diphenylphosphine], "resin-linked-N=C=O" means a polystyrene based resin functionalized with isocyanato-groups, such as for example 1-ethenyl-4-(isocyanatomethyl)-benzene polymer with ethenylbenzene, "PS-Carbodiimide" means polystyrene resin-bound N-cyclohexylcarbodiimide, "PS-NMM" means 3-(morpholino)propyl polystyrene sulfonamide (a resin-bound equivalent of N-methyl morpholine), "PS-TsOH" means polystyrene-para-toluenesulphonic acid, "PS-Trisamine" means tris-(2-aminoethyl)-aminomethyl polystyrene HL (200-400 mesh), "DECP" means diethyl cyanophosphonate, "Et$_2$O" means diethyl ether, "p.a." means pro analysis, "eq." means equivalent, "DIPEA" means diisopropylethylamine, "TFA" means trifluoroacetic acid, "TBTU" means O-benzotriazolyl tetramethylisouronium tetrafluoroborate, and "MP-carbonate" is macroporous triethylammonium methylpolystyrene carbonate (a macroporous polystyrene anion-exchange resin that is a resin-bound equivalent of tetraalkylammonium carbonate).

ArgoScoop™ resin (Biotage) dispenser is a variable volume resin scoop designed for convenient dispensing of polymer scavengers and reagents.

MiniBlock™ (Mettler Toledo) is a flexible, easy to use tool designed for parallel synthesis.

A. Preparation of the Intermediates

Example A1 a. Preparation of Intermediate 1

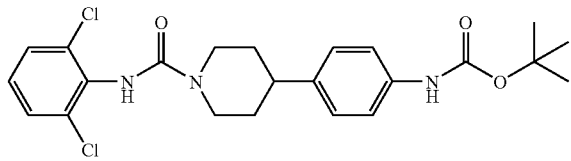 [SMILES: CC(C)(C)OC(=O)Nc1ccc(C2CCN(C(=O)Nc3c(Cl)cccc3Cl)CC2)cc1]

A mixture of [4-(4-piperidinyl)phenyl]carbamic acid 1,1-dimethylethylester (0.025 mol) in CH$_2$Cl$_2$ (100 ml) was stirred while cooling on an ice-bath. A solution of 1,3-dichloro-2-isocyanatobenzene (0.027 mol) in CH$_2$Cl$_2$ (25 ml) was added dropwise. The reaction mixture was allowed to warm to room temperature. The reaction mixture was stirred for one hour at room temperature. The resulting precipitate was filtered off, washed with DIPE and dried. Yield: 6.2 g of intermediate 1. The corresponding filtrate's solvent was evaporated. The residue was triturated under DIPE, filtered off and dried. Yield: 4.2 g of intermediate 1.

b. Preparation of Intermediate 2

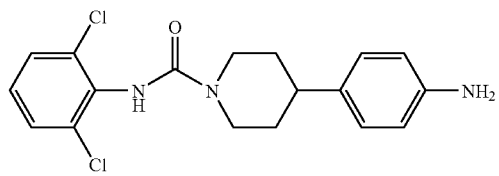

A mixture of intermediate 1 (prepared according to A1.a) (0.022 mol) and trifluoroacetic acid (25 ml) in CH$_2$Cl$_2$ (250 ml) was stirred for 2 hours at room temperature. The solvent was evaporated. The residue was triturated under DIPE, filtered off and dried. This fraction (11.2 g) was converted into the free base by adding aqueous ammonia. This mixture was extracted with CH$_2$Cl$_2$. The separated organic layer was dried, filtered and the solvent evaporated. Yield: 7.6 g of intermediate 2.

c. Preparation of Intermediate 3

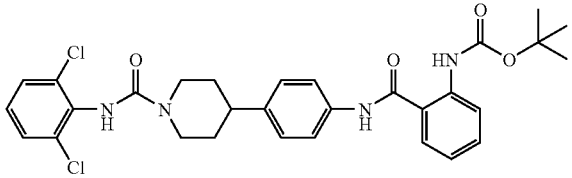 [SMILES: CC(C)(C)OC(=O)Nc1ccccc1C(=O)Nc1ccc(C2CCN(C(=O)Nc3c(Cl)cccc3Cl)CC2)cc1]

2-[[1,1-dimethylethoxy)carbonyl]amino]benzoic acid (0.001 mol) was dissolved in DMF (5 ml) to get stock solution (I). Part of stock solution (I) (1.2 ml, containing 0.00024 mol of 2-[[1,1-dimethylethoxy)carbonyl]amino]benzoic acid) was put into the MiniBlock. PS-Carbodiimide, 1.9 mmol/g (0.0004 mol) was added with ArgoScoop. A solution of 1-hydroxy-1H-benzotriazole (0.00030 mol) in DMF (1 ml) was added and the mixture was shaken for 30 minutes. A solution of intermediate 2 (prepared according to A1.b) (0.0002 mol) in DMF (3.5 ml) was added and the reaction mixture was shaken overnight. MP-carbonate, 2.8 mmol/g (0.00090 mol) and resin-linked-N=C=O, 1.8 mmol/g (0.0002 mol) were added with ArgoScoop. The reaction mixture was shaken overnight, then filtered. CH$_2$Cl$_2$ (4 ml) was added and the mixture was shaken for 2 hours. The mixture was filtered and the filtrate's solvent was evaporated (Genevac® solvent evaporator). The residue (±0.120 g) was purified by HPLC. The product fractions were collected and worked-up. Yield: 0.008 g of intermediate 3.

Example A2 a. Preparation of Intermediate 4

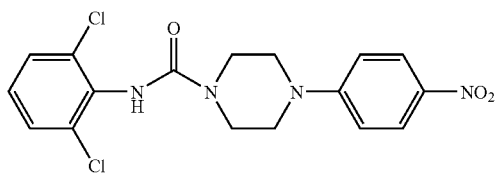 [SMILES: O=C(Nc1c(Cl)cccc1Cl)N1CCN(c2ccc([N+](=O)[O-])cc2)CC1]

A mixture of 1-(4-nitrophenyl)-piperazine (0.02413 mol) in CH$_2$Cl$_2$ p.a. (100 ml) was stirred on an ice bath. Then 1,3-dichloro-2-isocyanatobenzene (0.02660 mol) in CH$_2$Cl$_2$ p.a. (20 ml) was added dropwise while the reaction mixture was stirred on the ice bath. For 2 hours, the reaction mixture was let to warm up to room temperature and was stirred at room temperature. The reaction mixture was filtered off and washed with DIPE (q.s.). The precipitate was dried in vacuo. Yield: 8.923 g of intermediate 4 (94%; yellow powder)

b. Preparation of Intermediate 5

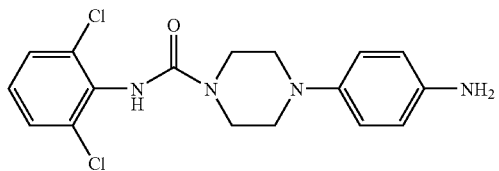 [SMILES: Nc1ccc(N2CCN(C(=O)Nc3c(Cl)cccc3Cl)CC2)cc1]

A mixture of intermediate 4 (prepared according to A2.a) (0.047 mol) in MeOH (200 ml), THF (200 ml) and NH$_3$ in MeOH (100 ml) was stirred for 15 minutes at room temperature and then hydrogenated at room temperature (atmospheric pressure) with Pt/C$_5$% (4 g) as a catalyst in the presence of thiophene solution (3 ml; 4% in DIPE). After uptake of H$_2$ (3 equiv), the catalyst was filtered off (product was also a precipitate and was therefore dissolved by washing the filter residue with CH$_2$Cl$_2$). The combined filtrate's solvent was evaporated. Yield: 14.616 g of intermediate 5.

Example A3 a. Preparation of Intermediate 6

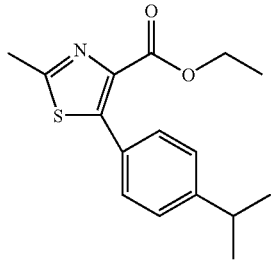 [SMILES: CCOC(=O)c1nc(C)sc1-c1ccc(C(C)C)cc1]

A mixture of 2-methyl-4-thiazolecarboxylic acid ethyl ester (0.1 mol), 1-iodo-4-(1-methylethyl)benzene (0.3 mol), KOAc (0.3 mol), Pd(OAc)$_2$ (0.005 mol) and DPPENT (0.001 mol) in 1-methyl-2-pyrrolidinone (150 ml) was stirred for 24 hours at 140° C. The reaction mixture was poured out into water and extracted four times with EtOAc. The organic layers were combined, washed twice with water, dried, filtered and the solvent evaporated. Yield: intermediate 6 (crude, used in next reaction step, without further purification).

b. Preparation of Intermediate 7

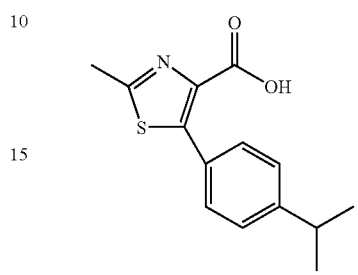

A mixture of intermediate 6 (prepared according to A3.a) (approximately 0.1 mol; crude) in H$_2$O (500 ml) and MeOH (500 ml) was stirred at room temperature. KOH (0.3 mol) was added portionwise and the reaction mixture was stirred over the weekend at room temperature. The solvent was evaporated. The residue was taken up into water. This mixture was washed 3× with CH$_2$Cl$_2$. The layers were separated. The aqueous phase was acidified until pH=3. The acidic mixture was extracted four times with CH$_2$Cl$_2$. The separated organic layer was dried, filtered and the solvent evaporated. The residue (21 g) was purified by HPLC (gradient elution with (NH$_4$OAc 0.5% in water/CH$_3$CN 90/10)/MeOH/CH$_3$CN). The product fractions were collected and the solvent was evaporated. The residue was taken up into water and acidified to pH=2-3. This mixture was extracted with CH$_2$Cl$_2$. The separated organic layer was dried, filtered and the solvent evaporated. The residue (10 g) was stirred in DIPE, filtered off and dried. Yield: Intermediate 7 (crude; used as such in the next reaction step).

Example A4 a. Preparation of Intermediate 8

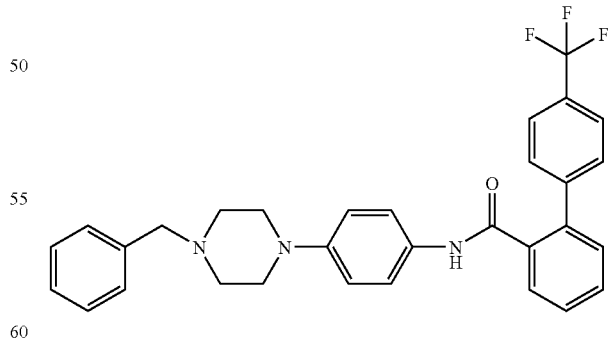

A mixture of 4-[4-(phenylmethyl)-1-piperazinyl]benzenamine (0.185 mol) in CH$_2$Cl$_2$ p.a. (1500 ml) and Et$_3$N (50 ml) was stirred on an ice-bath for 5 minutes. 4'-(trifluoromethyl)-[1,1'-biphenyl]-2-carbonyl chloride (0.37 mol) was added dropwise. The mixture was stirred for 3 hours. The organic layer was washed with water, dried, filtered and the solvent was evaporated. The residue was triturated in DIPE. The precipitate was filtered off and dried. Yield: 99.8 g of intermediate 8 (100%).

b. Preparation of Intermediates 9 and 10

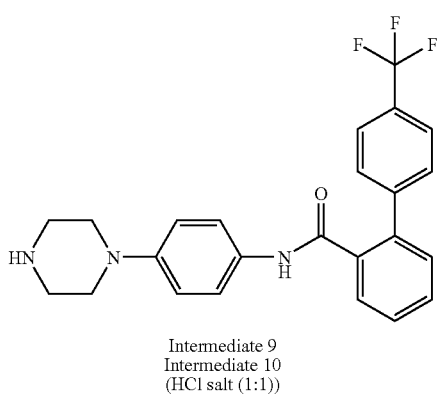 [SMILES: O=C(Nc1ccc(N2CCNCC2)cc1)c1ccccc1-c1ccc(C(F)(F)F)cc1]

Intermediate 9
Intermediate 10
(HCl salt (1:1))

A mixture of intermediate 8 (prepared according to A4.a) (0.19 mol) in MeOH (600 ml) and THF (600 ml) was hydrogenated overnight with Pd/C 10% (3 g) as a catalyst. After uptake of $H_2$ (1 equiv), the catalyst was filtered off and the filtrate was evaporated. The residue was triturated in DIPE. The precipitate was filtered off and dried. Yield: 76 g (94%). Part of the compound was converted into the HCl salt following art-known methods, yielding intermediate 10 (HCl-salt). (A part (1 g) of this fraction was recrystallized from 2-propanol. The precipitate was filtered off and dried. Yield: 0.36 g of intermediate 10.) The rest of the crude product was dissolved in $H_2O$. This mixture was alkalized with $Na_2CO_3$ and then extracted with $CH_2Cl_2$. The organic layer was separated, dried, filtered and the solvent was evaporated. The residue was triturated in DIPE. The precipitate was filtered off and dried. Yield: Intermediate 9.

Example A5 a. Preparation of Intermediate 11

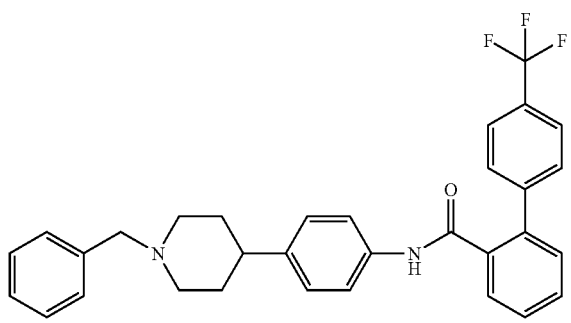 [SMILES: O=C(Nc1ccc(C2CCN(Cc3ccccc3)CC2)cc1)c1ccccc1-c1ccc(C(F)(F)F)cc1]

A mixture of [4'-(trifluoromethyl)-[1,1'-biphenyl]-2-carboxylic acid (0.09 mol) in $CH_2Cl_2$ (500 ml) and DMF (5 ml) was stirred. Ethanedioyl dichloride (0.09 mol) was added dropwise. The mixture was stirred for 1 hour (mixture A). 4-[1-(phenylmethyl)-4-piperidinyl]-benzenamine.hydrochloride (0.046 mol) in $CH_2Cl_2$ (500 ml) and $Et_3N$ (20 ml) was stirred on an ice-bath and this mixture was added drop-wise to mixture A. The reaction mixture was stirred and refluxed overnight, then cooled and washed with water. The organic layer was separated, dried, filtered and the solvent was evaporated. The residue was purified by column chromatography over silica gel (eluent: $CH_2Cl_2/CH_3OH$ 98/2). The desired product fractions were collected and the solvent was evaporated. The residue was triturated in DIPE. The precipitate was filtered off and dried. Yield: 5.6 g of intermediate 11.

b. Preparation of Intermediate 12

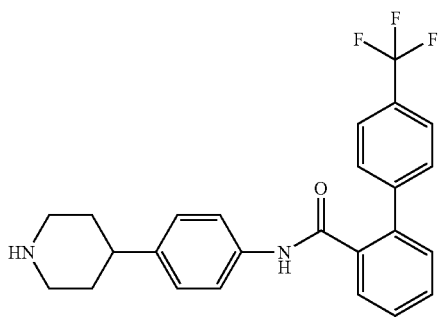 [SMILES: O=C(Nc1ccc(C2CCNCC2)cc1)c1ccccc1-c1ccc(C(F)(F)F)cc1]

A mixture of intermediate 11 (prepared according to A5.a) (0.025 mol) in $CH_3OH$ (250 ml) was hydrogenated at 50° C. overnight with Pd/C 10% (2 g) as a catalyst. After uptake of $H_2$ (1 equiv), the catalyst was filtered off and the filtrate was evaporated. The residue was triturated in DIPE. The precipitate was filtered off and dried. Yield: 7.7 g of intermediate 12 (73%).

Example A6 a. Preparation of Intermediate 13

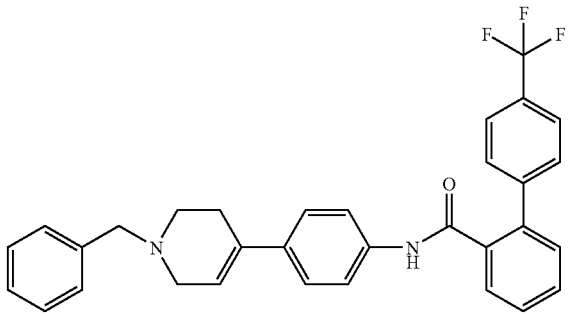 [SMILES: O=C(Nc1ccc(C2=CCN(Cc3ccccc3)CC2)cc1)c1ccccc1-c1ccc(C(F)(F)F)cc1]

[4'-(Trifluoromethyl)-1,1'-biphenyl]-2-carbonyl chloride (0.12 mol) was added dropwise to a stirring mixture of 4-[1,2,3,6-tetrahydro-1-(phenylmethyl)-4-pyridinyl]benzenamine (prepared according to the teachings in WO2002/081460, said content being incorporated herein by reference) (0.095 mol) in $CH_2Cl_2$ p.a. (300 ml) and $Et_3N$ (50 ml). The mixture was stirred overnight, poured out into water and then stirred for 30 minutes. The organic layer was separated, washed, dried, filtered and the solvent was evaporated. The residue was triturated in DIPE. The precipitate was filtered off and dried. Yield: 43 g (88%). A part (2 g) of this fraction was recrystallized from EtOH. The precipitate was filtered off and dried. Yield: 1.32 g of intermediate 13.

b. Preparation of Intermediate 14

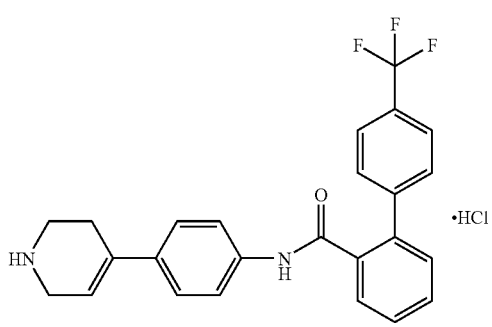 [SMILES: O=C(Nc1ccc(C2=CCNCC2)cc1)c1ccccc1-c1ccc(C(F)(F)F)cc1 ; Cl]

1-Chloroethyl chloroformate (0.078 mol) was added dropwise to a stirring mixture of intermediate 13 (prepared according to A6.a) (0.039 mol) in 1,2-dichloroethane (500 ml). The mixture was stirred for 30 minutes and then stirred and refluxed overnight. The solvent was evaporated. $CH_3OH$ (500 ml) was added. The mixture was stirred and refluxed overnight. The solvent was evaporated. The residue was triturated in DIPE. The precipitate was filtered off and dried. Yield: 20.8 g of intermediate 14 (HCl salt).

washed with water, dried, filtered and the solvent evaporated. Yield: intermediate 15 (crude; used as such in the next reaction step).

b. Preparation of Intermediate 16

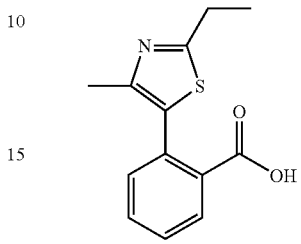

A mixture of intermediate 15 (prepared according to A7.a) (0.00765 mol) in THF (20 ml), $CH_3OH$ (20 ml) and NaOH, 1N (20 ml) was stirred for 16 hours at room temperature. The solvent was evaporated. The residue was taken up into water. This mixture was washed 3× with $CH_2Cl_2$. The layers were separated. The aqueous phase was acidified with 1 N HCl (20 ml). The acidic mixture was extracted with $CH_2Cl_2$. The separated organic layer was dried, filtered and the solvent evaporated. The residue was stirred in DIPE, filtered off and dried. Yield: 0.450 g of intermediate 16.

Example A7 a. Preparation of Intermediate 15

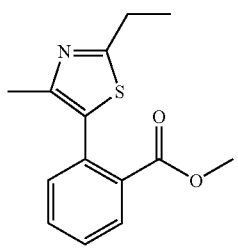

A mixture of 2-iodo-benzoic acid methyl ester (0.20 mol), 2-ethyl-4-methylthiazole (0.20 mol), $Pd(OAc)_2$ (1.120 g), 1,3-propanediylbis[diphenylphosphine] (4.120 g) and $Cs_2CO_3$ (65 g) in 1-methyl-2-pyrrolidinone (200 ml) was stirred for 36 hours at 140° C. More $Cs_2CO_3$ (32.5 g) and 2-iodo-benzoic acid methyl ester (0.1 mol) and catalyst was added and the reaction mixture was stirred for 16 hours at 140° C. The reaction mixture was poured out into water and extracted with EtOAc. The organic layers were combined, Example A8 a. Preparation of Intermediate 17

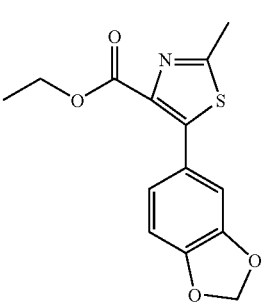 [SMILES: CCOC(=O)c1nc(C)sc1-c1ccc2c(c1)OCO2]

A mixture of 2-methyl-4-thiazolecarboxylic acid ethyl ester (0.054 mol), 5-bromo-1,3-benzodioxole (0.18 mol), $Pd(OAc)_2$ (1.041 g), 1,3-propanediylbis[diphenylphosphine] (3.831 g) and KOAc (18.6 g) in 1-methyl-2-pyrrolidinone (30 ml) was stirred for 16 hours at 140° C. The reaction mixture was poured out into water and extracted with EtOAc. The organic layers were combined, washed with water, dried, filtered and the solvent evaporated. Yield: Intermediate 17 (crude, used as such in the next reaction step).

b. Preparation of Intermediate 18

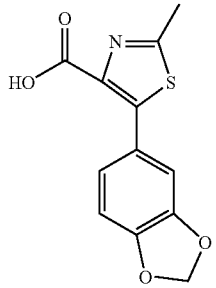 [SMILES: Cc1nc(C(=O)O)c(-c2ccc3c(c2)OCO3)s1]

A mixture of intermediate 17 (prepared according to A8.a) (0.054 mol) in CH$_3$OH (100 ml) and NaOH, 1 N (100 ml) was stirred for 16 hours at room temperature. The solvent was evaporated. The residue was taken up into water. This mixture was washed 3 times with CH$_2$Cl$_2$. The layers were separated. The aqueous phase was neutralized with 1N HCl (100 ml). The mixture was extracted with CH$_2$Cl$_2$ (3 times). The separated organic layer was dried, filtered and the solvent evaporated. Yield: 2.5 g of intermediate 18.

Intermediate

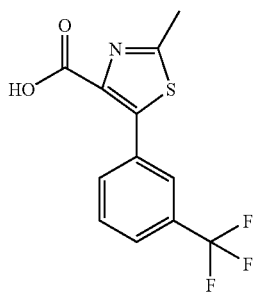 [SMILES: Cc1nc(C(=O)O)c(-c2cccc(C(F)(F)F)c2)s1]

2-methyl-5-(3-trifluoromethyl-phenyl)-thiazole-4-carboxylic acid was made accordingly (see B1.b)

Example A9 a. Preparation of Intermediate 19

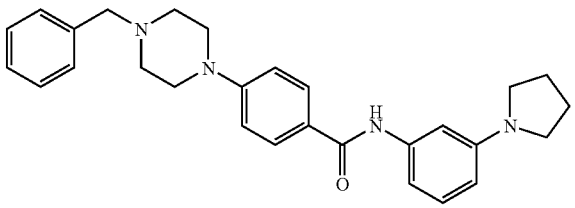 [SMILES: O=C(Nc1cccc(N2CCCC2)c1)c1ccc(N2CCN(Cc3ccccc3)CC2)cc1]

3-Pyrrolidin-1-ylaniline (8 g, 0.0478 mol) was dissolved in CH$_2$Cl$_2$ (50 ml). First Et$_3$N (25 ml, 0.178 mol) and then 4-[4-(phenylmethyl)-1-piperazinyl]-benzoic acid (11.27 g, 0.038 mol) and more CH$_2$Cl$_2$ (100 ml) were added. Finally, DECP (11.37 ml, 0.0761 mol) was added and the reaction mixture was stirred for 18 hours. Subsequently, the mixture was stirred in a NaHCO$_3$ solution. The layers were separated and the organic layer was dried (MgSO$_4$), filtered and the solvent was evaporated and co-evaporated with toluene. The residue was purified by column chromatography over silica gel (eluent: CH$_2$Cl$_2$/MeOH 98/2). The purest fractions were collected and the solvent was evaporated. The residue was stirred in Et$_2$O, filtered off and washed (Et$_2$O). The product was dried (50° C., 48 hours, in vacuo). Yield: 9.437 g of intermediate 19 (55%).

b. Preparation of Intermediate 20

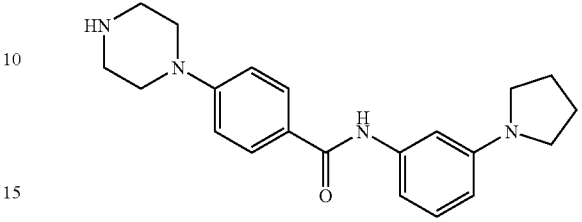

Pd/C 10% (1 g) was suspended in MeOH (150 ml) under N$_2$ flow. Intermediate 19 (5.62 g, 0.0126 mol) was added and the reaction mixture was stirred at 50° C. under H$_2$ atmosphere until 1 eq. of H$_2$ was absorbed. The catalyst was filtered off over diatomaceous earth (Dicalite®). The solvent was evaporated and co-evaporated with toluene. The residue was stirred in Et$_2$O and filtered off. The product was dried (50° C., 18 hours, in vacuo). Yield: 4.23 g of intermediate 20 (96%).

Example A10 a. Preparation of Intermediate 21

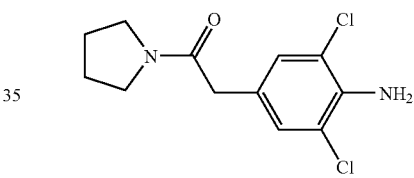

CH$_2$Cl$_2$ (75 ml) was added to 4-amino-3,5-dichloro-benzeneacetic acid (2.86 g, 0.013 mol) and the mixture was stirred. Et$_3$N (5.5 ml, 0.0391 mol) and pyrrolidine (1.3 ml, 0.0158 mol) were added. Finally DECP (2.5 ml, 0.015 mol) was added. The reaction mixture was set under N$_2$ flow for a few minutes and then the vessel was closed. After 18 hours, a NaHCO$_3$ solution was added and the layers were separated. The separated organic layer was dried (MgSO$_4$), filtered and the solvent was evaporated and co-evaporated with toluene. The residue (4.317 g) was purified by column chromatography over silica gel (eluent: CH$_2$Cl$_2$/MeOH 97/3). The desired fractions were collected and the solvent was evaporated and co-evaporated with toluene. Yield: 3.104 g of intermediate 21 (88%).

b. Preparation of Intermediate 22

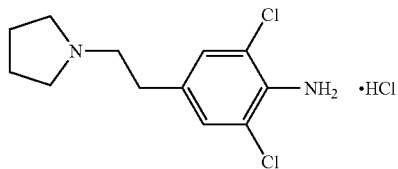 [SMILES: Nc1c(Cl)cc(CCN2CCCC2)cc1Cl ; Cl]

A solution of borane in THF (30 ml, 0.03 mol; 1 M solution) was added to intermediate 21 (2.88 g, 0.0105 mol) in THF (60 ml; dry) and the reaction mixture was refluxed for 18 hours. Subsequently, the mixture was cooled to room temperature and the mixture was added to a stirring solution of H₂O (300 ml) and concentrated HCl (300 ml) on an ice-bath. This mixture was refluxed for 30 minutes. Then, the mixture was cooled, was put on an ice-bath, and K₂CO₃ powder was added slowly to alkalize the mixture. At pH 8, CH₂Cl₂ and H₂O were added to the mixture (for an extraction). The layers were separated. The organic layer was dried (MgSO₄), filtered and the solvent evaporated and co-evaporated with toluene. The residue was stirred in Et₂O and this mixture was extracted twice with HCl (1 N). The HCl layers were combined, neutralized with (NaHCO₃) until pH 8 and extracted with CH₂Cl₂ and H₂O. The layers were separated and the organic layer was dried (MgSO₄), filtered and the solvent was evaporated and co-evaporated with toluene. The residue was dried (50° C., 18 hours, in vacuo). The product was stirred in Et₂O with HCl/Et₂O (15 ml; 1 M). The product was filtered off and washed with Et₂O to yield 3.05 g of intermediate 22 (98%; .HCl).

c. Preparation of Intermediate 23

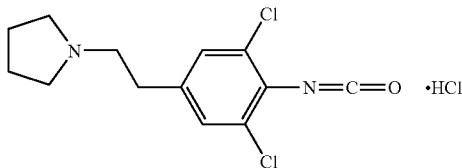 [SMILES: O=C=Nc1c(Cl)cc(CCN2CCCC2)cc1Cl ; Cl]

Intermediate 22 (3 g, 0.0101 mol) was dissolved in a solution of HCl in Et₂O (10 ml, 0.01 mol; 1 M solution) and CH₃CN (150 ml; dry) at room temperature. The mixture was stirred for 30 minutes. 20% Phosgene in toluene (7.6 ml, 0.0152 mol) was added portionwise and the mixture was stirred for 20 hours. The mixture was filtered and the turbid filtrate was evaporated and co-evaporated with toluene (dry) to yield 2.89 g of the crude intermediate 23 (quantitative yield; HCl salt).

Example A11 a. Preparation of Intermediate 24 and 25

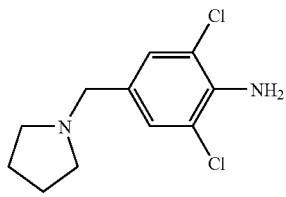

Intermediate 24 (free base)
Intermediate 25 (•HCl)

2,6-Dichloro-4-chloromethyl-phenylamine (11 g, 0.0445 mol) was added portionwise to a stirring solution of pyrrolidine (15.84 g, 0.223 mol) in CH₃CN (250 ml). The reaction mixture was placed in a water bath (exothermic reaction). The solvent was evaporated and the residue was dissolved in CH₂Cl₂ (150 ml) and a 50% saturated NaHCO₃ solution (100 ml). The mixture was stirred for 15 minutes. The organic layer was separated, dried (MgSO₄), filtered and the solvent was evaporated and co-evaporated with toluene. The oily residue (11.46 g) was stirred in DIPE (30 ml) for 15 minutes and then the DIPE was evaporated again. The residue was combined with 2.65 g of another batch and the total amount of crude product was purified by column chromatography over silicagel (eluent: CH₂Cl₂/MeOH 95/5). The pure fractions were combined and the solvent was evaporated and co-evaporated with toluene. The residue was stirred in DIPE (25 ml). The DIPE was decanted from the solid, yielding a DIPE layer (*) and a solid. The remaining DIPE on the solid was evaporated and the solid was dried (50° C., in vacuo), yielding 2.75 g of intermediate 24 (28.18%). The impure fractions from the column were combined and the solvent was evaporated and co-evaporated with toluene. The residue (7.45 g) was dissolved in DIPE (20 ml) and 6N HCl in 2-propanol (5 ml) was added while the mixture was stirred vigorously. A yellowish oil was formed that became solid after continuous stirring. The solid was filtered off and washed with DIPE, yielding a filtrate (*) and a solid. The solid was dried (50° C., in vacuo). Yield: 5.19 g of intermediate 25 (41.37%; .HCl). The filtrate (*) and the DIPE layer (*) were combined and the solvent was evaporated. The residue (2.59 g) was dissolved in CH₂Cl₂ and NaHCO₃ in H₂O. The layers were separated and the organic layer was dried (MgSO₄), filtered and the solvent was partially evaporated. The concentrated solution was re-purified over silicagel (eluent: CH₂Cl₂/MeOH 95/5). The pure fractions were collected and the solvent was evaporated and co-evaporated with toluene. The residue was dried (50° C., 18 hours, in vacuo). Yield: 1.85 g of intermediate 24 (17%).

b. Preparation of Intermediate 26

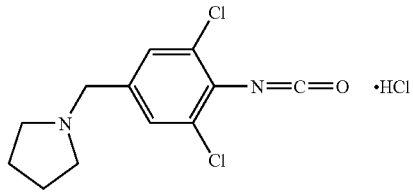 [SMILES: O=C=Nc1c(Cl)cc(CN2CCCC2)cc1Cl ; Cl]

HCl in Et₂O (10.32 ml, 0.0206 mol; 1 M) was added to a stirring solution of intermediate 24 (4.6 g, 0.0188 mol) in CH₃CN (75 ml; p.a. dried on molecular sieves) and CH₂Cl₂ (10 ml; p.a.). The mixture was stirred for 1 hour. A precipitate was formed. The reaction mixture was cooled on an ice-bath, and 20% phosgene in toluene (14.073 ml) was added. The reaction mixture was stirred for 3 hours. An additional amount of 20% phosgene in toluene (7 ml) was added, and the reaction mixture was stirred further at room temperature for 18 hours. The product was filtered off, washed with CH₃CN (3×) and dried (50° C., 1 hour, in vacuo), yielding 5.45 g of intermediate 26 (94%; .HCl). This intermediate was immediately used in the next reaction step (hygroscopic intermediate).

c-1. Preparation of Intermediate 27

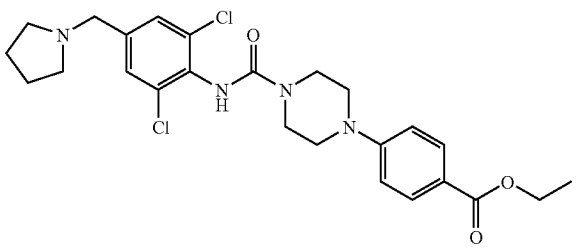 [SMILES: CCOC(=O)c1ccc(N2CCN(C(=O)Nc3c(Cl)cc(CN4CCCC4)cc3Cl)CC2)cc1]

1-(4-Ethoxycarbonylphenyl)piperazine (3.732 g, 0.0159 mol) was added to a stirring mixture of intermediate 26 (4.9 g, 0.0159 mol) and CH$_2$Cl$_2$ (100 ml). Et$_3$N (4.478 ml) was added and the solution was stirred at room temperature for 18 hours. Then, the mixture was washed with a saturated aqueous NaHCO$_3$ solution, dried (MgSO$_4$), filtered and the solvent was evaporated. The residue was stirred in Et$_2$O and the solid was filtered off, washed with Et$_2$O (3×) and dried (50° C., in vacuo). Yield: 6.55 g of intermediate 27 (81%).

c-2. Preparation of Intermediate 37

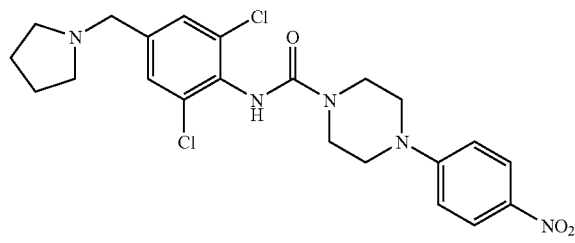 [SMILES: O=C(Nc1c(Cl)cc(CN2CCCC2)cc1Cl)N1CCN(c2ccc([N+](=O)[O-])cc2)CC1]

Intermediate 26 (approximately 24 mmol, crude) was added portionwise to a stirring solution of 1-(4-nitrophenyl)piperazine (5 g, 24 mmol) in Et$_3$N (10 ml, 7.2 mmol) and CH$_2$Cl$_2$ (125 ml; p.a.) (temperature reached approximately 30° C.). The reaction mixture was stirred for 4 hours at room temperature and was then washed with H$_2$O. The separated organic layer was dried (MgSO$_4$), filtered and the solvent was evaporated. The residue was filtered over silica (eluent: CH$_2$Cl$_2$/MeOH 96/4). The purest fractions were combined and the solvent was evaporated and co-evaporated with toluene. The residue was stirred in DIPE, filtered off and dried (50° C., in vacuo). Yield: 2.9 g of intermediate 37.

d-1. Preparation of Intermediate 28

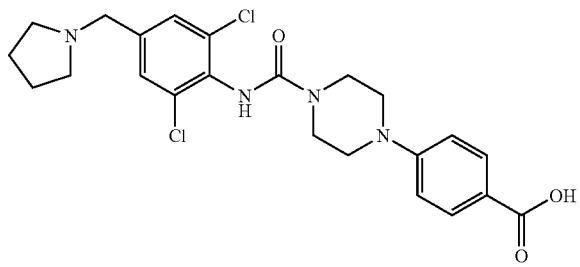 [SMILES: O=C(O)c1ccc(N2CCN(C(=O)Nc3c(Cl)cc(CN4CCCC4)cc3Cl)CC2)cc1]

Intermediate 27 (5.88 g, 0.0116 mol) was added to 1,4-dioxane (75 ml) and the mixture was stirred. A NaOH solution (35 ml, 0.035 mol; 1 M) was added and the mixture was stirred for 72 hours at room temperature. Subsequently, MeOH (25 ml) was added and the mixture was stirred again for 72 hours. Then HCl (35 ml; 1 N) was added and the mixture was stirred for 18 hours. The solid was filtered off and washed with H$_2$O. The solid was dried (50° C., 24 hours, in vacuo). Yield: 4.88 g of intermediate 28 (88%).

d-2. Preparation of Intermediate 38

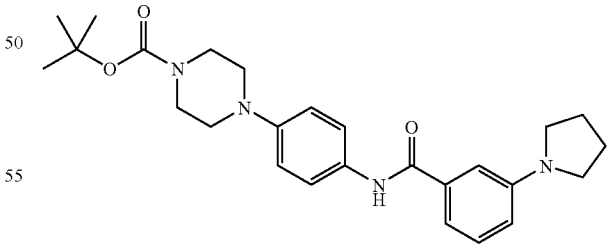

A solution of intermediate 37 (2.19 g, 0.00458 mol) in acetic acid (125 ml) was hydrogenated with Pt/C$_5$% (0.5 g) as a catalyst in the presence of a thiophene solution (0.3 ml; 4% in DIPE). After 3 eq. of H$_2$ were taken up, the catalyst was filtered off. The solvent was evaporated (water bath at 40° C.). The residue was stirred in CH$_2$Cl$_2$ and this solution was washed with a half saturated aqueous NaHCO$_3$ solution. The organic layer was dried (MgSO$_4$), filtered and the solvent was evaporated. The residue was purified over silicagel (eluent: CH$_2$Cl$_2$/MeOH 93/7). The desired fractions were combined and the solvent was evaporated and co-evaporated with toluene, yielding intermediate 38.

Example A12 a. Preparation of Intermediate 29

DECP (12.5 ml, 0.0836 mol) was added to a stirring solution of 1-tert-butoxycarbonyl-4-(4-aminophenyl)piperazine (15.12 g, 0.0545 mol) and 3-(1-pyrrolidinyl)benzoic acid (11.47 g, 0.06 mol) in Et$_3$N (23 ml, 0.164 mol) and CH$_2$Cl$_2$ (200 ml) at room temperature. After 20 hours, a saturated NaHCO$_3$ solution was added and the layers were separated. The CH$_2$Cl$_2$ layer was dried (MgSO$_4$), filtered and the solvent was evaporated and co-evaporated with toluene. The residue was stirred in Et₂O, filtered off, washed with E₂O and dried (50° C., 20 hours, in vacuo). Yield: 24.682 g of intermediate 29 (90%).

b. Preparation of Intermediate 30

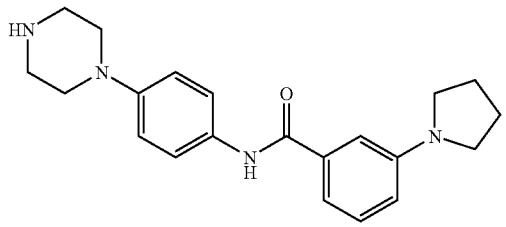 [SMILES: O=C(Nc1ccc(N2CCNCC2)cc1)c1cccc(N2CCCC2)c1]

TFA (25 ml) was added to a stirring solution of intermediate 29 (15 g, 0.03 mol) in CH₂Cl₂ (50 ml) at room temperature. After 18 hours, the solvent was evaporated. The residue was stirred in H₂O and CH₂Cl₂ and neutralized with Na₂CO₂ powder and NaHCO₃ until the mixture was alkaline. The reaction mixture was stirred for 48 hours. Then, the layers were separated. The organic layer was dried (MgSO₄), filtered and the solvent was evaporated and co-evaporated with toluene. The residue was stirred in DIPE, filtered off and dried (50° C., 18 hours, in vacuo). Subsequently, the product was refluxed in CH₃CN. The mixture was cooled to room temperature and the solid was filtered off and dried (50° C., 18 hours, in vacuo). Yield: 8.580 g of intermediate 30 (75%).

Example A13 a. Preparation of Intermediate 31

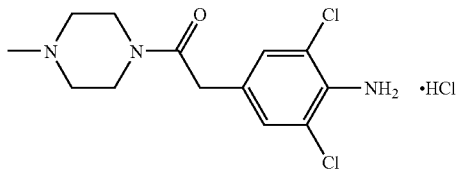 [SMILES: CN1CCN(C(=O)Cc2cc(Cl)c(N)c(Cl)c2)CC1 ; Cl]

CH₂Cl₂ (25 ml) was added to 4-amino-3,5-dichloro-benzeneacetic acid (0.754 g, 0.00343 mol) and the mixture was stirred. Et₃N (1.45 ml, 0.0103 mol) and 1-methylpiperazine (0.46 ml, 0.00415 mol) were added. DECP (0.65 ml, 0.00391 mol) was added and the mixture was flushed with N₂ and closed off. The reaction mixture was stirred for 72 hours at room temperature. Subsequently, the mixture was stirred in a saturated solution of NaHCO₃ in H₂O and the layers were separated. The organic layer was dried (MgSO₄), filtered and the solvent was evaporated and co-evaporated with toluene. The residue was stirred in CH₂Cl₂ and a saturated aqueous K₂CO₃ solution. The layers were separated (an extra amount of H₂O was added for good separation). The CH₂Cl₂ layer was dried (MgSO₄), filtered and the solvent was evaporated and co-evaporated with xylene. The residue was dissolved in DIPE and HCl/2-propanol (3 ml; 6 N) was added. The mixture was stirred for 15 hours and then the solid was filtered off, washed with DIPE and dried (50° C., 1 hour, in vacuo). Yield: 1.3 g of intermediate 31 (99%; .HCl).

b. Preparation of Intermediate 32

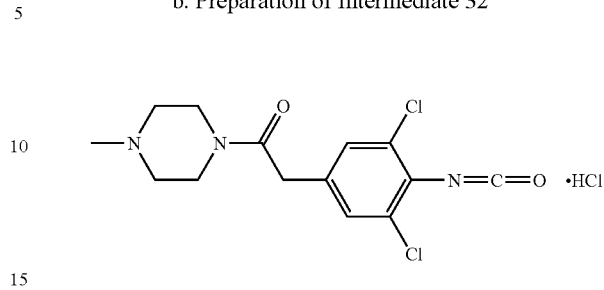

Intermediate 31 (1.3 g, 0.00384 mol) was dissolved in HCl in Et₂O (4.2 ml, 0.0042 mol; 1 M solution) and CH₃CN (20 ml; dry) at 0° C. A 20% phosgene solution in toluene (5.8 ml, 0.0116 mol) was added while stirring. After 2 hours, the ice-bath was removed and the mixture was stirred at room temperature for 50 hours. An extra amount of the 20% phosgene solution in toluene (1.92 ml) was added and the mixture was stirred for 36 hours. Then a third amount of the 20% phosgene solution in toluene (1 ml) was added and the mixture was stirred for 18 hours. The solvent was evaporated and co-evaporated with dry toluene. The residue (1 g crude intermediate 32; quantitative yield; HCl-salt) was directly used as such in the next reaction step.

Example A14 a. Preparation of Intermediate 33 and 33'

Intermediate 33

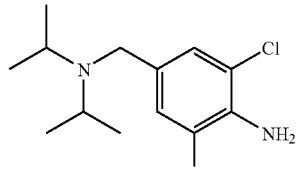

Intermediate 33'

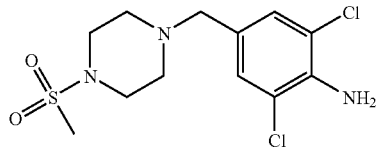

2,6-Dichloro-4-chloromethyl-phenylamine (3.68 g, 0.0149 mol) was added portionwise to a stirred solution of 1-mesylpiperazine (2.971 g, 0.0181 mol) and diisopropylamine (8.2 ml, 0.058 mol) in CH₃CN (100 ml) on a water bath. The reaction mixture was stirred for 18 hours at room temperature. The product was purified by reversed phase high-performance liquid chromatography (Shandon Hyperprep® C18 BDS (Base Deactivated Silica) 8 μm, 250 g, I.D. 5 cm). A gradient with 3 mobile phases was applied. Phase A: 90% of a 0.5% NH₄OAc solution in water+10% CH₃CN; phase B: CH₃OH; phase C: CH₃CN). The different product fractions were collected and worked-up. The solvents were b. Preparation of Intermediate 34

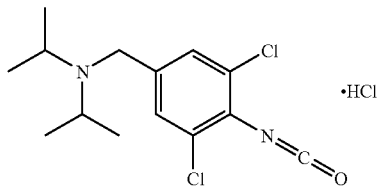 [SMILES: CC(C)N(Cc1cc(Cl)c(N=C=O)c(Cl)c1)C(C)C ; Cl]

Intermediate 33 (0.732 g, 0.00266 mol) was dissolved in a HCl solution in Et$_2$O (3.2 ml, 0.0032 mol; 1 M) and CH$_3$CN (20 ml; dry) and the mixture was stirred at room temperature for 30 minutes. Then a 20% phosgene solution in toluene (2 ml, 0.004 mol; 2 M) was added portionwise. The reaction mixture was stirred for 3 hours and then the solvent was evaporated and co-evaporated with dry toluene. The residue (crude intermediate 34 as a HCl-salt) was dissolved in CH$_2$Cl$_2$ and this solution was used immediately in the next reaction step.

Example A15 a. Preparation of Intermediate 35

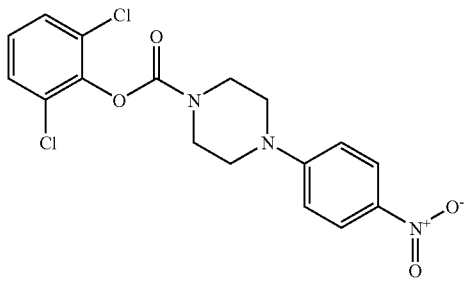 [SMILES: O=C(Oc1c(Cl)cccc1Cl)N1CCN(c2ccc([N+](=O)[O-])cc2)CC1]

NaH (0.396 g, 0.0099 mol; 60%) was added portionwise to a stirring solution of 2,6-dichlorophenol in THF (50 ml; p.a. dried on molecular sieves) under N$_2$ atmosphere. The mixture was stirred for 15 minutes and then 4-(4-nitrophenyl)-1-piperazinecarbonyl chloride (0.89 g, 0.0033 mol) was added. The reaction mixture was continued stirring for 1 hour at room temperature and was then refluxed for 18 hours. The mixture was cooled to room temperature and poured into ice-water (200 ml). This mixture was stirred for 15 minutes and then the product was filtered off, washed with H$_2$O and dried (50° C., in vacuo). Yield: 1.3 g of intermediate 35 (99%).

b. Preparation of Intermediate 36

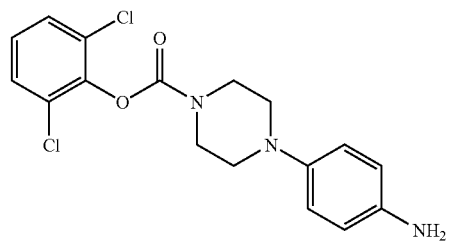 [SMILES: Nc1ccc(N2CCN(C(=O)Oc3c(Cl)cccc3Cl)CC2)cc1]

A solution of intermediate 35 (1.3 g, 0.00328 mol) in acetic acid (50 ml) and a thiophene solution (6.901 ml, 0.00328 mol; 4% in DIPE) was hydrogenated with Pt/C 5% (0.3 g) as a catalyst. After 3 eq. of H$_2$ were taken up, the catalyst was filtered off. The filtrate was evaporated and co-evaporated with toluene (2×). The residue was dissolved in CH$_2$Cl$_2$ and the solution was washed with an aqueous saturated NaHCO$_3$ solution. The layers were separated and the organic layer was dried (MgSO$_4$), filtered and the solvent was evaporated and co-evaporated with toluene. The residue was stirred in Et$_2$O, filtered off and washed with Et$_2$O (3×). The product was dried (50° C., in vacuo). Yield: 0.94 g of intermediate 36.

Example A16 a. Preparation of Intermediate 39

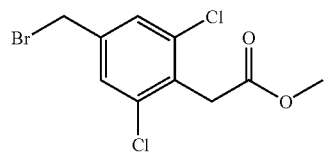

2,6-Dichloro-4-methyl-benzeneacetic acid methyl ester (10.27 g, 0.044 mol) was dissolved in 100 ml of CCl$_4$. Then, N-bromosuccinimide (0.053 mol) and 2,2'-(1,2-diazenediyl)bis[2-methylpropanenitrile] (0.0022 mol) were added to the solution. The resulting mixture was refluxed for 10 hours. The solution was cooled and passed through a silica gel layer. The silica gel was washed with CCl$_4$ (about 100 ml) and hexane (about 200 ml). The combined filtrates were concentrated in vacuo. The obtained residue became crystalline after cooling (12.85 g). After recrystallisation from hexane 10.30 g of intermediate 39 was obtained.

b. Preparation of Intermediate 40

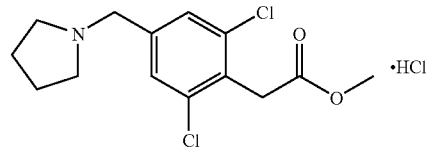 [SMILES: COC(=O)Cc1c(Cl)cc(CN2CCCC2)cc1Cl ; Cl]

Intermediate 39 (8.682 g) and pyrrolidine (6.86 ml) were mixed and heated at 90-100° C. for 5 minutes. H$_2$O (50 ml) was added, and the resulting mixture was extracted with CH$_2$Cl$_2$ (3×50 ml). The combined organic layer was separated, dried over sodium sulphate and evaporated in vacuo.

c. Preparation of Intermediate 41

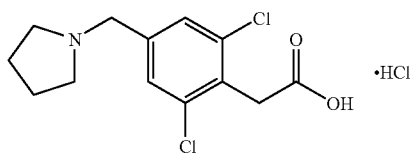 [SMILES: O=C(O)Cc1c(Cl)cc(CN2CCCC2)cc1Cl ; Cl]

Intermediate 40 (5.00 g, 14.76 mmol) and LiOH.H$_2$O (1.24 g, 29.53 mmol) were dissolved in a mixture of H$_2$O (20 ml) and MeOH (40 ml) and refluxed for 20 minutes. Then HCl$_{conc}$ (3 ml) was added and the mixture was evaporated in vacuo. Then HCl$_{conc}$ was added (5 ml) and the resulting suspension was diluted with acetone (about 20 ml). The suspension was refluxed for 5 minutes and cooled till room temperature. The formed yellowish crystalline product was filtered off, washed with acetone and dried on the air. Yield: 3.791 g of intermediate 41 (.HCl) (79%).

Example A17 a. Preparation of Intermediate 42

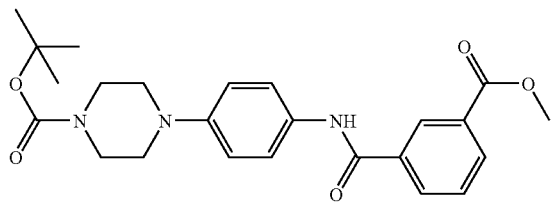 [SMILES: COC(=O)c1cccc(C(=O)Nc2ccc(N3CCN(C(=O)OC(C)(C)C)CC3)cc2)c1]

4-(4-Aminophenyl)-1-piperazinecarboxylic acid 1,1-dimethylethyl ester (1.00 g, 3.61 mmol), 1,3-benzenedicarboxylic acid 1-methyl ester (4.33 mmol), O-benzotriazolyl tetramethylisouronium tetrafluoroborate (TBTU) (5.03 mmol) and Et$_3$N (1.50 ml, 10.7 mmol) were mixed in CH$_3$CN (10 ml) and stirred at room temperature for 5 hours. The crystalline product was filtered off from the reaction mixture, washed with H$_2$O and dried on the air. Yield: 1.262 g of intermediate 42 (80%).

b. Preparation of Intermediate 43

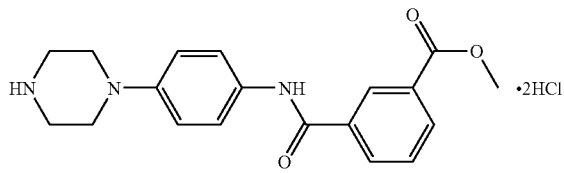 [SMILES: COC(=O)c1cccc(C(=O)Nc2ccc(N3CCNCC3)cc2)c1 ; "·2HCl"]

A 4 N HCl solution in 1,4-dioxane (5 ml, 20 mmol) was added to a mixture of intermediate 42 (1.262 g, 2.87 mmol) and 15 ml of dioxane. The resulting slurry was stirred at 45-50° C. for 30 minutes. The mixture was cooled to room temperature, and the crystalline product was filtered off, washed with acetone, hexane and dried in vacuo. Yield: 1.118 g of intermediate 43 (95%; 0.2 HCl).

B. Preparation of the Final Compounds

Example B1 a. Preparation of Compound 1

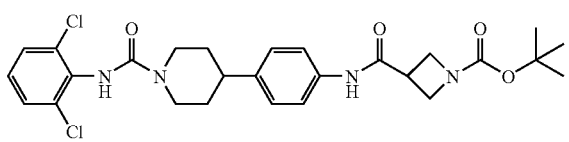 [SMILES: CC(C)(C)OC(=O)N1CC(C(=O)Nc2ccc(C3CCN(C(=O)Nc4c(Cl)cccc4Cl)CC3)cc2)C1]

1-(1,1-dimethylethyl)-1,3-azetidinedicarboxylic acid ester (0.001 mol) was dissolved in DMF (5 ml) to get stock solution (I). Part of stock solution (I) (1.2 ml, containing 0.00024 mol of 1-(1,1-dimethylethyl)-1,3-azetidinedicarboxylic acid ester) was put into the MiniBlock. PS-Carbodiimide, 1.9 mmol/g (0.0004 mol) was added with ArgoScoop. A solution of 1-hydroxy-1H-benzotriazole (0.00030 mol) in DMF (1 ml) was added and the mixture was shaken for 30 minutes. A solution of intermediate 2 (prepared according to A1.b) (0.0002 mol) in DMF (3.5 ml) was added and the reaction mixture was shaken overnight. MP-carbonate, 2.8 mmol/g (0.00090 mol) and resin-linked-NCO, 1.8 mmol/g (0.0002 mol) were added with ArgoScoop. The reaction mixture was shaken overnight, then filtered. CH$_2$Cl$_2$ (4 ml) was added and the mixture was shaken for 2 hours. The mixture was filtered and the filtrate's solvent was evaporated (Genevac® solvent evaporator). The residue (±0.120 g) was purified by HPLC. The product fractions were collected and worked-up. Yield: 0.014 g of compound 1.

b. Preparation of Compound 2

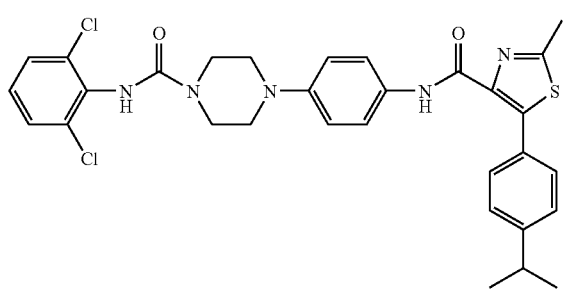 [SMILES: Cc1nc(C(=O)Nc2ccc(N3CCN(C(=O)Nc4c(Cl)cccc4Cl)CC3)cc2)c(-c2ccc(C(C)C)cc2)s1]

Intermediate 7 (prepared according to A3.b) (0.00012 mol) was dissolved in DMF (1.2 ml). PS-Carbodiimide, 2.1 mmol/g (0.0002 mol) and 1-hydroxy-1H-benzotriazole (0.00015 mol) were added. The reaction mixture was shaken for 30 minutes. A solution of intermediate 5 (prepared according to A2.b) (0.0001 mol) in DMF (2 ml) was added. The reaction mixture was shaken overnight. MP-carbonate, 6.2 mmol/g (0.00045 mol) and resin-linked-N=C=O were added. The mixture was shaken overnight at room temperature. The mixture was filtered. CH$_2$Cl$_2$ (2 ml) was added. The mixture was shaken for one hour, then filtered again. The filtrate's solvent was evaporated (Genevac® solvent evaporator). Impure residues were purified by HPLC. The product fractions were collected and worked-up. Yield: 0.0128 g of compound 2.

Compound 65 was prepared according to the above-described procedure except for reactant intermediate 7 which should be replaced by 2-methyl-5-(3-trifluoromethyl-phenyl)-thiazole-4-carboxylic acid (prepared according to A8.b).

Compound 18 was prepared according to the above-described procedure except for reactant intermediate 7 which should be replaced by intermediate 16 (prepared according to A7.b).

c. Preparation of Compound 3

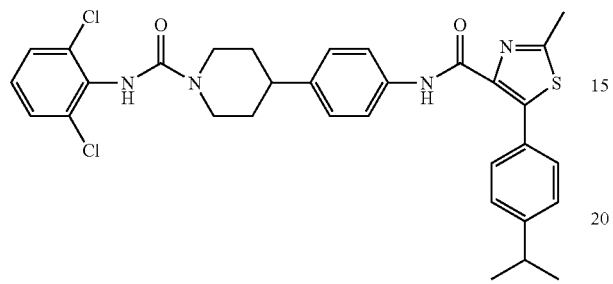

Intermediate 7 (prepared according to A3.b) (0.00012 mol) was dissolved in DMF (1.2 ml). PS-Carbodiimide, 2.1 mmol/g (0.0002 mol) and 1-hydroxy-1H-benzotriazole (0.00015 mol) were added. The reaction mixture was shaken for 30 minutes. A solution of intermediate 2 (prepared according to A1.b) (0.0001 mol) in DMF (2 ml) was added. The reaction mixture was shaken overnight. MP-carbonate, 6.2 mmol/g (0.00045 mol) and resin-linked-N=C=O (0.0001 mol) were added. The mixture was shaken overnight at room temperature. The mixture was filtered. CH$_2$Cl$_2$ (2 ml) was added. The mixture was shaken for one hour, then filtered again. The filtrate's solvent was evaporated (Genevac® solvent evaporator). The impure residue was purified by HPLC. The product fractions were collected and worked-up. Yield: 0.015 g of compound 3.

Compound 54 was prepared according to the above-described procedure except for reactant intermediate 7 which should be replaced by 2-methyl-5-(3-trifluoromethyl-phenyl)-thiazole-4-carboxylic acid (prepared according to A8.b).

Compound 55 was prepared according to the above-described procedure except for reactant intermediate 7 which should be replaced by intermediate 18 (prepared according to A8.b).

d. Preparation of Compound 4

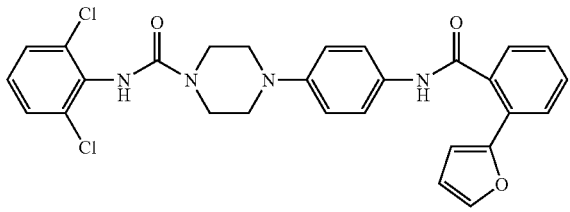 [SMILES: O=C(Nc1ccc(N2CCN(C(=O)Nc3c(Cl)cccc3Cl)CC2)cc1)c1ccccc1-c1ccco1]

A solution of PS-Carbodiimide and 1-hydroxy-1H-benzotriazole in DMF (1 ml) was added to a solution of 2-(2-furanyl)benzoic acid in DMF (1.2 ml) and then shaken for 1 hour at room temperature. Then a solution of intermediate 5 (prepared according to A2.b) in DMF (1 ml) was added to the reaction mixture. The reaction mixture was shaken overnight at room temperature. MP-carbonate (q.s.) and resin-linked N=C=O polymer (q.s.) were added to the reaction mixture and again shaken overnight. The reaction mixture was filtered to result in filtrate F1. The residue was shaken for 2 hours in CH$_2$Cl$_2$ (3 ml). This mixture was filtered to result in filtrate F2. F1 and F2 were combined and the solvents were evaporated. The residue was purified by reversed-phase high-performance liquid chromatography (Shandon Hyperprep® C18 BDS (Base Deactivated Silica) 8 μm, 250 g, I.D. 5 cm). A gradient with the mentioned mobile phases was applied (phase A: (0.5% NH$_4$OAc in H$_2$O)/CH$_3$CN 90/10); phase B: CH$_3$OH (optional); phase C: CH$_3$CN). The desired product fractions were collected and worked-up. Yield: 0.002 g of compound 4.

Example B2 a. Preparation of compound 5

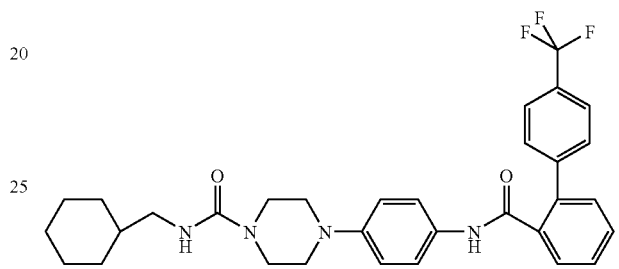

(Isocyanatomethyl)-cyclohexane (0.00011 mol) was dissolved in DMF (3 ml). Intermediate 9 (prepared according to A4.b) (0.0001 mol) was added. The reaction mixture was shaken for 2 hours at room temperature. PS-Trisamine (3.2 mmol/g) (0.0001 mol) and resin-linked-N=C=O, 1.8 mmol/g (0.0001 mol) were added. The reaction mixture was shaken overnight at room temperature. The mixture was filtered. CH$_2$Cl$_2$ (2 ml) was added. The mixture was shaken for one hour, filtered and the filtrate's solvent was evaporated. Yield: 0.051 g of compound 5.

b. Preparation of Compound 6

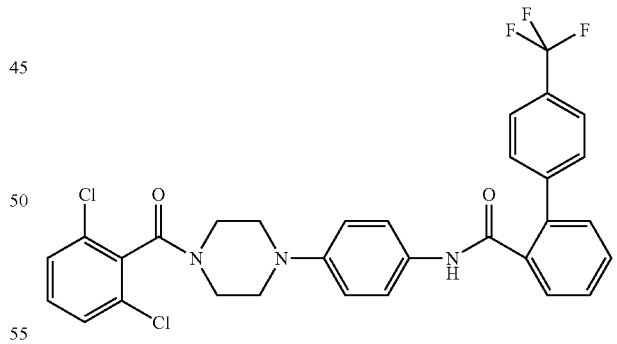

A mixture of intermediate 9 (prepared according to A4.b) (0.00023 mol) and PS-NMM (2.03 mmol/g) (0.00023 mol) in DMF (3 ml) was stirred for 15 minutes. A solution of 2,6-dichlorobenzoyl chloride (0.00035 mol) in DMF (1 ml) was added and the mixture was stirred for 2 hours. More PS-NMM (2.03 mmol/g; Argonaut) (0.05 g) was added and the mixture was stirred for 10 minutes. Extra 2,6-dichlorobenzoyl chloride was added and the reaction mixture was stirred overnight at room temperature. PS-Trisamine (4.35 mmol/g; Novabiochem) (0.0002 mol) was added and the mixture was stirred for 4 hours. The reaction mixture was filtered and the filtrate was stirred with PS-TsOH (0.1 g) overnight. The mixture was filtered and the filtrate was purified by HPLC over Purospher Star RP-18 (20 g, 5 µm; eluent: ((0.5% NH₄OAc in H₂O)/CH₃CN 90/10)/CH₃OH/CH₃CN (0 minutes) 75/25/0, (10.00 minutes) 0/50/50, (16.00 minutes) 0/0/100, (18.10-20 minutes) 75/25/0). The desired fractions were collected and the organic solvent was evaporated. The aqueous concentrate was extracted with CH₂Cl₂ and the solvent was evaporated. Yield: 0.127 g of compound 6 c. Preparation of Compound 7

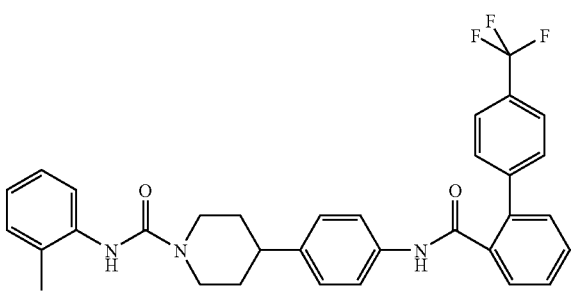 [SMILES: Cc1ccccc1NC(=O)N1CCC(c2ccc(NC(=O)c3ccccc3-c3ccc(C(F)(F)F)cc3)cc2)CC1]

1-isocyanato-2-methylbenzene (0.00011 mol) was dissolved in DMF (3 ml). Intermediate 12 (prepared according to A5.b) (0.0001 mol) was added. The reaction mixture was shaken for 2 hours at room temperature. PS-Trisamine (0.0001 mol; 3.2 mmol/g) and resin-linked-N=C=O, 1.8 mmol/g (0.0001 mol) were added. The reaction mixture was shaken overnight at room temperature. The mixture was filtered. CH₂Cl₂ (2 ml) was added. The mixture was shaken for one hour, filtered and the filtrate's solvent was evaporated. The less pure residues were purified by HPLC. The product fractions were collected and worked-up Yield: 0.0048 g of compound 7.

Example B3 a. Preparation of Compound 8

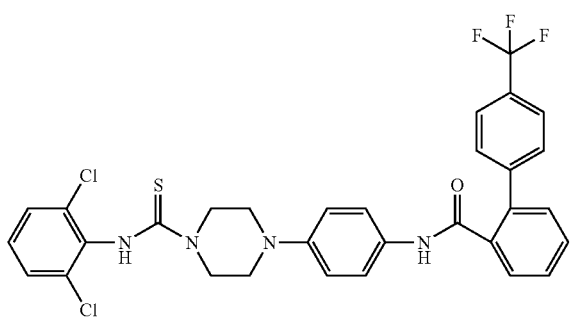 [SMILES: O=C(Nc1ccc(N2CCN(C(=O)Nc3c(Cl)cccc3Cl)CC2)cc1)c1ccccc1-c1ccc(C(F)(F)F)cc1]

A mixture of intermediate 9 (prepared according to A4.b) (0.00023 mol) and Et₃N (0.1 ml) in CH₂Cl₂ (5 ml) was stirred until complete dissolution. 1,3-Dichloro-2-isothiocyanotobenzene (0.0003 mol) was added and the mixture was shaken overnight. The mixture was washed with a saturated aqueous NH₄Cl solution (2 ml), then filtered through Extrelut and the extract's solvent was evaporated. The residue was purified by HPLC over Hyperprep RP-C18 BDS (100 g, 100 Å, 8 µm; eluent: [(0.5% NH₄OAc in H₂O)/CH₃CN 90/10)]/CH₃OH/ CH₃CN (0 min) 75/25/0, (10 min) 0/50/50, (16 min) 0/0/100, (18.10-20.00 min) 75/25/0). The pure fractions were collected and worked-up. Yield: 0.059 g of compound 8.

Melting point: 224.5° C.

b. Preparation of Compound 9

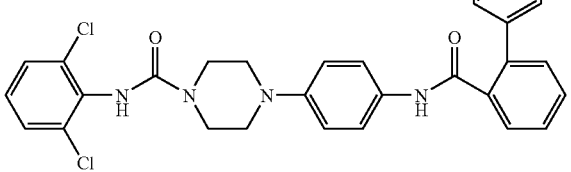

A mixture of intermediate 9 (prepared according to A4.b) (0.00023 mol) and Et₃N (0.1 ml) in CH₂Cl₂, anhydrous (5 ml) was stirred until complete dissolution. 1,3-Dichloro-2-isocyanatobenzene (0.0003 mol) was added and the reaction mixture was shaken overnight, then filtered and the precipitate was washed with CH₂Cl₂, then dried. Yield: 0.104 g of compound 9.

Melting point: 289.0° C.

Example B4

Preparation of Compound 10

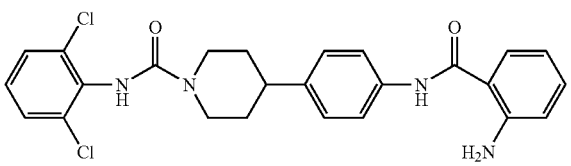

•trifluoroacetate

A mixture of intermediate 3 (prepared according to A1.c) (0.0002 mol; approximately, crude intermediate) and trifluoroacetic acid (0.2 ml) in CH₂Cl₂ (2 ml) was shaken for 4 hours at room temperature. The solvent was partially evaporated (Genevac® solvent evaporator). Toluene was added to the concentrate and the mixture was azeotroped on the rotary evaporator. Yield: 0.008 g of compound 10.

Example B5

Preparation of Compound 11

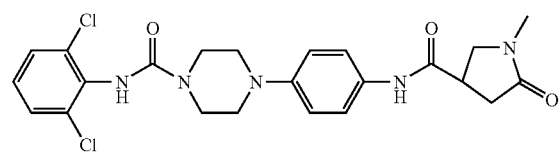 [SMILES: CN1CC(C(=O)Nc2ccc(N3CCN(C(=O)Nc4c(Cl)cccc4Cl)CC3)cc2)CC1=O]

N'-(ethylcarbonimidoyl)-N,N-dimethyl-1,3-propanediamine monohydrochloride (0.000302 mol) was added to a mixture of intermediate 5 (prepared according to A2.b) (0.000275 mol), 1-methyl-5-oxo-3-pyrrolidinecarboxylic acid (0.000275 mol), 1-hydroxy-1H-benzotriazole (0.000028 mol) and N-ethyl-N-(1-methylethyl)-2-propanamine (0.000329 mol) in THF, dried over 3 Å molecular sieves (5 ml) and then stirred for 64 hours at room temperature. The solvent was evaporated (under $N_2$). The residue was stirred in $CH_3OH$ (5 ml) and $H_2O$ (5 ml) and then heated to boiling point. The mixture was let to cool to room temperature without stirring. The precipitate was filtered off, washed with $CH_3OH$ and dried (vacuum, overnight). Yield: 0.082 g of compound 11.

Example B6

Preparation of Compound 129

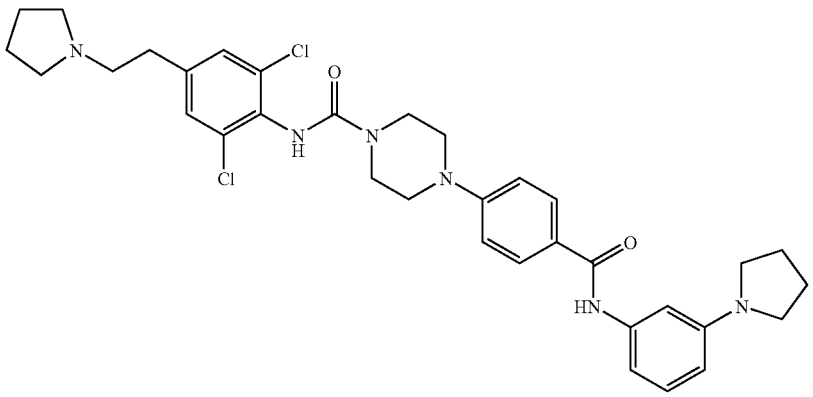 [SMILES: O=C(Nc1cccc(N2CCCC2)c1)c1ccc(N2CCN(C(=O)Nc3c(Cl)cc(CCN4CCCC4)cc3Cl)CC2)cc1]

Intermediate 20 (0.55 g, 1.569 mmol) (prepared according to A9.b) was dissolved in $Et_3N$ (1.1 ml) and $CH_2Cl_2$ (50 ml). The crude intermediate 23 (0.448 g) (prepared according to A10.c) and $CH_2Cl_2$ (100 ml) were added. The reaction mixture was stirred for 48 hours and then the mixture was stirred in a saturated solution of $NaHCO_3$ in $H_2O$. $CH_2Cl_2/MeOH$ 90/10 and $H_2O$ were added and the layers were separated. The separated organic layer was dried ($MgSO_4$), filtered and the solvent was evaporated. The residue was stirred in DIPE and was filtered off. The product was washed with EtOH and DIPE (once). The product was dried (50° C., 18 hours, in vacuo). Yield: 0.727 g of compound 129 (73%).

Example B7

Preparation of Compound 130

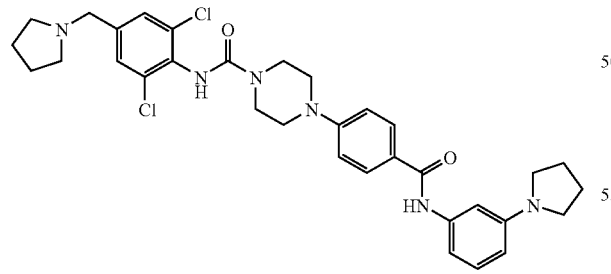

DECP (0.357 ml, 0.00239 mol) was added to a stirring solution of intermediate 28 (0.57 g, 0.00119 mol) (prepared according to A11.d-1) and 3-(1-pyrrolidinyl)-benzenamine (0.25 g, 0.00143 mol) in $Et_3N$ (0.671 ml, 0.00478 mol) and $CH_2Cl_2$ (35 ml) at room temperature. After 48 hours, more DECP (0.0893 ml) was added and the mixture was stirred at room temperature for 3 hours. More $Et_3N$ (0.336 ml) was added and the mixture was stirred for 18 hours. A saturated aqueous $NaHO_3$ solution was added and the mixture was stirred. The layers were separated and the $CH_2Cl_2$ layer was dried ($MgSO_4$), filtered and the solvent was evaporated and co-evaporated with toluene. The residue was purified by FLASH chromatography (silica; eluent: $CH_2Cl_2$/MeOH from 99/1 till 97/3). The desired fractions were collected and the solvent was evaporated. The residue (0.491 g) was purified by reversed phase high-performance liquid chromatography (Shandon Hyperprep® C18 BDS (Base Deactivated Silica) 8 μm, 250 g, I.D. 5 cm). A gradient with 3 mobile phases was applied. Phase A: 90% of a 0.5% $NH_4OAc$ solution in water+10% $CH_3CN$; phase B: $CH_3OH$; phase C: $CH_3CN$). The desired fractions were collected and the solvents were partially evaporated. A saturated aqueous $NaHCO_3$ solution was added and the organic products were extracted with $CH_2Cl_2$. The layers were separated and the $CH_2Cl_2$ layer was dried ($MgSO_4$), filtered and the solvent was evaporated and co-evaporated with toluene. The residue was stirred in DIPE and the solid was filtered off and dried (50° C., 72 hours, in vacuo). Yield: 0.184 g of compound 130.

Example B8

Preparation of Compound 131

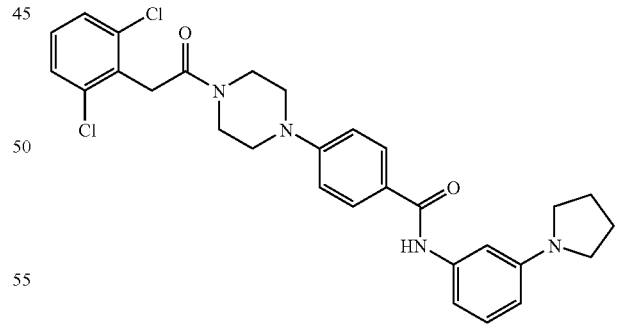

2,6-Dichloro-benzeneacetic acid (0.102 g, 0.499 mmol) and DIPEA (0.6 ml) were added to a solution of intermediate 20 (0.175 g, 0.499 mmol) in $CH_3CN$ (5 ml; dry) and DMF (2 ml; dry). DEPC (1.2 eq) was added and the reaction mixture was stirred at room temperature for 1 hour. The solvent was evaporated and the residue was purified by flash silica chromatography. The desired fractions were collected and the solvent was evaporated to yield 0.155 g of compound 131 (58%).

Example B9

Preparation of Compound 136

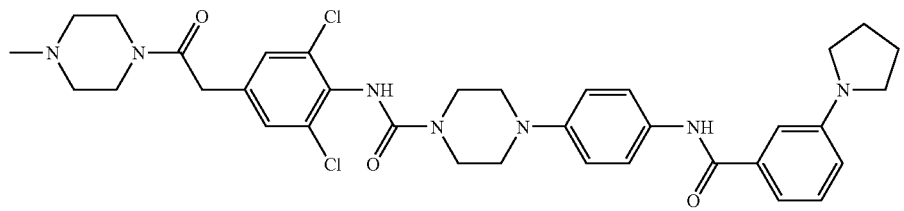 [SMILES: CN1CCN(C(=O)Cc2cc(Cl)c(NC(=O)N3CCN(c4ccc(NC(=O)c5cccc(N6CCCC6)c5)cc4)CC3)c(Cl)c2)CC1]

Intermediate 32 (0.5 g, 0.00152 mol) (prepared according to A13.b) in CH$_2$Cl$_2$ (10 ml) was stirred. This mixture was added to a stirring solution of intermediate 30 (0.54 g, 0.00153 mol) (prepared according to A12.b) in Et$_3$N (1 ml, 0.00712 mol) and CH$_2$Cl$_2$ (20 ml). After 2 hours, CH$_2$Cl$_2$ (50 ml) and a half saturated NaHCO$_3$ solution (q.s.) were added and the mixture was stirred. Subsequently, MeOH (10 ml) and CH$_2$Cl$_2$ (10 ml) were added and the mixture was stirred for 18 hours. Then the mixture was left without stirring for 48 hours, but the layers were not separated properly. Therefore, the mixture was filtered over diatomaceous earth (Dicalite®). The layers were separated and the organic layer was dried (MgSO$_4$), filtered and the solvent was evaporated and co-evaporated with toluene, yielding 1.006 g. The crude compound was purified by reversed-phase high-performance liquid chromatography (Shandon Hyperprep® C18 BDS (Base Deactivated Silica) 8 μm, 250 g, I.D. 5 cm). A gradient with 3 mobile phases was applied. Phase A: a 0.25% NH$_4$HCO$_3$ solution in water; phase B: CH$_3$OH; phase C: CH$_3$CN). The desired fractions were collected and the solvent was evaporated until only the water layer was obtained. This water layer was neutralized with NaHCO$_3$ and was extracted with CH$_2$Cl$_2$. The separated organic layer was dried (MgSO$_4$), filtered and the solvent was evaporated and co-evaporated with toluene. The residue was stirred in Et$_2$O and the solid was filtered off, yielding 0.032 g of compound 136.

Example B10

Preparation of Compound 137

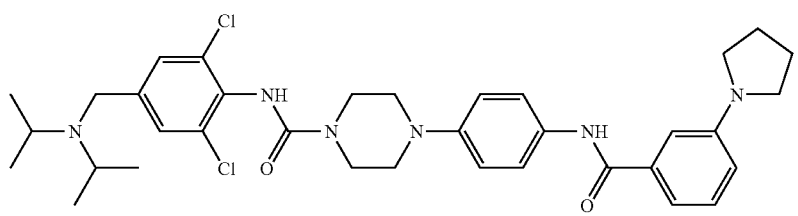 [SMILES: CC(C)N(Cc1cc(Cl)c(NC(=O)N2CCN(c3ccc(NC(=O)c4cccc(N5CCCC5)c4)cc3)CC2)c(Cl)c1)C(C)C]

Intermediate 30 (0.465 g, 0.00133 mol) (prepared according to A12.b) was dissolved in CH$_2$Cl$_2$ (10 ml) and Et$_3$N (1 ml, 0.00712 mol) resulting in a brown turbid mixture. Intermediate 34 (0.4 g, 0.00133 mol) (prepared according to A14.b) was dissolved in CH$_2$Cl$_2$ (10 ml) and this solution was added to the brown turbid mixture. The reaction mixture was stirred for 1 hour and was then filtered off and washed (2× with CH$_2$Cl$_2$, 1× with CH$_3$CN and again 1× with CH$_2$Cl$_2$). The solid was dried (50° C., 18 hours, in vacuo). Yield: 0.505 g of compound 137 (56%).

Example B11

Preparation of Compound 139

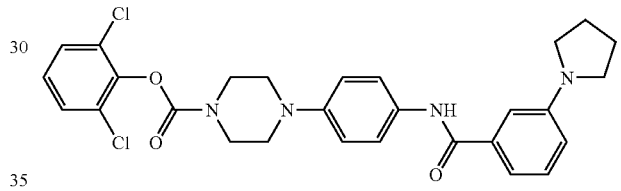

DECP (0.253 ml, 0.00169 mol) was added to a stirring solution of intermediate 36 (0.564 g, 0.00154 mol) (prepared according to A15.b) and 3-(1-pyrrolidinyl)benzoic acid (0.309 g, 0.00162 mol) in CH$_2$Cl$_2$ (20 ml; p.a.) and Et$_3$N (0.433 ml, 0.00308 mol). The reaction mixture was stirred for 18 hours under N$_2$ atmosphere. Then an aqueous saturated NaHCO$_3$ solution (15 ml) was added and the mixture was stirred for 2 hours. CH$_2$Cl$_2$/MeOH 90/10 (10 ml) was added and the mixture was stirred for 1 hour. The layers were separated and the organic layer was washed (H$_2$O), dried (MgSO$_4$), filtered and the solvent was evaporated. The residue was stirred in Et$_2$O/EtOAc (10 ml/10 ml), filtered off, washed (EtOAc/Et$_2$O first 1/1, then 0/1) and dried (50° C., in vacuo). Yield: 0.655 g of compound 139 (79%).

Example B12

Preparation of Compound 140

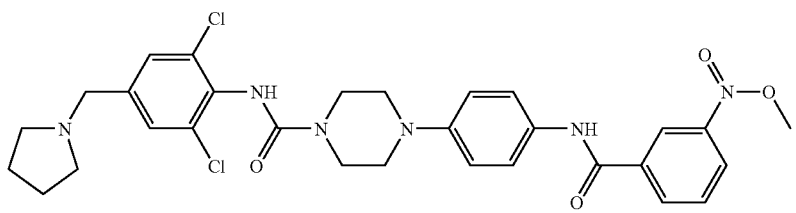

DECP (1.167 ml, 0.00703 mol) was added to a stirring solution of intermediate 38 (2.1 g, 0.00468 mol) (prepared according to A11.d-2) and 1,3-benzenedicarboxylic acid 1-methyl ester (0.886 g, 0.00492 mol) in $Et_3N$ (1.316 ml, 0.00937 mol) and $CH_2Cl_2$ (100 ml; p.a.). The reaction mixture was stirred for 18 hours at room temperature and then an aqueous saturated $NaHCO_3$ solution (50 ml) and $CH_2Cl_2$/MeOH 1/1 (40 ml) was added. The mixture was stirred for 15 minutes. The layers were separated and the organic layer was stirred with $H_2O$ (50 ml) and left standing overnight in a separated funnel. The precipitate in the organic layer was filtered off, washed ($CH_2Cl_2$) and dried (50° C., in vacuo), yielding 0.54 g of compound 140 (19%). The filtrate was evaporated and the residue was stirred in acetone, filtered off, washed (acetone) and dried (50° C., in vacuo), yielding 1 g of compound 140 (35%).

Example B13

Preparation of Compound 145

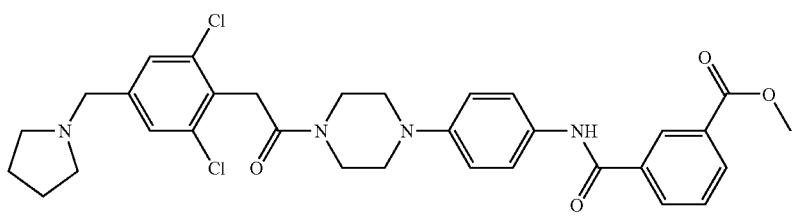 [SMILES: COC(=O)c1cccc(C(=O)Nc2ccc(N3CCN(C(=O)Cc4c(Cl)cc(CN5CCCC5)cc4Cl)CC3)cc2)c1]

TBTU (4.20 mmol) and $Et_3N$ (2.08 ml, 15.0 mmol) were added to a suspension of intermediate 41 (3.60 mmol) (prepared according to A16.c) in $CH_3CN$ (10 ml). The mixture was stirred for 10 minutes at room temperature. Then, intermediate 43 (2.71 mmol) (prepared according to A17.b) was added to the reaction mixture. The mixture was stirred for 5 hours at room temperature. The crystalline product was filtered off, washed with small amount of acetone and dried on the air. Yield: 1.406 g of compound 145 (85%).

Tables 1 to 7 list the compounds that were prepared by analogy to one of the above Examples.

TABLE 1
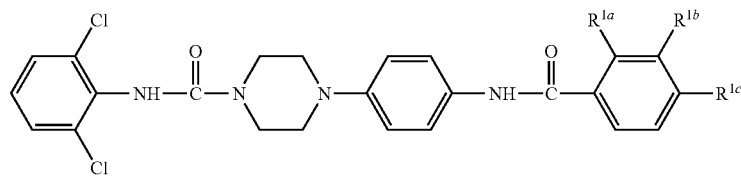
| Comp. no. | Ex. no. | R1a | R1b | R1c |
|---|---|---|---|---|
| 125 | B2 | H | ethyl ester (–C(CH₃)–C(=O)–O–CH₂CH₃) | H |
| 12 | B1.d | H | –C(CH₃)–pyrrolidin-1-yl | H |
| 13 | B1.d | H | –C(CH₃)–(2-oxopyrrolidin-1-yl) | H |
| 4 | B1.d | 2-furyl-CH(CH₃)– | H | H |
| 14 | B1.d | H | 2-furyl-CH(CH₃)– | H |
| 15 | B1.d | H | H | oxazol-5-yl-CH(CH₃)– |
| 16 | B1.d | H | oxazol-5-yl-CH(CH₃)– | H |
| 17 | B1.d | H | 2-methylthiazol-4-yl-CH(CH₃)– | H |
| 18 | B1.b | 2-ethyl-4-methylthiazol-5-yl-CH(CH₃)– | H | H |
| 19 | B1.d | H | H | 2,5-dimethylpyrrol-1-yl-CH(CH₃)– |

TABLE 1-continued
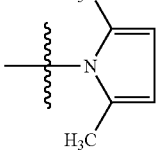
| Comp. no. | Ex. no. | R^{1a} | R^{1b} | R^{1c} |
|---|---|---|---|---|
| 20 | B1.d | H | 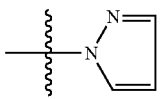 2,5-dimethyl-pyrrol-1-yl | H |
| 21 | B1.d | H | H | 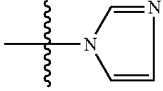 1,2,3-triazol-1-yl |
| 22 | B1.d | 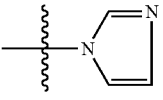 [SMILES: *n1ccnc1] imidazol-1-yl | H | H |
| 23 | B1.d | H | 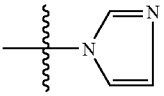 imidazol-1-yl | H |
| 24 | B1.d | H | H | 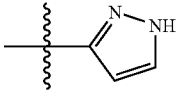 pyrazol-1-yl |
| 25 | B1.d | H | H | 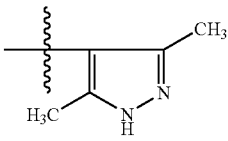 [SMILES: *c1c(C)n[nH]c1C] 1H-pyrazol-3-yl |
| 26 | B1.d | 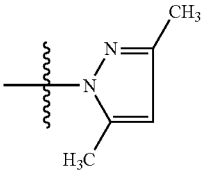 [SMILES: *n1nc(C)cc1C] 3,5-dimethyl-1H-pyrazol-4-yl | H | H |
| 27 | B1.d | H | H | 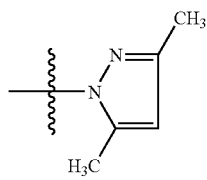 3,5-dimethyl-pyrazol-1-yl |
| 28 | B1.d | H | 3,5-dimethyl-pyrazol-1-yl | H |
| 29 | B1.d | H | H | 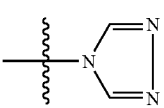 1,2,4-triazol-1-yl |

TABLE 1-continued

[Structure: 2,6-dichlorophenyl-NH-C(O)-N(piperazine)N-phenyl-NH-C(O)-phenyl(R1a, R1b, R1c)]

| Comp. no. | Ex. no. | R1a | R1b | R1c |
|---|---|---|---|---|
| 30 | B1.d | H | H | 5-methyl-1,2,4-oxadiazol-3-yl |
| 31 | B1.d | H | 5-methyl-tetrazol-1-yl | H |
| 32 | B1.d | 1H-tetrazol-5-yl | H | H |
| 33 | B1.d | H | H | 1H-tetrazol-5-yl |
| 34 | B1.b | phenyl | H | H |
| 35 | B1.b | 4-tert-butylphenyl | H | H |
| 36 | B1.b | H | 2-methylphenyl | H |
| 127 | B2 | H | 4-(isopropoxycarbonyl)phenyl | H |
| 37 | B1.d | H | piperidin-1-yl | H |
| 38 | B1.d | H | H | morpholin-4-yl |
| 39 | B1.d | morpholin-4-yl | H | H |

TABLE 1-continued
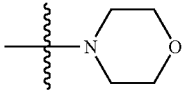
| Comp. no. | Ex. no. | R<sup>1a</sup> | R<sup>1b</sup> | R<sup>1c</sup> |
|---|---|---|---|---|
| 40 | B1.d | H | 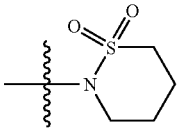 | H |
| 41 | B1.d | H | 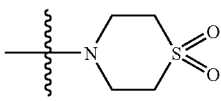 | H |
| 42 | B1.d | 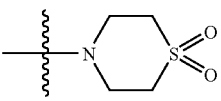 | H | H |
| 43 | B1.d | H |  | H |
| 44 | B1.d | H | H | 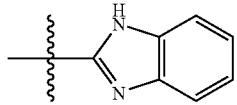 |
| 45 | B1.d | 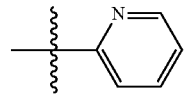 | H | H |
| 126 | B2 | H | H | 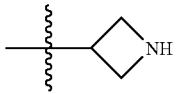 [SMILES: *C1CNC1] |
TABLE 2
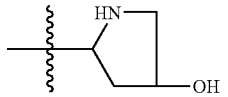 [SMILES: *C1CC(O)CN1]
| Comp. no. | Ex. no. | A | R$^1$ | Salt |
|---|---|---|---|---|
| 46 | B4 | CH | azetidine (NH) | trifluoroacetate |
| 47 | B4 | CH | pyrrolidine with OH, HN | trifluoroacetate |

TABLE 2-continued

[Structure: 2,6-dichlorophenyl-NH-C(=O)-N(piperazine with A)-phenyl-NH-C(=O)-R¹]

| Comp. no. | Ex. no. | A | R¹ | Salt |
|---|---|---|---|---|
| 48 | B4 | CH | (thiazolidin-4-yl, HN-CH₂-S ring) | trifluoroacetate |
| 10 | B4 | CH | 2-aminophenyl (H₂N on phenyl) | trifluoroacetate |
| 49 | B4 | CH | piperidin-3-yl (NH) | trifluoroacetate |
| 1 | B1.a | CH | azetidin-3-yl N-C(=O)-O-C(CH₃)₃ | |
| 50 | B1.a | CH | (CH₃)₃C-O-C(=O)-N-thiazolidin-4-yl | |
| 51 | B1.a | CH | (CH₃)₃C-O-C(=O)-N-pyrrolidin-2-yl | |
| 52 | B1.a | CH | piperidin-3-yl N-C(=O)-O-C(CH₃)₃ | |
| 3 | B1.c | CH | 4-methyl-5-(4-isopropylphenyl)-2-methylthiazol-4-yl | |
| 53 | B1.c | CH | 4-methyl-5-(3-trifluoromethylphenyl)-2-methylthiazol-4-yl | |

TABLE 2-continued

| Comp. no. | Ex. no. | A | R¹ | Salt |
|---|---|---|---|---|
| 54 | B1.c | CH | 4-(2-methylthiazol-5-yl)benzo[1,3]dioxole | |
| 55 | B1.c | CH | 2-(2-ethyl-4-methylthiazol-5-yl)phenyl | |
| 56 | B1.c | CH | biphenyl-2-yl | |
| 57 | B1.c | CH | 4'-chlorobiphenyl-2-yl | |
| 58 | B1.c | CH | 3-methyl-4'-(trifluoromethyl)biphenyl-2-yl | |
| 59 | B1.c | CH | 2'-methyl-4-(trifluoromethyl)biphenyl-3-yl | |
| 60 | B1.c | CH | 2'-methylbiphenyl-3-yl | |
| 61 | B1.c | CH | 4'-isopropylbiphenyl-3-yl | |

TABLE 2-continued
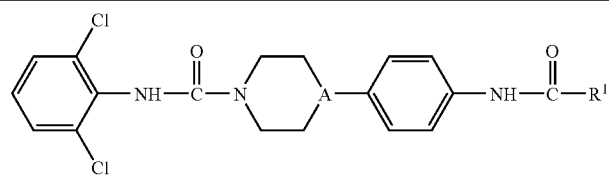
| Comp. no. | Ex. no. | A | R¹ | Salt |
|---|---|---|---|---|
| 62 | B1.c | CH |  | |
| 63 | B1.c | CH | 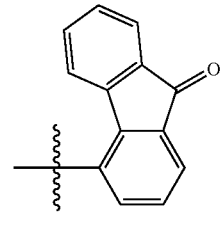 [SMILES: *c1cccc2c1-c1ccccc1C2=O] | |
| 64 | B1.c | CH | 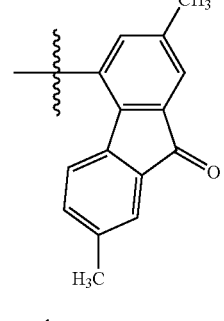 | |
| 11 | B5 | N | 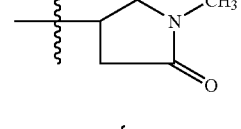 | |
| 2 | B1.b | N | 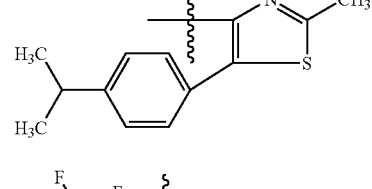 | |
| 65 | B1.b | N | 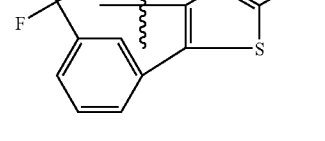 | |
| 66 | B1.b | N | 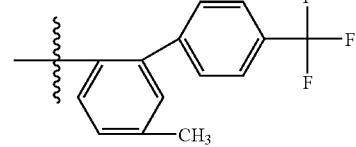 | |

TABLE 2-continued
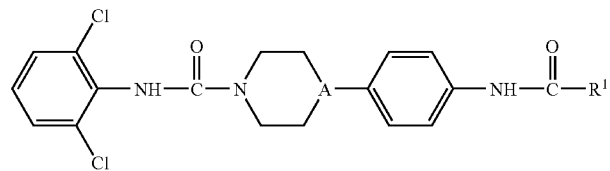
| Comp. no. | Ex. no. | A | R¹ | Salt |
|---|---|---|---|---|
| 67 | B1.b | N | 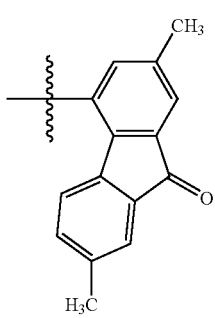 [SMILES: *c1cc(C)cc2c1-c1ccc(C)cc1C2=O] | |
TABLE 3
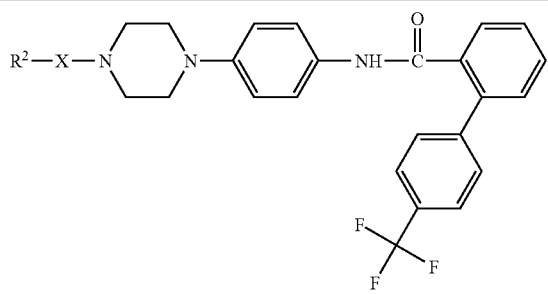
| Comp. no. | Ex. no. | X | R² |
|---|---|---|---|
| 6 | B2.b | —C=O | 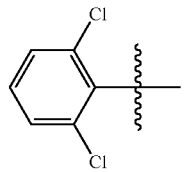 [SMILES: *c1c(Cl)cccc1Cl] |
| 68 | B3.a | —NH—C=S | 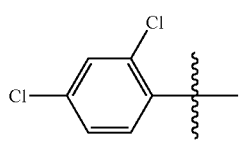 [SMILES: *c1ccc(Cl)cc1Cl] |
| 8 | B3.a | —NH—C=S | 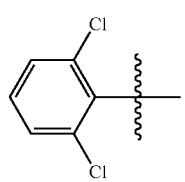 [SMILES: *c1c(Cl)cccc1Cl] |
| 69 | B3.b | —NH—C=O | (CH₃)₃—C— |

TABLE 3-continued
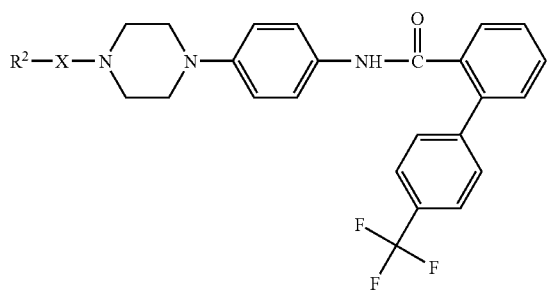
| Comp. no. | Ex. no. | X | R² |
|---|---|---|---|
| 5 | B2.a | —NH—C=O | cyclohexyl-CH₂— |
| 70 | B3.b | —NH—C=O | phenyl-CH₂— |
| 71 | B2.a | —NH—C=O | phenyl-(CH₂)₃— |
| 72 | B3.b | —NH—C=O | H₃C—CH₂—O—C(=O)—C₆H₄— |
| 73 | B2.a | —NH—C=O | (H₃C)₂N—C₆H₄— |
| 74 | B2.a | —NH—C=O | 2-(CH₃)-C₆H₄— |
| 75 | B2.a | —NH—C=O | 2-(CH₂—CH₃)-C₆H₄— |
| 76 | B2.a | —NH—C=O | 2-((CH₂)₂—CH₃)-C₆H₄— |
| 77 | B2.a | —NH—C=O | 2-(CH(CH₃)₂)-C₆H₄— |

TABLE 3-continued
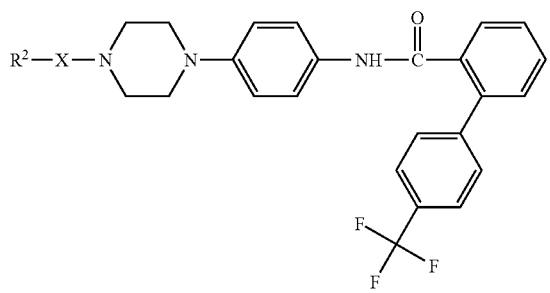
| Comp. no. | Ex. no. | X | R² |
|---|---|---|---|
| 78 | B2.a | —NH—C═O | 2-C(CH₃)₃-phenyl |
| 79 | B2.a | —NH—C═O | 2-(sec-butyl)-phenyl (H₃C—CH—CH₂—CH₃) |
| 80 | B2.a | —NH—C═O | 2-OCH₃-phenyl |
| 81 | B2.a | —NH—C═O | 2-OCH₂CH₃-phenyl |
| 82 | B2.a | —NH—C═O | 2,6-di-CH₃-phenyl |
| 83 | B2.a | —NH—C═O | 2-CH₂CH₃, 6-CH₃-phenyl |
| 84 | B2.a | —NH—C═O | 2,6-di-OCH₃-phenyl |

TABLE 3-continued
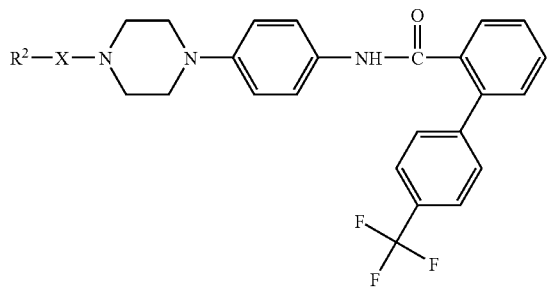
| Comp. no. | Ex. no. | X | R² |
|---|---|---|---|
| 85 | B2.a | —NH—C=O | 2,4,6-trimethylphenyl |
| 86 | B2.a | —NH—C=O | 2-(C(O)—O—CH₃)phenyl |
| 87 | B2.a | —NH—C=O | 2-(C(O)—O—CH₂—CH₃)phenyl |
| 88 | B2.a | —NH—C=O | 2-Br-phenyl |
| 89 | B2.a | —NH—C=O | 2-Cl-phenyl |
| 90 | B2.a | —NH—C=O | 2-F-phenyl |
| 91 | B2.a | —NH—C=O | 2-I-phenyl |
| 92 | B2.a | —NH—C=O | 2-NO₂-phenyl |

TABLE 3-continued
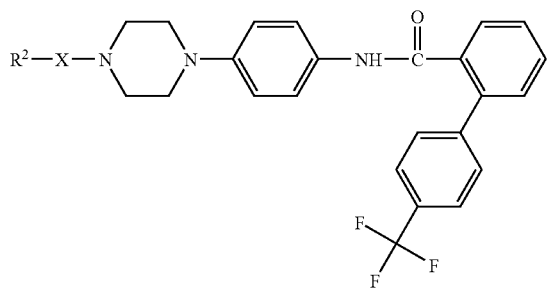
| Comp. no. | Ex. no. | X | R² |
|---|---|---|---|
| 93 | B2.a | —NH—C=O | 2-(methylthio)phenyl |
| 94 | B2.a | —NH—C=O | 2-chloro-6-methylphenyl |
| 9 | B3.b | —NH—C=O | 2,6-dichlorophenyl |
| 95 | B2.a | —NH—C=O | 2-nitro-6-methylphenyl |
| 96 | B2.a | —NH—C=O | 2-bromo-4,6-difluorophenyl |
| 97 | B2.a | —NH—C=O | 2,4,6-tribromophenyl |
| 98 | B2.a | —NH—C=O | 4-bromo-2,6-difluorophenyl |

TABLE 3-continued

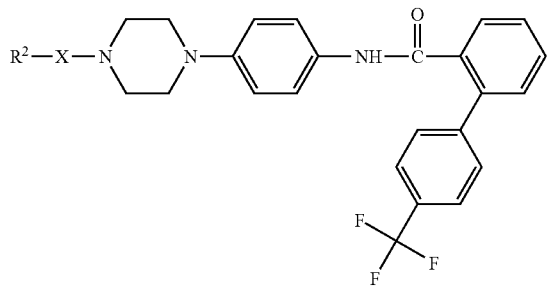

| Comp. no. | Ex. no. | X | R² |
|---|---|---|---|
| 99 | B2.a | —NH—C=O | 2,4,6-trichlorophenyl (isopropylidene) |
| 100 | B2.a | —NH—C=O | 4-bromo-2,6-dimethylphenyl (isopropylidene) |
| 101 | B2.a | —NH—C=O | 2,3-dimethyl-6-nitrophenyl (isopropylidene) |
| 102 | B2.a | —NH—C=O | 2-chloro-4,6-dimethylphenyl (isopropylidene) |
| 103 | B2.a | —NH—C=O | 2-bromo-4,6-dimethylphenyl (isopropylidene) |
| 104 | B2.a | —NH—C=O | 3-bromo-2,4,6-trimethylphenyl (isopropylidene) |
| 105 | B2.a | —NH—C=O | dibenzofuran-like (diphenyl ether bridged) |

TABLE 3-continued
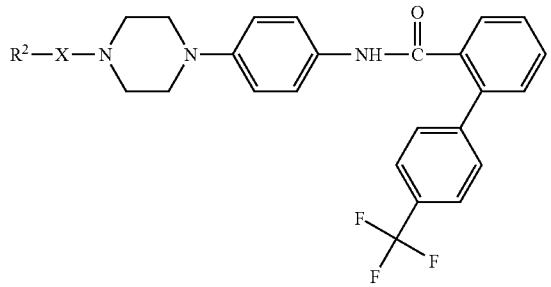
| Comp. no. | Ex. no. | X | R² |
|---|---|---|---|
| 106 | B2.a | —NH—C=O | (2,3-dihydro-1,4-benzodioxin-6-yl) |
TABLE 4
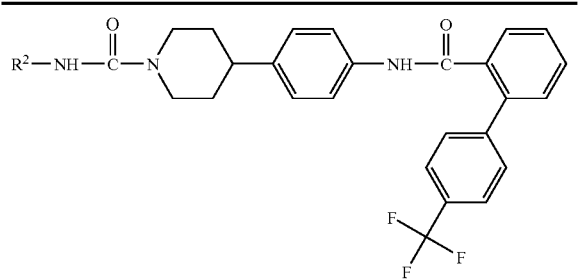
| Comp. no. | Ex. no. | R² |
|---|---|---|
| 107 | B2.a | CH₂=CH—CH₂— |
| 7 | B2.c | 2-methylphenyl |
| 108 | B2.c | 2-ethylphenyl (CH₂—CH₃) |
| 109 | B2.c | 2-isopropylphenyl CH(CH₃)₂ |
| 110 | B2.c | 2-ethyl-6-methylphenyl |
TABLE 4-continued
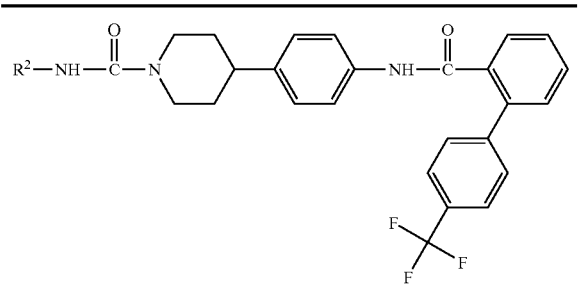
| Comp. no. | Ex. no. | R² |
|---|---|---|
| 111 | B2.c | 2,6-dimethoxyphenyl |
| 128 | B2 | 2,6-dimethylphenyl |
| 112 | B2.c | 2,4,6-trimethylphenyl |

TABLE 4-continued
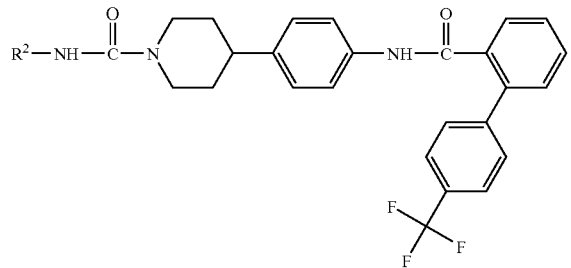
| Comp. no. | Ex. no. | R² |
|---|---|---|
| 113 | B2.c | 2-Cl, 6-CH₃-phenyl |
| 114 | B2.c | 2-Br, 3,5-F-phenyl |
| 115 | B2.c | 4-Br, 2,6-(CH₃)₂-phenyl |
| 116 | B2.c | 2-NO₂, 5,6-(CH₃)₂-phenyl |
| 117 | B2.c | 3-Cl, 2,5-(CH₃)₂, 6-CH₃-phenyl (2,4-(CH₃)₂, 3-Cl, 6-subst) |
| 118 | B2.c | 3-Br, 2,4-(CH₃)₂, 6-CH₃-phenyl |
TABLE 5
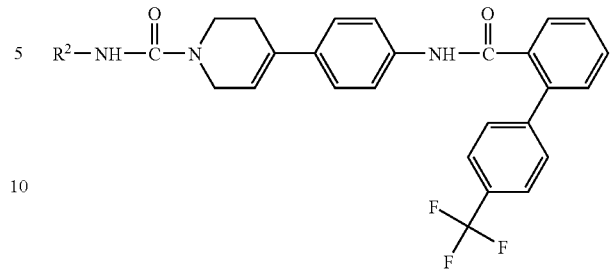
| Comp. no. | Ex. no. | R² |
|---|---|---|
| 119 | B2.c | CH₃—CH₂—CH₂— |
| 120 | B2.c | cyclohexyl-CH₂— |
| 121 | B2.c | phenyl-CH₂— |
| 122 | B2.c | phenyl-(CH₂)₃— |
| 123 | B2.c | 4-(H₃C—O)-phenyl-CH₂— |
| 124 | B2.c | 4-(N(CH₃)₂)-phenyl— |

TABLE 6

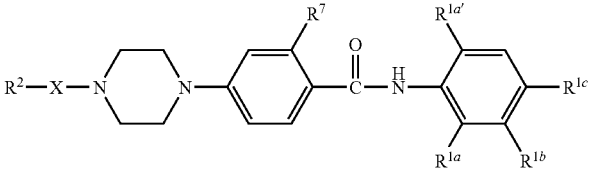

| Comp. no. | Ex. no. | X | R² | R¹ᵃ | R¹ᵃ' | R¹ᵇ | R¹ᶜ | R⁷ |
|---|---|---|---|---|---|---|---|---|
| 131 | B8 | —CH₂—C=O | 2,6-dichlorophenyl (CH(CH₃)-) | H | H | pyrrolidin-1-yl | H | H |
| 134 | B8 | —CH₂—C=O | 2,6-dichlorophenyl (CH(CH₃)-) | Cl | Cl | H | H | H |
| 135 | B8 | —CH₂—NH—C=O | 4-methoxyphenyl (CH(CH₃)-) | Cl | Cl | H | H | H |
| 133 | B7 | —NH—C=O | 3,5-dichloro-4-(pyrrolidin-1-ylmethyl)phenyl (CH(CH₃)-) | H | H | H | —OCH₃ | F |
| 130 | B7 | —NH—C=O | 3,5-dichloro-4-(pyrrolidin-1-ylmethyl)phenyl (CH(CH₃)-) | H | H | pyrrolidin-1-yl | H | H |
| 129 | B6 | —NH—C=O | 3,5-dichloro-4-(2-(pyrrolidin-1-yl)ethyl)phenyl (CH(CH₃)-) | H | H | pyrrolidin-1-yl | H | H |
| 132 | B8 | —CH₂—C=O | 2,4-dichloro-6-methylpyridin-3-yl (CH(CH₃)-) | H | H | pyrrolidin-1-yl | H | H |

TABLE 7

| Comp. no. | Ex. no. | X | R² | R¹ᵃ |
|---|---|---|---|---|
| 144 | B2 | —NH—C=O | cyclohexyl | 4-(trifluoromethyl)phenyl |
| 142 | commercial source | —CH₂—C=O | 2-methylphenyl | H |
| 141 | commercial source | —CH₂—C=O | 2-methylphenyl | H |
| 139 | B11 | —O—C=O | 2,6-dichlorophenyl | H |
| 137 | B10 | —NH—C=O | 3,5-dichloro-4-[(diisopropylamino)methyl]phenyl | H |
| 146 | B13 | —CH₂—C=O | 3,5-dichloro-4-(pyrrolidin-1-ylmethyl)phenyl | H |
| 145 | B13 | —CH₂—C=O | 3,5-dichloro-4-(pyrrolidin-1-ylmethyl)phenyl | H |
| 140 | B12 | —NH—C=O | 3,5-dichloro-4-(pyrrolidin-1-ylmethyl)phenyl | H |

TABLE 7-continued
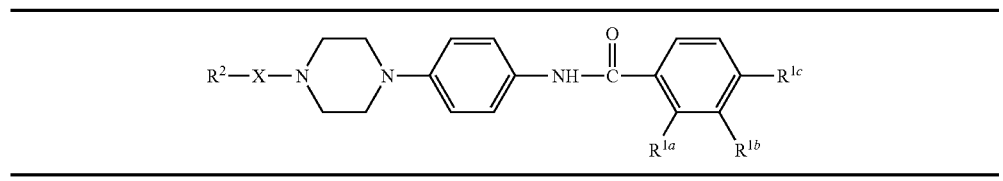
| | | | | |
|---|---|---|---|---|
| 143 | B12 | —NH—C=O | 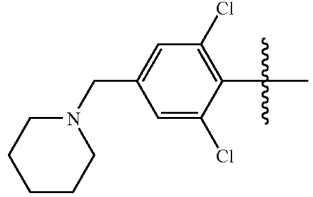 | H |
| 138 | B12 | —NH—C=O | 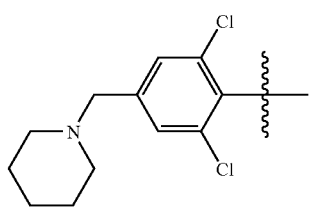 [SMILES: *c1c(Cl)cc(CN2CCCCC2)cc1Cl] | H |
| 136 | B9 | —NH—C=O | 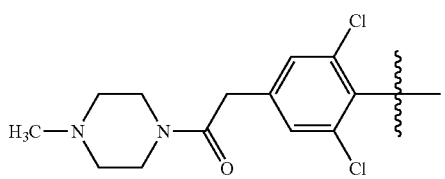 [SMILES: *c1c(Cl)cc(CC(=O)N2CCN(C)CC2)cc1Cl] | H |
| Comp. no. | Ex. no. | $R^{1b}$ | $R^{1c}$ |
|---|---|---|---|
| 144 | B2 | H | H |
| 142 | B2 commercial source | Br | H |
| 141 | B2 commercial source | H | —(CH$_2$)$_3$CH$_3$ |
| 139 | B11 | 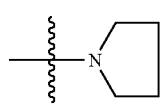 | H |
| 137 | B10 | 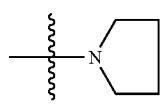 | H |
| 146 | B13 | 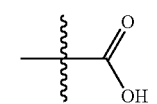 | H |
| 145 | B13 | 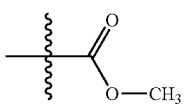 [SMILES: *C(=O)OC] | H |

TABLE 7-continued

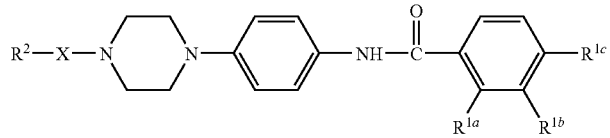

| | | | R² | |
|---|---|---|---|---|
| 140 | B12 | 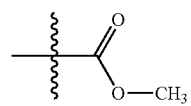 | | H |
| 143 | B12 | 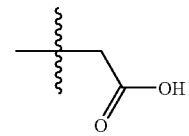 [SMILES: *CC(=O)O] | | H |
| 138 | B12 | 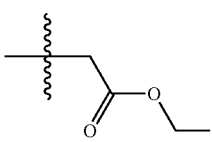 | | H |
| 136 | B9 | 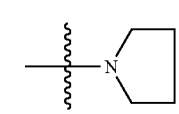 | | H |

C. Analytical Part (LC)MS

For (LC)MS-characterization of the compounds of the present invention, the following methods were used.

General Procedure A

The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

General Procedure B

The LC measurement was performed using an Acquity HPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

General Procedure C

The LCMS analyses for the compounds were done at the Surveyor MSQ™ (Thermo Finnigan, USA) comprising a photo diode array detector (PDA; 190-800 nm) and a column as specified in the respective methods below. Flow from the column was split to a MS spectrometer. The MS detector was configured with APCI (atmospheric pressure chemical ionization, + or − ions). Mass spectra were acquired by scanning from 45 to 1000 (of atomic mass unit) in 0.3 seconds. Typical APCI conditions use a corona discharge current of 10 µA and a cone voltage of 30 V. The APCI probe temperature was 640° C. Nitrogen was used as the nebulizer gas. Data acquisition was performed with an Xcalibur™ data system.

Method 1

In addition to general procedure B: Reversed phase UPLC (Ultra Performance Liquid Chromatography) was carried out on a bridged ethylsiloxane/silica hybrid (BEH) C18 column (1.7 µm, 2.1×50 mm; Waters Acquity) with a flow rate of 0.8 ml/min. Two mobile phases (mobile phase A: 0.1% formic acid in $H_2O$/methanol 95/5; mobile phase B: methanol) were used to run a gradient condition from 95% A and 5% B to 5% A and 95% B in 1.3 minutes and hold for 0.2 minutes. An injection volume of 0.5 µl was used. Cone voltage was 10 V for positive ionization mode and 20 V for negative ionization mode.

Method 2

In addition to general procedure A: Reversed phase HPLC was carried out on an Xterra MS C18 column (3.5 µm, 4.6× 100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 µl was used. Cone voltage was 10 V for positive ionization mode and 20 V for negative ionization mode.

Method 3 (Only MS)

For a number of compounds only the mass spectra were recorded (no R(t)). The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system. Cone voltage was 10 V for positive ionization mode and 20 V for negative ionization mode.

Method 4

In addition to general procedure A: Column heater was set at 45° C. Reversed phase HPLC was carried out on an Xterra MS C18 column (3.5 µm, 4.6×100 mm) with a flow rate of 1.6 ml/min. Three mobile phases (mobile phase A: 0.1% formic acid in H$_2$O/methanol 95/5; mobile phase B: acetonitrile; mobile phase C: methanol) were employed to run a gradient condition from 100% A to 1% A, 49% B and 50% C in 7 minutes and hold these conditions for 1 minute. An injection volume of 10 µA was used. Cone voltage was 10 V for positive ionization mode.

Method 5

In addition to general procedure A: Column heater was set at 45° C. Reversed phase HPLC was carried out on an Atlantis C18 column (3.5 µm, 4.6×100 mm) with a flow rate of 1.6 ml/min. Two mobile phases (mobile phase A: 70% methanol+30% H$_2$O; mobile phase B: 0.1% formic acid in H$_2$O/methanol 95/5) were employed to run a gradient condition from 100% B to 5% B+95% A in 9 minutes and hold these conditions for 3 minutes. An injection volume of 10 µl was used. Cone voltage was 10 V for positive ionization mode and 20 V for negative ionization mode.

Method 6

In addition to general procedure A: Column heater was set at 60° C. Reversed phase HPLC was carried out on an Xterra MS C18 column (3.5 µm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 0.5 minute and hold these conditions for 1 minute and reequilibrate with 100% A for 1.5 minutes. An injection volume of 10 µl was used. Cone voltage was 10 V for positive ionization mode and 20 V for negative ionization mode.

Method 7

In addition to general procedure C: Reversed phase HPLC was carried out on a Waters XTerra MS C18 column (3.5 2.1×30 mm) with a flow rate of 1.0 ml/min. Two mobile phases (mobile phase A: 0.1% aqueous solution of formic acid; mobile phase B: acetonitrile) were used. First, 100% A was hold for 0.1 minutes. Then a gradient was applied to 5% A and 95% B in 3 minutes and hold for 0.8 minutes. The injection volume was 1 µl. The column was at room temperature.

TABLE 8

(LC)MS analytical data - $R_t$ means retention time (in minutes), [MH]$^+$ means the protonated mass of the compound (free base), Method refers to the method used for (LC)MS.

| Comp. Nr. | $R_t$ | [MH]$^+$ | Method |
|---|---|---|---|
| 1 | — | 547 | 3 |
| 2 | 1.46 | 608 | 1 |
| 3 | 1.48 | 607 | 1 |
| 4 | 1.24 | 535 | 1 |
| 5 | 1.40 | 565 | 1 |
| 6 | n.d. | n.d. | |
| 7 | 1.39 | 558 | 1 |
| 8 | n.d. | n.d. | |
| 9 | n.d. | n.d. | |
| 10 | 5.61 | 483 | 2 |
| 11 | 4.24 | 490 | 2 |
| 12 | 1.35 | 538 | 1 |
| 13 | 1.16 | 552 | 1 |
| 14 | 1.33 | 535 | 1 |
| 15 | 1.19 | 536 | 1 |
| 16 | 1.23 | 536 | 1 |
| 17 | 1.30 | 566 | 1 |
| 18 | — | 594 | 3 |
| 19 | 1.38 | 562 | 1 |
| 20 | 1.38 | 562 | 1 |
| 21 | 1.21 | 535 | 1 |
| 22 | 0.88 | 535 | 1 |
| 23 | 0.92 | 535 | 1 |
| 24 | 0.92 | 535 | 1 |
| 25 | 1.16 | 535 | 1 |
| 26 | 1.17 | 563 | 1 |
| 27 | 1.29 | 563 | 1 |
| 28 | 1.30 | 563 | 1 |
| 29 | 1.04 | 536 | 1 |
| 30 | 1.25 | 551 | 1 |
| 31 | 1.11 | 551 | 1 |
| 33 | 1.12 | 537 | 1 |
| 34 | 1.25 | 545 | 1 |
| 35 | 1.41 | 601 | 1 |
| 36 | — | 559 | 3 |
| 37 | 1.23 | 552 | 1 |
| 38 | 1.19 | 554 | 1 |
| 39 | 1.27 | 554 | 1 |
| 40 | 1.21 | 554 | 1 |
| 41 | 1.15 | 602 | 1 |
| 42 | 1.12 | 602 | 1 |
| 43 | 1.11 | 602 | 1 |
| 44 | 0.86 | 571 | 1 |
| 45 | 1.04 | 585 | 1 |
| 46 | 4.04 | 447 | 2 |
| 47 | 4.41 | 477 | 2 |
| 48 | 5.25 | 479 | 2 |
| 49 | 4.23 | 475 | 2 |
| 50 | — | 579 | 3 |
| 51 | — | 561 | 3 |
| 53 | 1.43 | 633 | 1 |
| 54 | 1.37 | 609 | 1 |
| 55 | 1.26 | 593 | 1 |
| 56 | 1.29 | 544 | 1 |
| 57 | — | 578 | 3 |
| 58 | 1.38 | 626 | 1 |
| 59 | 1.37 | 626 | 1 |
| 60 | — | 558 | 3 |
| 61 | — | 586 | 3 |
| 62 | 1.43 | 600 | 1 |
| 63 | — | 570 | 3 |
| 64 | — | 598 | 3 |
| 65 | 1.40 | 634 | 1 |
| 66 | — | 627 | 3 |
| 67 | 1.32 | 599 | 1 |
| 68 | 1.43 | 629 | 1 |
| 69 | 1.36 | 525 | 1 |
| 70 | 1.32 | 559 | 1 |
| 71 | 1.41 | 587 | 1 |
| 72 | 1.40 | 617 | 1 |
| 73 | 1.14 | 588 | 1 |
| 74 | 1.32 | 559 | 1 |
| 75 | 1.35 | 573 | 1 |
| 76 | 1.42 | 587 | 1 |
| 77 | 1.41 | 587 | 1 |
| 78 | 1.40 | 601 | 1 |
| 79 | 1.44 | 601 | 1 |
| 80 | 1.33 | 575 | 1 |
| 81 | 1.41 | 589 | 1 |
| 82 | 1.37 | 573 | 1 |
| 83 | 1.36 | 587 | 1 |
| 84 | 1.31 | 605 | 1 |

TABLE 8-continued (LC)MS analytical data - R$_t$ means retention time (in minutes), [MH]$^+$ means the protonated mass of the compound (free base), Method refers to the method used for (LC)MS.

| Comp. Nr. | R$_t$ | [MH]$^+$ | Method |
|---|---|---|---|
| 85 | 1.40 | 587 | 1 |
| 86 | 1.43 | 603 | 1 |
| 87 | 1.43 | 617 | 1 |
| 88 | — | 623 | 3 |
| 89 | 1.35 | 579 | 1 |
| 90 | 1.31 | 563 | 1 |
| 91 | — | 671 | 3 |
| 92 | — | 590 | 3 |
| 93 | 1.39 | 591 | 1 |
| 94 | 1.33 | 593 | 1 |
| 95 | 1.30 | 604 | 1 |
| 96 | 1.33 | 659 | 1 |
| 97 | — | 779 | 3 |
| 98 | — | 659 | 3 |
| 99 | 1.39 | 647 | 1 |
| 100 | 1.43 | 651 | 1 |
| 101 | 1.32 | 618 | 1 |
| 102 | 1.36 | 607 | 1 |
| 103 | 1.37 | 651 | 1 |
| 104 | 1.41 | 665 | 1 |
| 105 | 1.41 | 637 | 1 |
| 106 | 1.33 | 603 | 1 |
| 107 | 1.34 | 508 | 1 |
| 108 | 1.38 | 572 | 1 |
| 109 | 1.44 | 586 | 1 |
| 110 | 1.39 | 586 | 1 |
| 111 | 1.35 | 604 | 1 |
| 112 | 1.43 | 586 | 1 |
| 113 | 1.36 | 592 | 1 |
| 114 | 1.35 | 658 | 1 |
| 115 | 1.45 | 650 | 1 |
| 116 | 1.39 | 617 | 1 |
| 117 | 1.42 | 606 | 1 |
| 118 | 1.43 | 650 | 1 |
| 119 | — | 508 | 3 |
| 120 | — | 562 | 3 |
| 121 | 1.36 | 556 | 1 |
| 122 | 1.41 | 584 | 1 |
| 123 | 1.35 | 586 | 1 |
| 124 | 1.20 | 585 | 1 |
| 125 | 1.23 | 541 | 1 |
| 126 | 1.17 | 546 | 1 |
| 127 | 1.38 | 631 | 1 |
| 128 | 1.36 | 572 | 1 |
| 129 | 5.69 | 635 | 2 |
| 130 | 5.75 | 621 | 6 |
| 131 | 1.38 | 537 | 1 |
| 132 | 8.42 | 552 | 5 |
| 133 | 0.94 | 600 | 1 |
| 134 | 1.27 | 536 | 1 |
| 135 | 5.52 | 513 | 2 |
| 136 | 1.03 | 678 | 1 |
| 137 | 7.14 | 651 | 2 |
| 138 | 1.48 | 652 | 7 |
| 139 | 7.04 | 539 | 4 |
| 140 | 5.12 | 610 | 2 |
| 141 | 1.43 | 470 | 1 |
| 142 | 1.34 | 492 | 1 |
| 143 | 1.40 | 624 | 7 |
| 144 | n.d. | n.d. | — |
| 145 | 0.96 | 609 | 1 |
| 146 | 0.89 | 595 | 1 |

TABLE 9

(LC)MS analytical data - R$_t$ means retention time (in minutes), [MH]$^-$ means the deprotonated mass of the compound (negative mode), Method refers to the method used for (LC)MS.

| Comp. Nr. | R$_t$ | [MH]$^-$ | Method |
|---|---|---|---|
| 52 | — | 573 | 3 |
| 32 | 1.05 | 535 | 1 |

Melting Points

For a number of compounds, melting points (m.p.) were determined by using a DSC823e (Mettler-Toledo). Melting points were measured with a temperature gradient of 30° C./minute. Maximum temperature was 400° C. Values are peak values. The results are gathered in Table 10

TABLE 10

| Comp. Nr. | m.p. (° C.) |
|---|---|
| 132 | 238.13 |
| 136 | 254.77 |
| 137 | 270.85 |
| 139 | 212.69 |
| 140 | 247.52 |

For a number of compounds, m.p. were determined by using a Gallenkamp apparatus from Sanyo Gallenkamp.
Comp. Nr. 138: 198-199° C.; Comp. Nr. 143: 249-250° C.; Comp. Nr. 133: 237-239° C.; Comp. Nr. 145: 218-221° C.; Comp. Nr. 146: 208-210° C.

D. Pharmacological Example

A) Measurement of Inhibition of Dgat1 Activity by the Present Compounds

The inhibiting activity of the present compounds on DGAT1 activity was screened in a single well procedure assay using DGAT1 comprising membrane preparations and DGAT1 substrate comprising micelles and determining formed radio-active triacylglycerol coming in close proximity of a flashplate surface by radio luminescence.

Said assay is described in full detail in WO2006/067071, the content of which is incorporated herein by reference.

By DGAT1 activity is meant the transfer of coenzyme A activated fatty acids to the 3-position of 1,2-diacylglycerols, thus forming a triglyceride molecule, by enzyme DGAT1.

Step 1 of the Assay: Expression of DGAT1 human DGAT1 (NM012079.2) was cloned into the pFast-Bac vector, containing translation start, a FLAG-tag at the N-terminus as described in literature and a viral Kozak sequence (AAX) preceding the ATG to improve expression in insect cells. Expression was done as described in literature (Cases, S., Smith, S. J., Zheng, Y., Myers H. M., Lear, S. R., Sande, E., Novak, S., Collins, C., Welch, C. B., Lusis, A. J., Erickson, S. K. and Farese, R. V. (1998) *Proc. Natl. Acad. Sci. USA* 95, 13018-13023.) using SF9 cells.

Step 2 of the Assay: Preparation of DGAT1 Membranes 72 h transfected SF9 cells were collected by centrifugation (13000 rpm-15 min-4° C.) and lysed in 2×500 ml lysis buffer (0.1M Sucrose, 50 mM KCl, 40 mM KH$_2$PO$_4$, 30 mM EDTA pH 7.2. Cells were homogenized by cell disruptor. After centrifugation 1380 rpm-15 min-4° C. (SN discarded), pellet was resuspended in 500 ml lysis buffer and total cell membranes collected by ultracentrifugation at 34000 rpm (100 000 g) for 60 min (4° C.). The collected membranes were resuspended in lysis buffer, divided in aliquots and stored with 10% glycerol at −80° C. until use.

Step 3 of the Assay: Preparation of DGAT Substrate Comprising Micelles

Materials a) 1,2-dioleoyl-sn-glycerol, 10 mg/ml (1,2-diacylglycerol (DAG))
   Dissolve in acetonitrile; evaporate the acetonitrile solution under nitrogen and reconstitute in chloroform at a final concentration of 10 mg/ml.
b) L-α-phosphatidylcholine, 1 mg/ml (phosphatidylcholine (PC))
   Dissolve in chloroform at a final concentration of 1 mg/ml and store at 4° C.
c) L-α-phosphatidyl-L-serine, 1 mg/ml (phophatidylserine (PS))
   Dissolve in chloroform at a final concentration of 1 mg/ml and store at 4° C.

Method

Add 1 ml dioleoyl-sn-glycerol (10 mg/ml) to 10 ml of L-α-phosphatidylcholine (1 mg/ml) and 10 ml of L-α-phosphatidyl-L-serine (1 mg/ml) in a thick glass recipient. Evaporate under nitrogen and put on ice for 15 minutes. Reconstitute in 10 ml Tris/HCl (10 mM, pH 7.4) by sonication on ice. The sonification process consists of sonification cycles of 10 seconds in the sonification bath followed by 10 seconds cool down on ice and repeating this sonification cycle till a homogeneous solution is obtained (takes about 15 minutes). The thus obtained micelles are stored at −20° C. till later use and contain DAG at a final concentration of 1.61 mM.

Step 4 of the Assay: DGAT Flashplate™ Assay

Materials a) Assaybuffer
   50 mM Tris-HCl (pH 7.4), 150 mM $MgCl_2$, 1 mM EDTA, 0.2% BSA.
b) N-ethylmaleimide, 5M
   Dissolve 5 g into a final volume of 8 ml DMSO 100% and store at −20° C. in aliquots till later use.
c) Substrate mix (for 1 384 well plate=3840 µl)
   612 µl micelles stock (5104 final)
   16.6 µl oleoylCoA 9.7 mM
   23 µl [$^3$H]-oleoylCoA (49 Ci/mmol, 500 µCi/ml)
   3188.4 µl Tris pH 7.4, 10 mM
d) Enzyme mix (for 1 384 well plate=3520 µl) (5 µg/ml)
   Add 11.73 µl of DGAT membrane stock (1500 µg/ml stock) to 3508 µl assay buffer.
e) Stop mix (for 1 384 well plate=7.68 ml) (250 mM)
   Add 384 µl of N-ethylmaleimide (5M) to 3.456 ml DMSO 100%, and further dilute 3.84 ml of said solution with 3.84 ml DMSO 10%.

Method

DGAT activity in membrane preparations was assayed in 50 mM Tris-HCl (pH 7.4), 150 mM $MgCl_2$, 1 mM EDTA and 0.2% BSA, containing 50 µM DAG, 32 µg/ml PC/PS and 8.4 µM [$^3$H]-oleoylCoA (at a specific activity of 30 nCi/well) in a final volume of 50 µl in 384-well format using the red shifted Basic Image FlashPlate™ (Perkin Elmer Cat. No. SMP400).

In detail, 10 µl enzyme mix and 10 µl substrate mix were added to 30 µl of assay buffer, optionally in the presence of 1 µl DMSO (blank and controls) or 1 µl of the compound to be tested. This reaction mixture was incubated for 120 minutes at 37° C. and the enzymatic reaction stopped by adding 20 µl of the stop mix. The plates were sealed and the vesicles allowed to settle overnight at room temperature. Plates were centrifuged for 5 minutes at 1500 rpm and measured in Leadseeker.

Experiments with different concentrations of the test compound were performed and curves were calculated and drawn based on % $CTRL_{min}$ (% of normalized control). % $CTRL_{min}$ was calculated according to equation 1, $$\% \ CTRL_{min} = (sample - LC)/(HC - LC) \qquad \text{Equation 1}$$

where HC (high control) refers to the median of radioluminescence value measured in the wells with enzyme and substrate but without test compound, LC (low control) refers to median background radioluminescence value measured in the wells with substrate without enzyme and without test compound, and sample refers to the radioluminescence value measured in the wells with substrate, enzyme and test compound at a particular concentration.

The calculated % $CTRL_{min}$ values form a sigmoidal dose response descending curve and from this curve $pIC_{50}$ values were calculated ($-logIC_{50}$ where $IC_{50}$ represents the concentration at which the test compound gives 50% inhibition of DGAT1 activity). Table 11 shows the $pIC_{50}$ values for the compounds of formula (I).

In order to determine selectivity of the present compounds for DGAT1 compared to DGAT2, the inhibiting activity of the compounds on DGAT2 was also determined in the above assay, slightly modified to obtain optimal assay conditions for DGAT2. The tested compounds did not show inhibiting activity for DGAT2 (Human DGAT2 (NM032564) was cloned and expressed as described in J. Biol. Chem. 276(42), pp 38870-38876 (2001)).

TABLE 11

$pIC_{50}$ values ($IC_{50}$ values expressed in M; $pIC_{50} = -logIC_{50}$)

| Comp. no. | $pIC_{50}$ |
| --- | --- |
| 12 | 8.87 |
| 13 | 7.96 |
| 4 | 7.61 |
| 14 | 9.01 |
| 15 | 7.89 |
| 16 | 7.92 |
| 17 | 8.68 |
| 18 | 7.39 |
| 19 | 6.84 |
| 20 | 7.51 |
| 21 | 8.05 |
| 22 | 5.86 |
| 23 | 7.48 |
| 24 | 6.46 |
| 25 | 7.15 |
| 26 | 6.40 |
| 27 | 8.41 |
| 28 | 8.30 |
| 29 | 6.11 |
| 30 | 8.35 |
| 31 | 6.57 |
| 32 | 5.48 |
| 33 | 5.71 |
| 34 | 7.69 |
| 35 | 6.93 |
| 36 | 8.76 |
| 37 | 8.76 |
| 38 | 7.96 |
| 39 | 6.42 |
| 40 | 8.18 |
| 41 | 7.72 |
| 42 | 5.93 |
| 43 | 6.36 |
| 44 | 7.00 |
| 45 | 7.25 |
| 46 | 5.62 |
| 47 | 5.27 |
| 48 | 5.45 |
| 10 | 6.49 |

TABLE 11-continued pIC$_{50}$ values (IC$_{50}$ values expressed in M; pIC$_{50}$ = −logIC$_{50}$)

| Comp. no. | pIC$_{50}$ |
|---|---|
| 49 | 5.05 |
| 1 | 8.09 |
| 50 | 6.53 |
| 51 | 6.31 |
| 52 | 7.76 |
| 3 | 5.93 |
| 53 | 5.83 |
| 54 | 6.15 |
| 55 | 7.58 |
| 56 | 6.48 |
| 57 | 6.19 |
| 58 | 6.45 |
| 59 | 5.69 |
| 60 | 7.76 |
| 61 | 6.37 |
| 62 | 6.26 |
| 63 | 6.92 |
| 64 | 6.88 |
| 11 | 5.95 |
| 2 | 6.95 |
| 65 | 6.69 |
| 66 | 7.23 |
| 67 | 6.83 |
| 6 | 5.04 |
| 68 | 5.14 |
| 8 | 6.67 |
| 69 | 5.10 |
| 5 | 5.12 |
| 70 | 5.26 |
| 71 | 5.45 |
| 72 | 5.11 |
| 73 | 5.45 |
| 74 | 5.96 |
| 75 | 5.67 |
| 76 | 5.12 |
| 77 | 5.35 |
| 78 | 5.12 |
| 79 | 5.19 |
| 80 | 5.26 |
| 81 | 5.09 |
| 82 | 6.57 |
| 83 | 5.81 |
| 84 | 5.28 |
| 85 | 6.75 |
| 86 | 5.01 |
| 87 | 5.13 |
| 88 | 5.86 |
| 89 | 5.77 |
| 90 | 5.53 |
| 91 | 5.82 |
| 92 | 5.63 |
| 93 | 5.32 |
| 94 | 6.83 |
| 9 | 7.52 |
| 95 | 6.39 |
| 96 | 6.28 |
| 97 | 6.31 |
| 98 | 5.58 |
| 99 | 5.74 |
| 100 | 5.81 |
| 101 | 6.28 |
| 102 | 6.77 |
| 103 | 6.70 |
| 104 | 5.70 |
| 105 | 5.48 |
| 106 | 5.14 |
| 107 | 5.61 |
| 7 | 5.46 |
| 108 | 5.35 |
| 109 | 5.02 |
| 110 | 6.02 |
| 111 | 5.34 |
| 112 | 6.57 |
| 113 | 5.97 |
| 114 | 5.91 |
| 115 | 5.71 |
| 116 | 5.66 |
| 117 | 6.50 |
| 118 | 6.20 |
| 119 | 5.33 |
| 120 | 5.37 |
| 121 | 5.31 |
| 122 | 5.82 |
| 123 | 5.38 |
| 124 | 5.17 |
| 125 | 8.55 |
| 126 | 8.02 |
| 127 | 7.60 |
| 128 | 6.18 |
| 129 | 8.27 |
| 130 | 8.14 |
| 131 | 7.51 |
| 132 | 7.34 |
| 133 | 6.67 |
| 134 | 5.89 |
| 135 | 5.03 |
| 136 | 8.74 |
| 137 | 8.38 |
| 138 | 7.94 |
| 139 | 8.19 |
| 140 | 7.90 |
| 141 | 6.96 |
| 142 | 6.75 |
| 143 | 5.48 |
| 144 | 5.13 |
| 145 | 6.95 |
| 146 | 5.47 |

B) In Vivo Study for Effect of Test Compound on GLP-1 Plasma Levels

Elevation of GLP-1 plasma levels by a DGAT inhibitor can be studied as follows:

Dogs are deprived from food for a period of 22 hours. At time 0, animals are given a liquid meal, containing 18% fat (w/w), by gavage with a stomach tube. The test compound is given orally together with the meal. Afterwards, a postprandial plasma profile is determined for GLP-1. Therefore, blood is collected at predetermined time intervals in ice-cooled Vacutainers EDTA-plasma tubes and GLP-1 levels are measured in the samples taken at 0 hour (just before the meal) and at 0.5, 1, 2, 4, 6, 8 and 24 hours after dosing. Six dogs (3 males and 3 females) are included per dosage group and the plasma GLP-1 profile is compared with their own GLP-1 profile previously determined in the same conditions but without administration of the test compound.

GLP-1 determinations in plasma are performed with a Glucagon-like peptide-1 (active) ELISA kit 96-well plate of LINCO Research.

E. Composition Examples

"Active ingredient" (a.i.) as used throughout these examples relates to a compound of formula (I), including any stereochemically isomeric form thereof, a N-oxide thereof, a pharmaceutically acceptable salt thereof or a solvate thereof; in particular to any one of the exemplified compounds.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

The invention claimed is:

1. A compound of formula

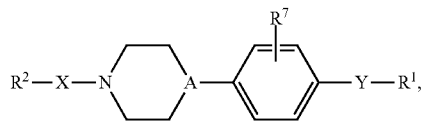

(I)

including any stereochemically isomeric form thereof, wherein

A represents N;

X represents —O—C(=O)—; —C(=O)—C(=O)—; —NR$^x$—C(=O)—; —Z—C(=O)—; —Z—NR$^x$—C(=O)—; —C(=O)—Z—; —NR$^x$—C(=O)—Z—; —C(=S)—; —NR$^x$—C(=S)—; —Z—C(=S)—; —Z—NR$^x$—C(=S)—; —C(=S)—Z—; or —NR$^x$—C(=S)—Z—;

Z represents a bivalent radical selected from $C_{1-6}$alkanediyl, $C_{2-6}$alkenediyl or $C_{2-6}$alkynediyl; wherein each of said $C_{1-6}$alkanediyl, $C_{2-6}$alkenediyl or $C_{2-6}$alkynediyl may optionally be substituted with hydroxyl or amino; and wherein two hydrogen atoms attached to the same carbon atom in $C_{1-6}$alkanediyl may optionally be replaced by $C_{1-6}$alkanediyl;

R$^x$ represents hydrogen or $C_{1-4}$alkyl;

Y represents —C(=O)—NR$^x$— or —NR$^x$—C(=O)—;

R$^1$ represents adamantanyl, $C_{3-6}$cycloalkyl; aryl$^1$ or Het$^1$;

R$^2$ represents $C_{3-6}$cycloalkyl, phenyl, naphthalenyl, 2,3-dihydro-1,4-benzodioxinyl, 1,3-benzodioxolyl, 2,3-dihydrobenzofuranyl or a 6-membered aromatic heterocycle containing 1 or 2 N atoms, wherein said $C_{3-6}$cycloalkyl, phenyl, naphthalenyl, 2,3-dihydro-1,4-benzodioxinyl, 1,3-benzodioxolyl or a 6-membered aromatic heterocycle containing 1 or 2 N atoms is substituted with two, three, four or five substituents, each substituent independently selected from the group consisting of hydroxyl; carboxyl; halo; $C_{1-6}$alkyl optionally substituted with hydroxy; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxycarbonyl wherein $C_{1-6}$alkyl may optionally be substituted with aryl; cyano; $C_{1-6}$alkylcarbonyl; nitro; amino; mono- or di($C_{1-4}$alkyl)amino; $C_{1-4}$alkylcarbonylamino; —S(=O)$_p$—$C_{1-4}$alkyl; R$^4$R$^3$N—C(=O)—; R$^4$R$^3$N—$C_{1-6}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—$C_{1-4}$alkyl; aryl-C(=O)—; Het; Het$C_{1-4}$alkyl; Het-C(=O)—$C_{1-4}$alkyl; Het-C(=O)—; and Het-O—;

R$^3$ represents hydrogen; $C_{1-4}$alkyl optionally substituted with hydroxyl or $C_{1-4}$alkyloxy; R$^6$R$^5$N—$C_{1-4}$alkyl; $C_{1-4}$alkyloxy; Het; Het-$C_{1-4}$alkyl; aryl; or R$^6$R$^5$N—C(=O)—$C_{1-4}$alkyl;

R$^4$ represents hydrogen or $C_{1-4}$alkyl;

R$^5$ represents hydrogen; $C_{1-4}$alkyl; or $C_{1-4}$alkylcarbonyl;

R$^6$ represents hydrogen or $C_{1-4}$alkyl; or

R$^5$ and R$^6$ may be taken together with the nitrogen to which they are attached to form a saturated monocyclic 5, 6 or 7-membered heterocycle which may further contain one or more heteroatoms each independently selected from the group consisting of O, S, S(=O)$_p$ and N; and which heterocycle may optionally be substituted with $C_{1-4}$alkyl;

R$^7$ represents hydrogen; halo; $C_{1-4}$alkyl; or $C_{1-4}$alkyl substituted with hydroxyl;

aryl represents phenyl or phenyl substituted with at least one substituent, each substituent independently being selected from the group consisting of hydroxyl; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; and —S(=O)$_p$—$C_{1-4}$alkyl;

aryl$^1$ represents phenyl, or fluorenyl; each of said phenyl, or fluorenyl optionally substituted with one or two substituents, each substituent independently being selected from the group consisting of oxo; carboxyl; halo; $C_{1-6}$alkyl optionally substituted with carboxyl or $C_{1-4}$alkyloxycarbonyl; $C_{1-6}$alkyloxy; $C_{1-6}$alkyloxy-carbonyl; amino; aryl; and Het;

Het represents a monocyclic non-aromatic or aromatic heterocycle containing at least one heteroatom each independently selected from the group consisting of O, S, S(=O)$_p$ and N; or a bicyclic or tricyclic non-aromatic or aromatic heterocycle containing at least one heteroatom each independently selected from the group consisting of O, S, S(=O)$_p$ and N; said monocyclic heterocycle or said bi- or tricyclic heterocycle optionally being substituted with at least one substituent, each substituent independently being selected from the group consisting of hydroxyl; oxo; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; and —S(=O)$_p$—$C_{1-4}$alkyl;

Het$^1$ represents a monocyclic non-aromatic or aromatic heterocycle containing at least one heteroatom each independently selected from the group consisting of S and N; said monocyclic heterocycle optionally being substituted with at least one substituent, each substituent independently being selected from the group consisting of hydroxyl; oxo; carboxyl; halo; $C_{1-6}$alkyl optionally substituted with aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; nitro; amino; mono- or di($C_{1-6}$alkyl)amino; $R^4R^3N$—$C_{1-6}$alkyl $C_{3-6}$cycloalkyl-$NR^x$—; aryl-$NR^x$—; Het-$NR^x$—; $C_{3-6}$cycloalkyl$C_{1-4}$alkyl-$NR^x$—; aryl$C_{1-4}$alkyl-$NR^x$—; Het$C_{1-4}$alkyl-$NR^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—$C_{1-4}$alkyl; aryl-C(=O)—; Het; Het$C_{1-4}$alkyl; Het-C(=O)—$C_{1-4}$alkyl; Het-C(=O)—; and Het-O—;

p represents 1 or 2;

a N-oxide thereof, or a pharmaceutically acceptable salt thereof.

2. The compound as claimed in claim 1 having the following formula

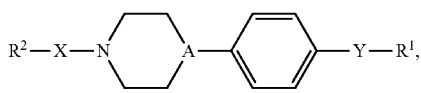

(I)

including any stereochemically isomeric form thereof, wherein

A represents N;

X represents —$NR^x$—C(=O)—; —Z—C(=O)—; —Z—$NR^x$—C(=O)—; —C(=O)—Z—; —$NR^x$—C(=O)—Z—; —C(=S)—; —$NR^x$—C(=S)—; —Z—C(=S)—; —Z—$NR^x$—C(=S)—; —C(=S)—Z—; or —$NR^x$—C(=S)—Z—;

Z represents a bivalent radical selected from $C_{1-6}$alkanediyl, $C_{2-6}$alkenediyl or $C_{2-6}$alkynediyl; wherein each of said $C_{1-6}$alkanediyl, $C_{2-6}$alkenediyl or $C_{2-6}$alkynediyl may optionally be substituted with hydroxyl;

$R^x$ represents hydrogen or $C_{1-4}$alkyl;

Y represents —C(=O)—$NR^x$— or —$NR^x$—C(=O)—;

$R^1$ represents $C_{3-6}$cycloalkyl; aryl$^1$ or Het$^1$;

$R^2$ represents $C_{3-6}$cycloalkyl, phenyl, naphthalenyl, 2,3-dihydro-1,4-benzodioxinyl, 1,3-benzodioxolyl, wherein said $C_{3-6}$cycloalkyl, phenyl, naphtalenyl, 2,3-dihydro-1,4-benzodioxinyl, 1,3-benzodioxolyl is substituted with two, three, four, or five substituents, each substituent independently selected from the group consisting of hydroxyl; carboxyl; halo; $C_{1-6}$alkyl optionally substituted with hydroxy; polyhalo$C_{1-6}$alkyl; $C_{1-6}$alkyloxy optionally substituted with $C_{1-4}$alkyloxy; $C_{1-6}$alkylthio; polyhalo-$C_{1-6}$alkyloxy; $C_{1-6}$alkyloxycarbonyl wherein $C_{1-6}$alkyl may optionally be substituted with aryl; cyano; $C_{1-6}$alkylcarbonyl; nitro; amino; mono- or di($C_{1-4}$alkyl)amino; —S(=O)$_p$—$C_{1-4}$alkyl; $R^4R^3N$—C(=O)—; $R^4R^3N$—$C_{1-6}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; Het; Het$C_{1-4}$alkyl; Het-C(=O)—; and Het-O—;

$R^3$ represents hydrogen; $C_{1-4}$alkyl optionally substituted with hydroxyl or $C_{1-4}$alkyloxy; $R^6R^5N$—$C_{1-4}$alkyl; $C_{1-4}$alkyloxy; Het; aryl; or $R^6R^5N$—C(=O)—$C_{1-4}$alkyl;

$R^4$ represents hydrogen or $C_{1-4}$alkyl;

$R^5$ represents hydrogen; $C_{1-4}$alkyl; or $C_{1-4}$alkylcarbonyl;

$R^6$ represents hydrogen or $C_{1-4}$alkyl; or $R^5$ and $R^6$ may be taken together with the nitrogen to which they are attached to form a saturated monocyclic 5, 6 or 7-membered heterocycle which may further contain one or more heteroatoms each independently selected from the group consisting of O, S, S(=O)$_p$ and N; and which heterocycle may optionally be substituted with $C_{1-4}$alkyl;

aryl represents phenyl or phenyl substituted with at least one substituent, substituent independently being selected from the group consisting of hydroxyl; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl)amino; and —S(=O)$_p$—$C_{1-4}$alkyl;

aryl$^1$ represents phenyl, or fluorenyl; each of said phenyl, or fluorenyl optionally substituted with one or two substituents, each substituent independently being selected from the group consisting of oxo; carboxyl; halo; $C_{1-6}$alkyl; $C_{1-6}$alkyloxy; $C_{1-6}$alkyloxy-carbonyl; amino; aryl; and Het;

Het represents a monocyclic non-aromatic or aromatic heterocycle containing at least one heteroatom each independently selected from the group consisting of O, S, S(=O)$_p$ and N; or a bicyclic or tricyclic non-aromatic or aromatic heterocycle containing at least one heteroatom each independently selected from the group consisting of O, S, S(=O)$_p$ and N; said monocyclic heterocycle or said bi- or tricyclic heterocycle optionally being substituted with at least one substituent, each substituent independently being selected from the group consisting of hydroxyl; oxo; carboxyl; halo; $C_{1-6}$alkyl optionally substituted with $C_{1-4}$alkyloxy, amino or mono- or di($C_{1-4}$alkyl)amino; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxycarbonyl; cyano; aminocarbonyl; mono- or di($C_{1-4}$alkyl)aminocarbonyl; $C_{1-6}$alkylcarbonyl; nitro; amino; mono- or di($C_{1-4}$alkyl) amino; and —S(=O)$_p$—$C_{1-4}$alkyl;

Het$^1$ represents a monocyclic non-aromatic or aromatic heterocycle containing at least one heteroatom each independently selected from the group consisting of S and N; said monocyclic heterocycle optionally being substituted with at least one substituent, each substituent independently being selected from the group consisting of hydroxyl; oxo; carboxyl; halo; $C_{1-6}$alkyl optionally substituted with aryl-C(=O)—; hydroxy$C_{1-6}$alkyl optionally substituted with aryl or aryl-C(=O)—; polyhalo$C_{1-6}$alkyl; $C_{1-6}$alkyloxy optionally substituted with $C_{1-4}$alkyloxy; $C_{1-6}$alkylthio; polyhalo$C_{1-6}$alkyloxy; $C_{1-6}$alkyloxy-carbonyl wherein $C_{1-6}$alkyl may optionally be substituted with aryl; cyano; aminocarbonyl; mono- or di($C_{1-4}$alkyl)aminocarbonyl; $C_{1-6}$alkylcarbonyl; nitro; amino; mono- or di($C_{1-6}$alkyl)amino; $C_{3-6}$cycloalkyl-$NR^x$—; aryl-$NR^x$—; Het-$NR^x$—; $C_{3-6}$cycloalkyl$C_{1-4}$alkyl-$NR^x$—; aryl$C_{1-4}$alkyl-$NR^x$—; Het$C_{1-4}$ alkyl-$NR^x$—; —S(=O)$_p$—$C_{1-4}$alkyl; $C_{3-6}$cycloalkyl; $C_{3-6}$cycloalkyl$C_{1-4}$alkyl; $C_{3-6}$cycloalkyl-C(=O)—; aryl; aryloxy; aryl$C_{1-4}$alkyl; aryl-C(=O)—; Het; Het$C_{1-4}$alkyl; Het-C(=O)—; and Het-O—;

p represents 1 or 2;

a N-oxide thereof, or a pharmaceutically acceptable salt thereof.

3. The compound as claimed in claim 1 wherein X represents —O—C(=O); —NR$^x$—C(=O)—; —Z—C(=O)—; —Z—NR$^x$—C(=O)—; or —NR$^x$—C(=S)—.

4. The compound as claimed in claim 3 wherein X represents —NR$^x$—C(=O)— or —Z—C(=O)—.

5. The compound as claimed in any one of the preceding-claim 1 wherein R$^1$ represents optionally substituted phenyl, optionally substituted fluorenyl or an optionally substituted monocyclic non-aromatic or aromatic heterocycle containing at least one heteroatom each independently selected from the group consisting of S and N.

6. The compound as claimed in claim 1 wherein R$^2$ represents C$_{3-6}$cycloalkyl, phenyl, 2,3-dihydro-1,4-benzodioxinyl or a 6-membered aromatic heterocycle containing 1 or 2 N atoms, wherein said phenyl or heterocycle are optionally substituted with two, three, or four substituents.

7. The compound as claimed in claim 1 wherein the compound has the following formula

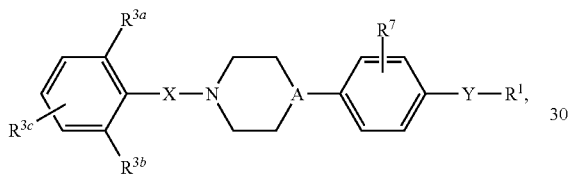

(I')

wherein R$^{3a}$ and R$^{3b}$ each independently represent hydrogen; hydroxyl; carboxyl; halo; C$_{1-6}$alkyl; polyhaloC$_{1-6}$alkyl; C$_{1-6}$alkyloxy optionally substituted with C$_{1-4}$alkyloxy; C$_{1-6}$alkylthio; polyhaloC$_{1-6}$alkyloxy; C$_{1-6}$alkyloxycarbonyl; cyano; aminocarbonyl; mono- or di(C$_{1-4}$alkyl)aminocarbonyl; C$_{1-6}$alkylcarbonyl; nitro; amino; mono- or di(C$_{1-4}$alkyl)amino; or —S(=O)$_p$—C$_{1-4}$alkyl; and wherein R$^{3c}$ represents hydrogen; hydroxyl; carboxyl; halo; C$_{1-6}$alkyl; polyhaloC$_{1-6}$alkyl; C$_{1-6}$alkyloxy optionally substituted with C$_{1-4}$alkyloxy; C$_{1-6}$alkylthio; polyhalo-C$_{1-6}$alkyloxy; C$_{1-6}$alkyloxycarbonyl wherein C$_{1-6}$alkyl may optionally be substituted with aryl; cyano; C$_{1-6}$alkylcarbonyl; nitro; amino; mono- or di(C$_{1-4}$alkyl)amino; —S(=O)$_p$—C$_{1-4}$alkyl; R$^4$R$^3$N—C(=O)—; R$^4$R$^3$N—C$_{1-6}$alkyl; C$_{3-6}$cycloalkyl; aryl; aryloxy; arylC$_{1-4}$alkyl; aryl-C(=O)—C$_{1-4}$alkyl; aryl-C(=O)—; Het; HetC$_{1-4}$alkyl; Het-C(=O)—C$_{1-4}$alkyl; Het-C(=O)—; or Het-O—.

8. The compound as claimed in claim 7 wherein the compound has the following formula

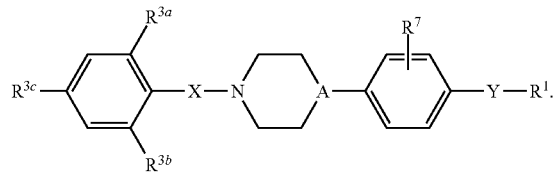

(I'')

9. The compound as claimed in claim 7 wherein R$^{3a}$ and R$^{3b}$ each independently represent halo or C$_{1-6}$alkyl.

10. The compound as claimed in claim 1 wherein R$^7$ represents hydrogen.

11. The compound as claimed in claim 1 wherein
X represents —O—C(=O)—; —NR$^x$—C(=O)—; —Z—C(=O)—; —Z—NR$^x$—C(=O)—; or —NR$^x$—C(=S)—;
Z represents C$_{1-6}$alkanediyl;
R$^x$ represents hydrogen;
R$^1$ represents aryl$^1$ or Het$^1$;
R$^2$ represents C$_{3-6}$cycloalkyl, phenyl, 2,3-dihydro-1,4-benzodioxinyl, or a 6-membered aromatic heterocycle containing 1 or 2 N atoms, wherein said C$_{3-6}$cycloalkyl, phenyl, 2,3-dihydro-1,4-benzodioxinyl, or heterocycle is substituted with two, three or four substituents, each substituent independently selected from the group consisting of halo; C$_{1-6}$alkyl; C$_{1-6}$alkyloxy; C$_{1-6}$alkylthio; C$_{1-6}$alkyloxycarbonyl; nitro; mono- or di(C$_{1-4}$alkyl)amino; R$^4$R$^3$N—C$_{1-6}$alkyl; aryloxy; and Het-C(=O)—C$_{1-4}$alkyl;
R$^3$ represents C$_{1-4}$alkyl; R$^4$ represents C$_{1-4}$alkyl; R$^7$ represents hydrogen or halo;
p represents 1 or 2.

12. The compound as claimed in claim 11 wherein
aryl represents phenyl or phenyl substituted with halo; C$_{1-6}$alkyl; polyhaloC$_{1-6}$alkyl; or C$_{1-6}$alkyloxycarbonyl;
Het represents a monocyclic non-aromatic or aromatic heterocycle containing at least one heteroatom each independently selected from the group consisting of O, S, S(=O)$_p$ and N; or a bicyclic non-aromatic or aromatic heterocycle containing at least one heteroatom each independently selected from N; said monocyclic heterocycle or said bicyclic heterocycle optionally being substituted with one or two substituents, each substituent independently being selected from oxo or C$_{1-6}$alkyl;
Het$^1$ represents a monocyclic non-aromatic or aromatic heterocycle containing at least one heteroatom each independently selected from S or N; said monocyclic heterocycle optionally being substituted with one or two substituents, each substituent independently being selected from the group consisting of hydroxyl; oxo; C$_{1-6}$alkyl; C$_{1-6}$alkyloxy-carbonyl; aryl; and Het.

13. The compound as claimed in claim 1 wherein the compound is selected from

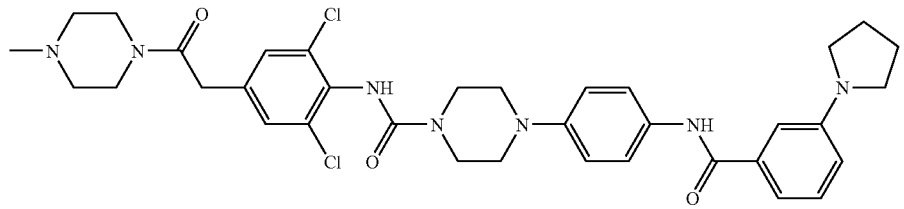

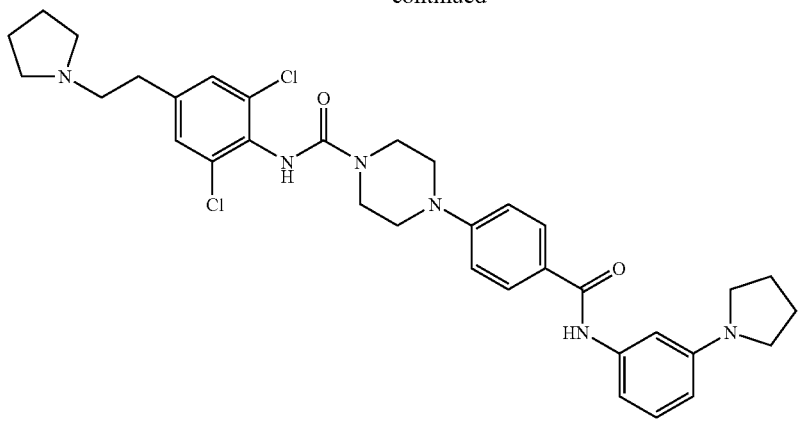
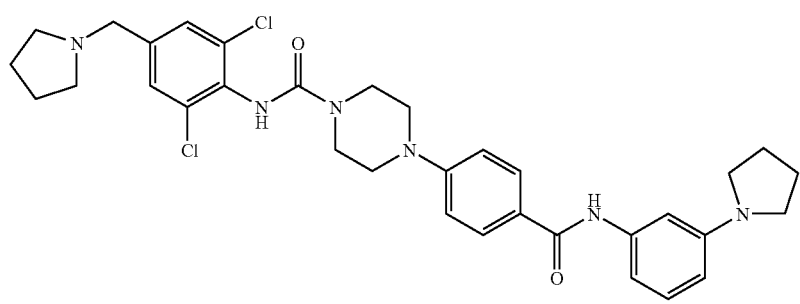
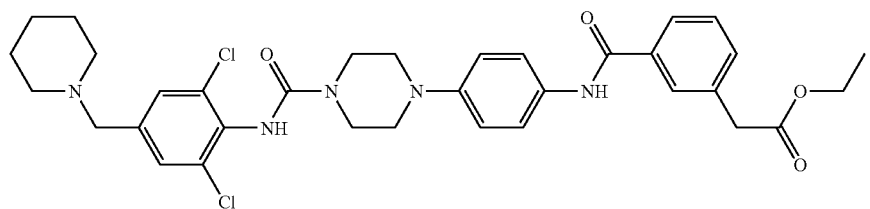
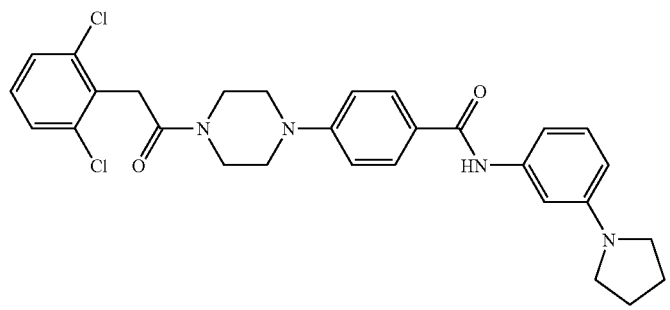
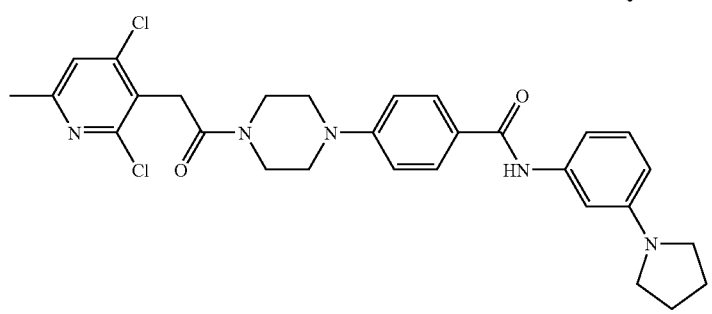

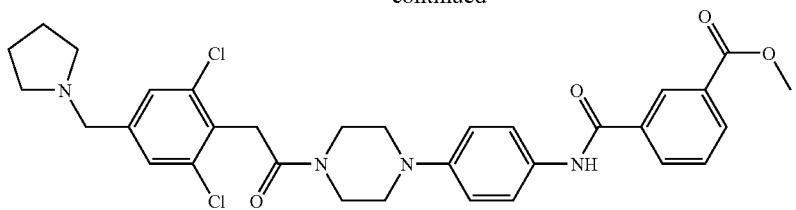
a N-oxide thereof, a pharmaceutically acceptable salt thereof.
14. A pharmaceutical composition comprising a pharmaceutically acceptable carrier, and as active ingredient a compound as claimed in claim 1.
* * * * *

UNITED STATES PATENT AND TRADEMARK OFFICE
CERTIFICATE OF CORRECTION

| | | |
|---|---|---|
| PATENT NO. | : 8,946,228 B2 | Page 1 of 1 |
| APPLICATION NO. | : 12/663011 | |
| DATED | : February 3, 2015 | |
| INVENTOR(S) | : Bongartz et al. | |

It is certified that error appears in the above-identified patent and that said Letters Patent is hereby corrected as shown below:

ON THE TITLE PAGE

Delete
"(22) PCT Filed: Jun. 6, 2008."

and insert
--(22) PCT Filed: Jun. 5, 2008.--

Signed and Sealed this
Fifteenth Day of March, 2016

Michelle K. Lee
*Director of the United States Patent and Trademark Office*